(12) United States Patent
Lipani

(10) Patent No.: US 9,789,313 B2
(45) Date of Patent: Oct. 17, 2017

(54) SYSTEM AND METHODS FOR DIAGNOSIS AND TREATMENT OF DISCOGENIC LOWER BACK PAIN

(71) Applicant: John D. Lipani, New Hope, PA (US)

(72) Inventor: John D. Lipani, New Hope, PA (US)

( * ) Notice: Subject to any disclaimer, the term of this patent is extended or adjusted under 35 U.S.C. 154(b) by 1 day.

(21) Appl. No.: 14/465,822

(22) Filed: Aug. 21, 2014

(65) Prior Publication Data

US 2015/0005680 A1    Jan. 1, 2015

Related U.S. Application Data

(63) Continuation-in-part of application No. 13/402,093, filed on Feb. 22, 2012, now Pat. No. 8,880,189, and
(Continued)

(51) Int. Cl.
*A61N 1/36* (2006.01)
*A61N 1/05* (2006.01)
(Continued)

(52) U.S. Cl.
CPC ...... *A61N 1/36071* (2013.01); *A61B 18/1492* (2013.01); *A61B 18/20* (2013.01); *A61F 7/12* (2013.01); *A61H 23/02* (2013.01); *A61N 1/0551* (2013.01); *A61N 1/0558* (2013.01); *A61N 1/36057* (2013.01); *A61N 1/36135* (2013.01);
(Continued)

(58) Field of Classification Search
None
See application file for complete search history.

(56) References Cited

U.S. PATENT DOCUMENTS

| | | |
|---|---|---|
| 3,727,616 A | 4/1973 | Lenzkes |
| 4,590,948 A | 5/1986 | Nilsson |
| (Continued) | | |

OTHER PUBLICATIONS

Imai S, Konttinen YT, Tokunaga Y, Maeda T, Hukuda S, Santavira S. An ultrastructural study of calcitonin gene-related peptide-immunoreactive nerve fibres innervating the rat posterior longitudinal ligament: a morphologic basis for their possible efferent actions. Spine, 22(1997): 1941-1947.
(Continued)

*Primary Examiner* — Carl H Layno
*Assistant Examiner* — Jennifer Ghand
(74) *Attorney, Agent, or Firm* — David R. Rigney

(57) ABSTRACT

Methods and devices to treat discogenic lumbar back pain are disclosed. Electrodes are implanted within the anterior epidural space of the patient. A pulse generator that is connected to the electrodes delivers electrical impulses to sympathetic nerves located within the posterior longitudinal ligament (PLL) of the lumbar spine and outer posterior annulus fibrosus of the intervertebral disc. In alternate embodiments, energy directed to nerves in the PLL may be from light or mechanical vibrations, or the nerves may be cooled. The electrodes may also be used diagnostically to correlate spontaneous nerve activity with spinal movement, fluctuations in autonomic tone and the patient's experience of pain. The electrodes may also be used to generate diagnostic evoked potentials. The diagnostic data are used to devise parameters for the therapeutic nerve stimulation. Automatic analysis of the data may be incorporated into a closed-loop system that performs the nerve stimulation automatically.

2 Claims, 10 Drawing Sheets

Related U.S. Application Data a continuation-in-part of application No. 14/099,910, filed on Dec. 7, 2013, now Pat. No. 8,892,215.

(60) Provisional application No. 61/463,800, filed on Feb. 23, 2011.

(51) Int. Cl.

| | | |
|---|---|---|
| *A61N 5/06* | (2006.01) | |
| *A61H 23/02* | (2006.01) | |
| *A61F 7/12* | (2006.01) | |
| *A61N 1/372* | (2006.01) | |
| *A61B 18/14* | (2006.01) | |
| *A61B 18/20* | (2006.01) | |
| *A61B 18/00* | (2006.01) | |
| *A61B 17/32* | (2006.01) | |
| *A61B 18/18* | (2006.01) | |

(52) U.S. Cl.
CPC ..... *A61N 1/36146* (2013.01); *A61N 1/36171* (2013.01); *A61N 1/36178* (2013.01); *A61N 1/37205* (2013.01); *A61N 1/37223* (2013.01); *A61N 5/0622* (2013.01); *A61B 17/320068* (2013.01); *A61B 2018/00047* (2013.01); *A61B 2018/00434* (2013.01); *A61B 2018/00577* (2013.01); *A61B 2018/00613* (2013.01); *A61B 2018/00815* (2013.01); *A61B 2018/00821* (2013.01); *A61B 2018/1807* (2013.01); *A61H 2205/081* (2013.01); *A61N 1/36167* (2013.01); *A61N 1/37211* (2013.01)

(56) References Cited

U.S. PATENT DOCUMENTS

| | | | |
|---|---|---|---|
| 4,633,889 | A | 1/1987 | Talalla |
| 6,249,703 | B1 | 6/2001 | Stanton |
| 6,438,423 | B1 | 8/2002 | Rezai |
| 6,622,048 | B1 | 9/2003 | Mann |
| 6,654,644 | B2 | 11/2003 | Sanchez-Zambrano |
| 6,772,012 | B2 | 8/2004 | Ricart |
| 6,830,570 | B1 | 12/2004 | Frey |
| 7,069,083 | B2 | 6/2006 | Finch |
| 7,239,912 | B2 | 7/2007 | Dobak |
| 7,270,659 | B2 | 9/2007 | Ricart |
| 7,331,956 | B2 | 2/2008 | Hovda |
| 7,359,751 | B1 | 4/2008 | Erickson |
| 7,418,292 | B2 | 8/2008 | Shafer |
| 7,634,307 | B2 | 12/2009 | Sweeney |
| 7,738,963 | B2 | 6/2010 | Hickman |
| 7,769,442 | B2 | 8/2010 | Shafer |
| 7,831,306 | B2 | 11/2010 | Finch |
| 7,890,166 | B2 | 2/2011 | Heruth |
| 7,894,913 | B2 | 2/2011 | Boggs |
| 7,899,553 | B2 | 3/2011 | Barker |
| 7,930,030 | B2 | 4/2011 | Woods |
| 7,945,331 | B2 | 5/2011 | Vilims |
| 7,949,393 | B2 | 5/2011 | Varrichio |
| 7,979,126 | B2 | 7/2011 | Payne |
| 8,046,075 | B2 | 10/2011 | Rezai |
| 8,066,702 | B2 | 11/2011 | Rittman |
| 8,078,281 | B2 | 12/2011 | Priori |
| 8,086,317 | B2 | 12/2011 | Finch |
| 8,657,765 | B2 | 2/2014 | Asfora |
| 8,670,830 | B2 | 3/2014 | Carlson |
| 8,701,675 | B1 | 4/2014 | Schenker |
| 2005/0261754 | A1 | 11/2005 | Woloszko |
| 2007/0021803 | A1 | 1/2007 | Deem |
| 2010/0010567 | A1 | 1/2010 | Deem |
| 2012/0277839 | A1 | 11/2012 | Kramer |
| 2012/0290059 | A1 | 11/2012 | Bradley |

OTHER PUBLICATIONS

Grill W and Mortimer J T. Stimulus waveforms for selective neural stimulation. IEEE Eng. Med. Biol. 14 (1995): 375-385.

John E. Swett and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295.

James N. Campbell, Richard A. Meyer, Srinivasa N. Raja. Is nociceptor activation by alpha-1 adrenoreceptors the culprit in sympathetically maintained pain? APS Journal 1(Jan. 1992):3-11.

Dawson LF, Phillips JK, Finch PM, Inglis JJ, Drummond PD. Expression of a1-adrenoceptors on peripheral nociceptive neurons. Neuroscience 175(2011):300-314.

Donello JE, Guan Y, Tian M, Cheevers CV, Alcantara M, Cabrera S, Raja SN, Gil DW. A peripheral adrenoceptor-mediated sympathetic mechanism can transform stress-induced analgesia into hyperalgesia. Anesthesiology 114(Jun. 2011):1403-1416.

Ralf Baron and Wilfrid Janig. Sympathetically maintained pain. Chapter 22. pp. 309-320. In: Pain—Current Understanding, Emerging Therapies, and Novel Approaches to Drug Discovery (Chas Bountra , Rajesh Munglani , and William K . Schmidt, eds.) New York : Marcel Dekker, Inc., 2003.

Mick Serpell. The role of the sympathetic nervous system and pain. Anesthesia & Intensive Care Medicine 9(Feb. 2008):75-78.

Verdugo RJ, Ochoa JL 'Sympathetically maintained pain.' I. Phentolamine block questions the concept. Neurology 44(1994):1003-1010.

Mitchell B. Max and Ian Gilron. Sympathetically maintained pain: Has the emperor no clothes? Neurology 52(May 1999): 905-907.

Vaughan G. Macefield. A role for the sympathetic nervous system in sympathetically maintained pain? Clinical Neurophysiology 121(2010): 996-997.

Khasar SG, Green PG, Chou B, Levine JD. Peripheral nociceptive effects of alpha 2-adrenergic receptor agonists in the rat. Neuroscience 66(Feb. 1995):427-432.

K. O. Aley and Jon D. Levine. Multiple receptors involved in peripheral alpha-2, mu, and A1 antinociception, tolerance and withdrawal. The Journal of Neuroscience 17(Feb. 1997):735-744.

Fairbanks CA, Stone LS, Kitto KF, Nguyen HO, Posthumus IJ, Wilcox GL. alpha(2C)-Adrenergic receptors mediate spinal analgesia and adrenergic-opioid synergy. J Pharmacol Exp Ther 300(Jan. 2002):282-290.

Koltzenburg M, McMahon SB. The enigmatic role of the sympathetic nervous system in chronic pain. Trends Pharmacol Sci 12(Nov. 1991):399-402.

Koeda T, Sato J, Kumazawa T, Tsujii Y, Mizumura K. Effects of adrenoceptor antagonists on the cutaneous blood flow increase response to sympathetic nerve stimulation in rats with persistent inflammation. Jpn J Physiol 52(Jun. 2002):521-530.

Bogduk N. The innervation of the lumbar spine. Spine 8(Mar. 1983):286-293.

Yongmin Kim, H. Gunter Zieber, and Frank A. Yang. Uniformity of current density under stimulating electrodes. Critical Reviews in Biomedical Engineering 17(Jun. 1990): 585-619.

Habash RW, Bansal R, Krewski D, Alhafid HT. Thermal therapy, part 1: an introduction to thermal therapy. Crit Rev Biomed Eng 34(Jun. 2006):459-489.

Diederich CJ. Thermal ablation and high-temperature thermal therapy: overview of technology and clinical implementation. Int J Hyperthermia 21(Aug. 2005): 745-753.

Haveman J, Van Der Zee J, Wondergem J, Hoogeveen JF, Hulshof MC. Effects of hyperthermia on the peripheral nervous system: a review. Int J Hyperthermia 20(Apr. 2004):371-391.

Lee RC, Zhang D, Hannig J. Biophysical injury mechanisms in electrical shock trauma. Annu Rev Biomed Eng 2(2000):477-509.

Davalos RV, Mir IL, Rubinsky B. Tissue ablation with irreversible electroporation. Ann Biomed Eng 33(Feb. 2005):223-231.

Rubinsky B. Irreversible electroporation in medicine. Technol Cancer Res Treat 6(Apr. 2007):255-260.

Daniels C, Rubinsky B. Electrical field and temperature model of nonthermal irreversible electroporation in heterogeneous tissues. J Biomech Eng 131(Jul. 2009): 071006, pp. 1-12.

(56) References Cited

OTHER PUBLICATIONS

Davalos RV, Otten DM, Mir LM, Rubinsky B. Electrical impedance tomography for imaging tissue electroporation. IEEE Trans Biomed Eng 51(May 2004):761-767.
Granot Y, Rubinsky B. Methods of optimization of electrical impedance tomography for imaging tissue electroporation. Physiol Meas 28 (Oct. 2007):1135-1147.
Linderholm P, Marescot L, Loke MH, Renaud P. Cell culture imaging using microimpedance tomography. IEEE Trans Biomed Eng 55(Jan. 2008):138-146.
Abbas Pourzaki and Hossein Mirzaee. New high voltage pulse generators. Recent Patents on Electrical Engineering 2(2009):65-76.
David G. Stork and Patrick R. Gill. Lensless ultra-miniature CMOS computational imagers and sensors. pp. 186-191 In: Proceedings, Seventh International Conference on Sensor Technologies and Applications (Sensorcomm 2013), held Aug. 25-31, 2013 in Barcelona, Spain. Red Hook, New York: Curran Associates, Inc., 2013.
Technical data sheet for CSL701/801 series of LEDs from ROHM Semiconductor U.S.A., LLC 2323 Owen Street, Santa Clara, CA 95054.
Technical data sheet for Model DL 7891SX 780nm diode laser from Creative Technology Lasers 180 Alderwood Road, Walnut Creek, CA 94598-1042.
Technical data sheet for Model RLU4116E ultraviolet laser diode from Roithner LaserTechnik GmbH. Wiedner Hauptstrasse 76, Vienna, Austria.
Laser Diode catalog. Roithner LaserTechnik GmbH. Wiedner Hauptstrasse 76, Vienna, Austria. Jun. 26, 2014. pp. 1-119.
Kendric C. Smith. Laser and LED photobiology. Laser Therapy 19.2(2010):72-78.
Philip E. Hockberger. A history of ultraviolet photobiology for humans, animals and microorganisms. Photochemistry and Photobiology, 76(Jun. 2002):561-579.
Rodriguez AL, Stefani FS, de Oliveira Praes CE, Piaceski A, Oliveira MP, Martins P, da Silva VD, Bonorino C, Bauer ME. Effects of ultraviolet radiation on human cutaneous nerve fibres. Cell Prolif 42(Apr. 2009):562-567.
Wondrak GT, Jacobson MK, Jacobson EL. Endogenous UVA-photosensitizers: mediators of skin photodamage and novel targets for skin photoprotection. Photochem Photobiol Sci 5(Feb. 2006):215-237.
Ying-Ying Huang, Aaron C.-H. Chen, James D. Carroll and Michael R. Hamblin. Biphasic dose response in low level light therapy. Dose-Response 7(2009):358-383.
Michael R Hamblin and Tatiana N Demidova. Mechanisms of Low Level Light Therapy. Proc. of SPIE 6140(2006): 614001, pp. 1-12.
Chung H, Dai T, Sharma SK, Huang YY, Carroll JD, Hamblin MR. The nuts and bolts of low-level laser (light) therapy. Ann Biomed Eng 40(Feb. 2012):516-533.
Hashmi JT, Huang YY, Osmani BZ, Sharma SK, Naeser MA, Hamblin MR. Role of low-level laser therapy in neurorehabilitation. PM R 2(12 Suppl 2, 2010):S292-305.
Duke AR, Cayce JM, Malphrus JD, Konrad P, Mahadevan-Jansen A, Jansen ED. Combined optical and electrical stimulation of neural tissue in vivo. J Biomed Opt 14(Jun. 2009):060501, pp. 1-3.
Taryn E. Hill, Geoffrey T. Desmoulin, Christopher J. Hunter. Is vibration truly an injurious stimulus in the human spine? Journal of Biomechanics 42 (2009): 2631-2635.
Widerberg A, Bergman S, Danielsen N, Lundborg G, Dahlin LB. Nerve injury induced by vibration: prevention of the effect of a conditioning lesion by D600, a Ca2+ channel blocker. Occup Environ Med 54(May 1997):312-315.
Desmoulin GT, Yasin NI, Chen DW. Spinal mechanisms of pain control. Clin J Pain 23(2007):576-585.
Lundeberg T, Nordemar R, Ottoson D. Pain alleviation by vibratory stimulation. Pain 20(Jan. 1984):25-44.
Anonymous editor. Vibration therapy for pain. Lancet. Jun. 20, 1992:1513.
ShreHarsha Rao. High-definition haptics: Feel the difference! Texas Instruments Analog Application Journal. 3Q 2012:29-32.
Technical data sheet for WBFK-23990-000 hearing aid receiver from Knowles Electronics (1151 Maplewood Drive, Itasca, IL 60143).
Mead C. Killion. Hearing aid transducers. Chapter 166, In: Encyclopedia of Acoustics, Malcolm J. Croker, ed. New York: John Wiley and Sons, 1997, pp. 1979-1990.
Jorge P. Arenas, and Malcolm J. Crocker. Recent Trends in Porous Sound-Absorbing Materials. Sound & Vibration. Jul. 2010: 12-17.
Guieu R, Tardy-Gervet M, Roll J. Analgesic effects of vibration and transcutaneous electrical nerve stimulation applied separately and simultaneously to patients with chronic pain. Can J Neurol Sci. 18(1991):113-119.
D. N. Franz and A. Iggo. Conduction failure in myelinated and non-myelinated axons at low temperatures. J Physiol 199(Feb. 1968): 319-345.
Basbaum CB. Induced hypothermia in peripheral nerve: electron microscopic and electrophysiological observations. J Neurocytol 2(Feb. 1973):171-187.
Jia J, Pollock M. The pathogenesis of non-freezing cold nerve injury. Observations in the rat. Brain 120 ( Pt Apr. 1997):631-646.
Jia J, Pollock M. Cold nerve injury is enhanced by intermittent cooling. Muscle Nerve 22(Dec. 1999):1644-1652.
Rothman SM. The therapeutic potential of focal cooling for neocortical epilepsy. Neurotherapeutics (Feb. 2009): 251-257.
Patberg WR, Nijmeijer A, Schut JK, Versprille A, Zock JP, Zijlstra WG. Effects of local nerve cooling on conduction in vagal fibres shed light upon respiratory reflexes in the rabbit. Pflugers Arch 421(Feb.-Mar. 1992):280-282.
Ackermann DM, Foldes EL, Bhadra N, Kilgore KL. Nerve conduction block using combined thermoelectric cooling and high frequency electrical stimulation. J Neurosci Methods.193(Jan. 2010): 72-76.
Bell LE. Cooling, heating, generating power, and recovering waste heat with thermoelectric systems. Science 321(5895,2008):1457-1461.
Chen, A. and P.K. Wright. Medical applications of thermoelectrics. Chapter 26, pp. 26.1-26.22 In: Thermoelectrics and Its Energy Harvesting (D.M. Rowe, ed). Boca Raton: CRC Press, 2012.
Technical data sheet for thermoelectric model MPC-D403/4 from Micropelt GmbH. Emmy-Noether Strasse 2, 79110 Freiburg, Germany.
Technical data sheet for model HV14 thin film thermoelectric module from Laird Technologies, 3481 Rider Trail South Earth City, MO.
Technical sheet for model OT08 thermoelectric module from Laird Technologies, 3481 Rider Trail South Earth City, MO.
A.Gross, G. Hwang, B. Huang,H. Yang, N. Ghafouri, H. Kim, C. Uher, M. Kaviany, K. Najafi. High-performance micro scale thermoelectric cooler: an optimized 6-stage cooler. Proceedings of Transducers 2009, Denver, CO, USA, Jun. 21-25, 2009, pp. 2413-2416.
Technical data sheet for PSB-S7 thermistor, Shibaura Electronics USA. 39555 Orchard Hill Place, Suite 600, Novi, MI 48375.
Bedard C, Kröger H, Destexhe A. Modeling extracellular field potentials and the frequency-filtering properties of extracellular space. Biophys J 86(Mar. 2004):1829-1842.
Brown EN, Kass RE, Mitra PP. Multiple neural spike train data analysis: state-of-the-art and future challenges. Nat Neurosci 7(May 2004):456-461.
Simon M Danner, Frank Rattay, Ursula S Hofstoetter, Milan R Dimitrijevic, Karen Minassian. Locomotor rhythm and pattern generating networks of the human lumbar spinal cord: an electrophysiological and computer modeling study. BMC Neuroscience14(Suppl 1, 2013):P274, pp. 1-2.
Liu X, Eschenfelder S, Blenk KH, Jänig W, Häbler H. Spontaneous activity of axotomized afferent neurons after L5 spinal nerve injury in rats. Pain 84(Feb.-Mar. 2000):309-318.
Sekine, M; Yamashita, T; Sakamoto, N; Takebayashi, T; Ishii, S. Mechanosensitive afferent units in the lumbar posterior longitudinal ligament. Poster Session. 47th Annual Meeting, Orthopaedic Research Society, Feb. 25-28, 2001, San Francisco, California.

(56) References Cited

OTHER PUBLICATIONS

Miki K, Oda M, Kamijyo N, Kawahara K, Yoshimoto M. Lumbar sympathetic nerve activity and hindquarter blood flow during REM sleep in rats. J Physiol 557(Pt 1, 2004):261-271.
Rodriguez EE, Hernández-Lemus E, Itzá-Ortiz BA, Jiménez I, Rudomín P. Multichannel detrended fluctuation analysis reveals synchronized patterns of spontaneous spinal activity in anesthetized cats. PLoS One 6(Oct. 2011):e26449, pp. 1-11.
D. Puthankattil Subha, Paul K. Joseph, Rajendra Acharya U, and Choo Min Lim. EEG signal analysis: A survey. J Med Syst 34(2010):195-212.
Brown BH. Electrical impedance tomography (EIT): a review. J Med Eng Technol 27(Mar. 2003):97-108.
Boyle, A., Adler, A. Lionheart, W.R.B. Shape deformation in two-dimensional electrical impedance tomography. IEEE Transactions on Medical Imaging 31(Dec. 2012): 2185-2193.
Consmuller T, Rohlmann A, Weinland D, Druschel C, Duda GN, Taylor WR. Comparative evaluation of a novel measurement tool to assess lumbar spine posture and range of motion. Eur Spine J 21(Nov. 2012):2170-2180.
Consmuller T, Rohlmann A, Weinland D, Druschel C, Duda GN, Taylor WR. Velocity of lordosis angle during spinal flexion and extension. PLoS One 7(Nov. 2012):e50135, pp. 1-7.
Justiz, A M, Cheung, H and Gu, W Y. Electrical conductivity of annulus fibrosus. Poster Session—47th Annual Meeting, Orthopaedic Research Society, Feb. 25-28, 2001, San Francisco, California.
IT'IS Foundation. Anonymous. Tendon/Ligament. Electrical Conductivity Tissue Frequency Chart. Tissue Properties Database. IT'IS Foundation. ETH Zentrum, ETZ. CH-8092 Zurich. Switzerland.
Jackson AR, Travascio F, Gu WY. Effect of mechanical loading on electrical conductivity in human intervertebral disk. J Biomech Eng 131(May 2009):054505: pp. 1-15.
Travascio F, Jackson AR, Brown MD, Gu WY. Relationship between solute transport properties and tissue morphology in human annulus fibrosus. J Orthop Res 27(Dec. 2009):1625-1630.
Richard P. Feynman, Robert B. Leighton, and Matthew Sands. The Feynman Lectures on Physics. Volume II. Addison-Wesley Publ. Co. (Reading MA, 1964), p. 15-15.
Szlavik RB, de Bruin H. The effect of stimulus current pulse width on nerve fiber size recruitment patterns. Med Eng Phys 21(Jun.-Jul. 1999):507-515.
Abhishek Datta, Maged Elwassif, Fortunato Battaglia and Marom Bikson. Transcranial current stimulation focality using disc and ring electrode configurations: FEM analysis. J. Neural Eng. 5 (2008): 163-174.
Li D, Puntillo K, Miaskowski C. A review of objective pain measures for use with critical care adult patients unable to self-report. J Pain 9(2008): 2-10.
Labus JS, Keefe FJ, Jensen MP. Self-reports of pain intensity and direct observations of pain behavior: when are they correlated? Pain 102(Jan.-Feb. 2003):109-124.
Tousignant-Laflamme Y, Rainville P, Marchand S.Establishing a link between heart rate and pain in healthy subjects: a gender effect. J Pain 6(2005): 341-347.
Hamunen K, Kontinen V, Hakala E, Talke P, Paloheimo M, Kalso E. Effect of pain on autonomic nervous system indices derived from photoplethysmography in healthy volunteers. Br J Anaesth 108(May 2012):838-844.
Nir RR, Sinai A, Raz E, Sprecher E, Yamitsky D. Pain assessment by continuous EEG: association between subjective perception of tonic pain and peak frequency of alpha oscillations during stimulation and at rest. Brain Res 1344(2010): 77-86.
Casson A, Yates D, Smith S, Duncan J, Rodriguez-Villegas E. Wearable electroencephalography. What is it, why is it needed, and what does it entail? IEEE Eng Med Biol Mag. 29(Mar. 2010):44-56.
Nikulin W, Kegeles J, Curio G. Miniaturized electroencephalographic scalp electrode for optimal wearing comfort. Clin Neurophysiol 121(Jul. 2010):1007-1014.
Zaslansky R, Sprecher E, Katz Y, Rozenberg B, Hemli JA, Yamitsky D. Pain-evoked potentials: what do they really measure? Electroencephalogr Clin Neurophysiol 100(May 1996):384-391.
Gross J, Schnitzler A, Timmermann L, Ploner M. Gamma oscillations in human primary somatosensory cortex reflect pain perception. PLoS Biol 5(May 2007):e133:1168-1173.
Tor D. Wager, Lauren Y. Atlas, Martin A. Lindquist, Mathieu Roy, Choong-Wan Woo and Ethan Kross. An fMRI-Based Neurologic Signature of Physical Pain. N Engl J Med 368(2013):1388-1397.
Dieter Vaitl. Interoception. Biological Psychology 42 (1996):1-27.
Critchley HD, Wiens S, Rotshtein P, Ohman A, Dolan RJ. Neural systems supporting interoceptive awareness. Nat Neurosci 7(Feb. 2004):189-195.
Craig, A.D. How do you feel? Introception: the sense of the physiological condition of the body. Nat. Rev. Neurosci 3(2002):655-666.
Craig AD. How do you feel—now? The anterior insula and human awareness. Nat Rev Neurosci 10(Jan. 2009):59-70.
Mendes, W. B. Assessing the autonomic nervous system. Chapter 7 In: E. Harmon-Jones and J. Beer (Eds.) Methods in Social Neuroscience. New York: Guilford Press, 2009, pp. 118-147.
G.A. Shaw, A.M. Siegel, G. Zogbi, and T.P. Opar. Warfighter physiological and environmental monitoring: a study for the U.S. Army Research Institute in Environmental Medicine and the Soldier Systems Center. MIT Lincoln Laboratory, Lexington MA. Nov. 1, 2004, pp. 1-141.
U. Rajendra Acharya, K. Paul Joseph, N. Kannathal, Choo Min Lim and Jasjit S. Suri. Heart rate variability: a review. Medical and Biological Engineering and Computing 44(Dec. 2006), 1031-1051.
Boettger S, Puta C, Yeragani VK, Donath L, Müller HJ, Gabriel HH, Bär KJ. Heart rate variability, QT variability, and electrodermal activity during exercise. Med Sci Sports Exerc 42(Mar. 2010):443-448.
Sung-Bin Park, Yeon-Sik Noh, Sung-Jun Park, Hyoung-Ro Yoon. An improved algorithm for respiration signal extraction from electrocardiogram measured by conductive textile electrodes using instantaneous frequency estimation Med Bio Eng Comput 46(2008):147-158.
Marieke van Dooren, J.J.G. (Gert-Jan) de Vries, Joris H. Janssen. Emotional sweating across the body: Comparing 16 different skin conductance measurement locations. Physiology & Behavior 106(2012): 298-304.
Wolfram Boucsein. Electrodermal activity, 2nd Ed., New York: Springer, 2012, pp. 1-618.
Ming-Zher Poh, Nicholas C. Swenson, and Rosalind W. Picard. A wearable sensor for unobtrusive, long-term assessment of electrodermal activity. IEEE Transactions on Biomedical Engieering 57(May 2010):1243-1252.
Ming-Zher Poh, Tobias Loddenkemper, Nicholas C. Swenson, Shubhi Goyal, Joseph R. Madsen and Rosalind W. Picard. Continuous monitoring of electrodermal activity during epileptic seizures using a wearable sensor. 32nd Annual International Conference of the IEEE EMBS, Buenos Aires, Argentina, Aug. 31-Sep. 4, 2010, pp. 4415-4418.
Ming-Zher Poh, Tobias Loddenkemper, Claus Reinsberger, Nicholas C. Swenson, Shubhi Goyal, Mangwe C. Sabtala, Joseph R. Madsen, and Rosalind W. Picard. Convulsive seizure detection using a wrist-worn electrodermal activity and accelerometry biosensor. Epilepsia 53(May 2012):e93-e97.
Granger DN, Senchenkova E. Inflammation and the Microcirculation. Chapter 4. pp. 15-18 in: San Rafael (CA): Morgan & Claypool Life Sciences, 2010.
Espahbodi S, Doré CJ, Humphries KN, Hughes SP. Color Doppler ultrasonography of lumbar artery blood flow in patients with low back pain. Spine (Phila Pa 1976) 38(Apr. 2013):E230-E236.
Cai H, Pettersson H, Rohman H, Larsson SE, Oberg PA. A new single-fibre laser Doppler flowmeter based on digital signalprocessing. Med Eng Phys 18(Jul. 1996):523-528.
H. Cai H. Rohman, S. E. Larsson, P. Å. Öëberg. Laser Doppler flowmetry: characteristics of a modified single-fibre technique. Medical and Biological Engineering and Computing 34(Jan. 1996):2-8.

(56) References Cited

OTHER PUBLICATIONS

Shimpei Kohri, Tsutomu Tajikawa, Kenkichi Ohba. Development of a miniaturized fiber-optic LDV sensor for local blood velocity measurement. Biomedical Engineering Research 2(Mar. 2013):131-138.
Yoshinori Kimura, Masaki Goma, Atsushi Onoe, Eiji Higurashi, and Renshi Sawada. Integrated laser Doppler blood flowmeter designed to enable wafer-level packaging. IEEE Transactions on Biomedical Engineering 57(Aug. 2010): 2026-2033.
Adams MA. Biomechanics of back pain. Acupunct Med 22(Apr. 2004):178-188.
Adams MA, Dolan P. Spine biomechanics. J Biomech 38(Oct. 2005):1972-1983.
Robert J. Kowalski, Lisa A. Ferrara, and Edward C. Benzel. Biomechanics of the Spine. Neurosurg Q 15(Jan. 2005): 42-59.
Lee SH, Derby R, Chen Y, Seo KS, Kim MJ. In vitro measurement of pressure in intervertebral discs and annulus fibrosus with and without annular tears during discography. Spine J 4(Jun. 2004):614-618.
Seo KS, Derby R, Date ES, Lee SH, Kim BJ, Lee CH. In vitro measurement of pressure differences using manometry at various injection speeds during discography. Spine J. 7(Jan. 2007):68-73.
Technical publication about model BMA220 accelerometer (Bosch Sensortec, 1800 W. Central Road Mount Prospect, IL 60056).
Adams MA, McNally DS, Dolan P. "Stress" distributions inside intervertebral discs. J Bone J Surg 78(1996):965-972.
Glos DL, Sauser FE, Papautsky I, Bylski-Austrow DI. Implantable MEMS compressive stress sensors: Design, fabrication and calibration with application to the disc annulus. J Biomech 43(Nov. 2010):2244-2248.
Fernando Alfaro, Lee Weiss, Phil Campbell, Mark Miller and Gary K Fedder. Design of a multi-axis implantable MEMS sensor for intraosseous bone stress monitoring J. Micromech. Microeng. 19(2009):085016, pp. 1-13.
Li H, Wang Z. Intervertebral disc biomechanical analysis using the finite element modeling based on medical images. Comput Med Imaging Graph 30(Jun.-Jul. 2006):363-370.
Dolan P, Adams MA. Recent advances in lumbar spinal mechanics and their significance for modelling. Clin Biomech (Bristol, Avon) 16 (Suppl 1, 2001):S8-S16.
Adams MA, Dolan P. Time-dependent changes in the lumbar spine's resistance to bending. Clin Biomech 11(Apr. 1996):194-200.
Z. Ladin and K. M. Neff. Testing of a Biomechanical Model of the Lumbar Muscle Force Distribution Using Quasi-Static Loading Exercises. J Biomech Eng 114(Apr. 1992): 442-449.
Panjabi MM. A hypothesis of chronic back pain: ligament subfailure injuries lead to muscle control dysfunction. Eur Spine J 15(May 2006):668-676.
Roland MO A critical review of the evidence for a pain-spasm-pain cycle in spinal disorders. Clin Biomech (Bristol, Avon) 1(1986):102-109.
Cassisi JE, Sexton-Radek K, Castrogiovanni M, Chastain D, Robinson ME. The use of ambulatory EMG monitoring to measure compliance with lumbar strengthening exercise. Biofeedback Self Regul 18(Jan. 1993):45-52.
Dolan P, Earley M, Adams MA. Bending and compressive stresses acting on the lumbar spine during lifting activities. J Biomech 27(Oct. 1994):1237-1248.
Dag Grini. RF Basics, RF for Non-RF Engineers. Texas Instruments, Post Office Box 655303, Dallas, Texas 75265, 2006.
Knight RT, Scabini D. Anatomic bases of event-related potentials and their relationship to novelty detection in humans. J Clin Neurophysiol 15(Jan. 1998):3-13.
Kececi H, Degirmenci Y, Atakay S. Habituation and dishabituation of P300. Cogn Behav Neurol 19(Mar. 2006):130-134.
William R. Goff. Human average evoked potentials: procedures for stimulating and recording. Chapter 3, pp. 101-156 in: Bioelectric Recording Techniques. Part B. Electroencephalography and Human Brain Potentials (Richard F. Thompson and Michele M. Patterson, eds). New York: Academic Press, 1974.
David Regan. Human Brain Electrophysiology. Evoked potentials and evoked magnetic fields in science and medicine. New York: Elsevier Science Publishing Co., 1989, pp. 1-672.
Terence W. Picton, Otavio G. Lins and Michael Scherg. The recording and analysis of event-related potentials. Chapter 1 (pp. 3-73) in Handbook of Neuropsychology, vol. 10 (F. Boller and J. Grafman, eds). Amsterdam: Elsevier Science B.V., 1995.
Monica Fabiani, Gabriele Gratton and Michael G.H. Coles. Event Related Potentials. Methods, Theory, and Applications. Chapter 3, pp. 53-84 In: John T. Cacioppo, Louis G. Tassinary and Gary G. Berntson (eds). Handbook of Psychophysiology, 2nd Ed. Cambridge: Cambridge University Press, 2000.
Steven J. Luck. An introduction to event-related potentials and their neural origins. Chapter 1 (pp. 1-50) in: Steven J. Luck. An Introduction to the Event-Related Potential Technique. Cambridge, Mass. : MIT Press, 2005.
Todd C. Handy (ed). Event-related Potentials: A Methods Handbook. Camridge, Mass.: MIT Press, 2005, pp. 1-380.
Steven J Luck and Emily S Kappenman, eds. Oxford handbook of event-related potential components. Oxford : Oxford University Press, 2012, pp. 1-626.
Press, WH, Teukolsky, SA, Vetterling, WT, Flannery, BP. Section 16.5. Support Vector Machines. In: Numerical Recipes: The Art of Scientific Computing (3rd ed.). New York: Cambridge University Press, 2007.
Christopher J.C. Burges. A tutorial on support vector machines for pattern recognition. Data Mining and Knowledge Discovery 2(1998): 121-167.
J.A.K. Suykens , J. Vandewalle , B. De Moor. Optimal Control by Least Squares Support Vector Machines. Neural Networks 14 (2001):23-35.
Sapankevych, N.and Sankar, R. Time Series Prediction Using Support Vector Machines: A Survey. IEEE Computational Intelligence Magazine 4(Feb. 2009): 24-38.
Alex J. Smola and Bernhard Scholkopf. A tutorial on support vector regression. Journal of Statistics and Computing 14(Mar. 2004):199-222.
Felipe Alonso-Atienza, José Luis Rojo-Álvarez, Alfredo Rosado-Muñoz, Juan J. Vinagre, Arcadi García-Alberola, Gustavo Camps-Valls. Feature selection using support vector machines and bootstrap methods for ventricular fibrillation detection. Expert Systems with Applications 39(2012): 1956-1967.
Stanslanski S, Afshar P, Cong P, Giftakis J, Stypulkowski P, Carlson D, Linde D, Ullestad D, Avestruz AT, Denison T. Design and validation of a fully implantable, chronic, closed-loop neuromodulation device with concurrent sensing and stimulation. IEEE Trans Neural Syst Rehabil Eng 20(Apr. 2012):410-421.
Humzah MD, Soames RW. Human intervertebral disc: structure and function. Anat Rec 220(Apr. 1988):337-356.
David W.L Hukins and Judith R. Meakin. Relationship between structure and mechanical function of the tissues of the intervertebral joint. Amer. Zool. 40(2000):42-52.
Panjabi MM. Clinical spinal instability and low back pain. J Electromyogr Kinesiol 13(Apr. 2003):371-379.
Joji Inamasu, Bernard H. Guiot and Donald C. Sachs. Ossification of the Posterior Longitudinal Ligament: An Update on Its Biology, Epidemiology, and Natural History. Neurosurgery 58(Jun. 2006): 1027-1039.
Beatty RA, Sugar O, Fox TA. Protrusion of the posterior longitudinal ligament simulating herniated lumbar intervertebral disc. J Neurol Neurosurg Psychiatry 31(Jan. 1968):61-66.
J.D. Stewart Cauda equina disorders. Chapter 6, pp. 63-74. In: Neurologic Bladder, Bowel and Sexual Dysfunction (Clare J Fowler et al, eds) Amsterdam: Elsevier Science, 2001.
Edgar MA. The nerve supply of the lumbar intervertebral disc. J Bone Joint Surg Br 89(Sep. 2007):1135-1139.
J. Randy Jinkins. The anatomic and physiologic basis of local, referred, and radiating lumbosacral pain syndromes related to disease of the spine. J Neuroradiol 31(2004): 163-180.
Bogduk N, Tynan W, Wilson AS. The nerve supply to the human lumbar intervertebral discs. J Anat 132(Jan. 1981):39-56.

(56) References Cited

OTHER PUBLICATIONS

Kojima Y, Maeda T, Arai R, Shichikawa K. Nerve supply to the posterior longitudinal ligament and the intervertebral disc of the rat vertebral column as studied by acetylcholinesterase histochemistry. I. Distribution in the lumbar region. J Anat 169(1990):237-246.

J. H. Mulligan. The innervation of the ligaments attached to the bodies of the vertebrae. J Anat 91(Apr. 1957): 455-465.

Devon I Rubin. Epidemiology and risk factors for spine pain. Neurol Clin 25(2007): 353-371.

Manchikanti L, Singh V, Datta S, Cohen SP, Hirsch JA; American Society of Interventional Pain Physicians. Comprehensive review of epidemiology, scope, and impact of spinal pain. Pain Physician 12(Apr. 2009):E35-E70.

Atlas SJ, Deyo RA. Evaluating and managing acute low back pain in the primary care setting. J Gen Intern Med 16(Feb. 2001):120-131.

Michael Devereaux. Low back pain. Med Clin N America 93(2009):477-501.

Michelle Lin. Musculoskeletal Back Pain. Chapter 51, pp. 591-603. In: Rosen's Emergency Medicine: Concepts and Clinical Practice, 7th edition (Marx JA, Hockberger RS, Walls RM, et al, eds). Philadelphia: Mosby Elsevier, 2009.

Last AR, Hulbert K. Chronic low back pain: evaluation and management. Am Fam Physician 79(Dec. 2009):1067-1074.

McCamey K, Evans P. Low back pain. Prim Care 34(Jan. 2007):71-82.

Chou R, Qaseem A, Snow V, Casey D, Cross JT Jr, Shekelle P, Owens DK; Clinical Efficacy Assessment Subcommittee of the American College of Physicians; American College of Physicians; American Pain Society Low Back Pain Guidelines Panel. Diagnosis and treatment of low back pain: a joint clinical practice guideline from the American College of Physicians and the American Pain Society. Ann Intern Med 147(Jul. 2007): 478-491.

Kallewaard JW, Terheggen MA, Groen GJ, Sluijter ME, Derby R, Kapural L, Mekhail N, van Kleef M. (15.) Discogenic low back pain. Pain Practice 10(Jun. 2010):560-579.

Keith D. Williams and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007.

Audette JF, Emenike E, Meleger AL. Neuropathic low back pain. Curr Pain Headache Rep 9(Mar. 2005):168-177.

Hurri H, Karppinen J. Discogenic pain. Pain 112(Mar. 2004):225-228.

Freemont AJ, Peacock TE, Goupille P, Hoyland JA, O'Brien J, Jayson MI. Nerve ingrowth into diseased intervertebral disc in chronic back pain. Lancet 350(9072,1997):178-181.

Martin MD, Boxell CM, Malone DG. Pathophysiology of lumbar disc degeneration: a review of the literature. Neurosurg Focus 13(Feb. 2002):Article 1, pp. 1-6.

Peng B, Wu W, Hou S, Li P, Zhang C, Yang Y. The pathogenesis of discogenic low back pain. J Bone Joint Surg Br 87(Jan. 2005): 62-67.

Y. Aoki, K. K Takahashi, S. Ohtori & H. Moriya: Neuropathology of Discogenic Low Back Pain: A Review. The Internet Journal of Spine Surgery 2 (Jan. 2005): 1-9.

Walker MH, Anderson DG. Molecular basis of intervertebral disc degeneration. Spine J 4(6 Suppl, 2004):158S-166S.

Boswell MV, et al. Interventional techniques: evidence-based practice guidelines in the management of chronic spinal pain. Pain Physician 10(Jan. 2007):7-111.

Seaman DR, Cleveland C 3rd. Spinal pain syndromes: nociceptive, neuropathic, and psychologic mechanisms. J Manipulative Physiol Ther 22(Jul. 1999):458-472.

Nakamura SI, Takahashi K, Takahashi Y, Yamagata M, Moriya H. The afferent pathways of discogenic low-back pain. Evaluation of L2 spinal nerve infiltration. J Bone Joint Surg Br 78(Apr. 1996):606-612.

Takebayashi T, Cavanaugh JM, Kallakuri S, Chen C, Yamashita T. Sympathetic afferent units from lumbar intervertebral discs. J Bone Joint Surg Br 88(Apr. 2006):554-557.

Tomecek FJ, Anthony CS, Boxell C, Warren J. Discography interpretation and techniques in the lumbar spine. Neurosurg Focus 13(Feb. 2002):Article 13, pp. 1-8.

Zhang YG, Guo TM, Guo X, Wu SX. Clinical diagnosis for discogenic low back pain. Int J Biol Sci 5(Jul. 2009):647-658.

Manchikanti L, Singh V, Pampati V, Damron KS, Barnhill RC, Beyer C, Cash KA. Evaluation of the relative contributions of various structures in chronic low back pain. Pain Physician 4(Apr. 2001):308-316.

Kinkade S. Evaluation and treatment of acute low back pain. Am Fam Physician 75(Aug. 2007):1181-1188.

Brian S Williams and Paul J Christo. Pharmacological and interventional treatments for neuropathic pain. Chapter 12 pp. 295-375. In: Mechanisms of Pain in Peripheral Neuropathy (M Dobretsov and J-M Zhang, eds). Trivandrum, India: Research Signpost, 2009.

Chou R, Huffman LH; American Pain Society; American College of Physicians. Nonpharmacologic therapies for acute and chronic low back pain: a review of the evidence for an American Pain Society/American College of Physicians clinical practice guideline. Ann Intern Med 147(Jul. 2007): 492-504.

Lavelle WF, Lavelle ED, Smith HS. Interventional techniques for back pain. Clin Geriatr Med 24(Feb. 2008):345-68.

Derby R, Eek B, Chen Y, O'neill C, Ryan D. Intradiscal Electrothermal Annuloplasty (IDET): A Novel Approach for Treating Chronic Discogenic Back Pain. Neuromodulation 3(Feb. 2000):82-88.

Helm S, Hayek SM, Benyamin RM, Manchikanti L. Systematic review of the effectiveness of thermal annular procedures in treating discogenic low back pain. Pain Physician 12(Jan. 2009):207-232.

Chou R, Baisden J, Carragee EJ, Resnick DK, Shaffer WO, Loeser JD. Surgery for low back pain: a review of the evidence for an American Pain Society Clinical Practice Guideline. Spine 34(Oct. 2009):1094-1109.

Lavelle W, Carl A, Lavelle ED. Invasive and minimally invasive surgical techniques for back pain conditions. Med Clin North Am 91(Feb. 2007):287-298.

Schwender JD, Foley KT, Holly LT, Transfeldt, EE. Minimally Invasive Posterior Surgical Approaches to the Lumbar Spine. Chapter 21, pp. 333-341 In: The Spine, Fifth Edition (Harry N. Herkowitz, Richard A. Balderston, Steven R. Garfin, Frank J. Eismont, eds). Philadelphia: Saunders/Elsevier, 2006.

Griffith SL, Davis RJ, Hutton WC. Repair of the Anulus Fibrosus of the Lumbar Disc. Chapter 12 (pp. 41-48), In: Nucleus Arthroplasty Technology in Spinal Care: vol. II—Biomechanics & Development. Davis R, Cammisa FP, Girardi FP, Hutton WC, Editors. Bloomington, MN: Raymedica Co, 2007.

Ten Vaarwerk IA, Staal MJ. Spinal cord stimulation in chronic pain syndromes. Spinal Cord 36(Oct. 1998):671-682.

North RB, Wetzel FT. Spinal cord stimulation for chronic pain of spinal origin: a valuable long-term solution. Spine 27(Feb. 2002):2584-2591.

Stojanovic MP, Abdi S. Spinal cord stimulation. Pain Physician 5(Feb. 2002):156-166.

Barolat G, Sharan A. Spinal Cord Stimulation for Chronic Pain Management. In Pain Management for the Neurosurgeon: Part 2, Seminars in Neurosurgery 15 (Feb. 2004):151-175.

R.B. North. Neural interface devices: spinal cord stimulation technology. Proceedings of the IEEE 96(Jul. 2008): 1108-1119.

R. Mark Richardson. Closing the Loop in Neuromodulation: Concurrent Sensing and Stimulation. Neurosurgery 71(Feb. 2012): N19-N20.

Afshar P, Khambhati A, Stanslaski S, Carlson D, Jensen R, Linde D, Dani S, Lazarewicz M, Cong P, Giftakis J, Stypulkowski P, Denison T. A translational platform for prototyping closed-loop neuromodulation systems. Front Neural Circuits 6(2013):117, pp. 1-15.

Karl Johan Astrom & Richard M. Murray. Feedback Systems: An Introduction for Scientists and Engineers. Princeton NJ: Princeton University Press, 2008, pp. 1-396.

(56) References Cited

OTHER PUBLICATIONS

Torkel Glad and Lennart Ljung. Control Theory. Multivariable and Nonlinear Methods. New York: Taylor and Francis, 2000. pp. 1-451.
Zdzislaw Bubnicki. Modern Control Theory. Berlin: Springer, 2005. pp. 1-419.
Coleman Brosilow, Babu Joseph. Feedforward Control (Chapter 9) In: Techniques of Model-Based Control by Coleman Brosilow; Babu Joseph. Upper Saddle River, N.J.: Prentice Hall PTR, 2002. pp. 221-240.
Dubin AE, Patapoutian A. Nociceptors: the sensors of the pain pathway. J Clin Invest 120(Nov. 2010):3760-3772.
Chen CL, Broom DC, Liu Y, de Nooij JC, Li Z, Cen C, Samad OA, Jessell TM, Woolf CJ, Ma Q. Runx1 determines nociceptive sensory neuron phenotype and is required for thermal and neuropathic pain. Neuron 49(Mar. 2006):365-377.
Scherrer G, Low SA, Wang X, Zhang J, Yamanaka H, Urban R, Solorzano C, Harper B, Hnasko TS, Edwards RH, Basbaum Al. VGLUT2 expression in primary afferent neurons is essential for normal acute pain and injury-induced heat hypersensitivity. Proc Natl Acad Sci U S A 107(51,2010):22296-22301.
Delmas P, Hao J, Rodat-Despoix L. Molecular mechanisms of mechanotransduction in mammalian sensory neurons. Nat Rev Neurosci.12(Mar. 2011):139-153.
Chen CS. Mechanotransduction—a field pulling together? J Cell Sci 121(Pt 20,2008):3285-3292.
Abraira VE, Ginty DD. The sensory neurons of touch. Neuron 79(Apr. 2013):618-639.
Hu J, Milenkovic N, Lewin GR. The high threshold mechanotransducer: a status report. Pain 120(Jan.-Feb. 2006):3-7.
Xiao R, Xu XZ. Mechanosensitive channels: in touch with Piezo. Curr Biol 20(21,2010):R936-R938.
Hao J, Delmas P. Multiple desensitization mechanisms of mechanotransducer channels shape firing of mechanosensory neurons. J Neurosci 30(40,2010):13384-13395.
Matthew Silver and Kranthi Vistakula. Piezoelectric Proteins. pp. 15-20 in Bio-electric Space Exploration. Final Report of May 2007 for NASA Institute for Advanced Concepts Phase I Grant (CP 06-01). pp. 1-108. IntAct Labs LLC (now Cambrian Innovation) 27 Drydock Avenue Floor 2 Boston, MA 02210.
Eiichi Fukada. Piezoelectric effects in collagen. Japanese Journal of Applied Physics 3(Feb. 1864):117-121.
Ahn AC, Grodzinsky AJ. Relevance of collagen piezoelectricity to "Wolff's Law": a critical review. Med Eng Phys 31(Jul. 2009):733-741.
Minary-Jolandan M, Yu MF. Nanoscale characterization of isolated individual type I collagen fibrils: polarization and piezoelectricity. Nanotechnology20(Aug. 2009):085706, pp. 1-6.
West CR, Bowden AE. Using tendon inherent electric properties to consistently track induced mechanical strain. Ann Biomed Eng 40(Jul. 2012):1568-1574.
Felder CE, Prilusky J, Silman I, Sussman JL. A server and database for dipole moments of proteins. Nucleic Acids Res 35(Web Server issue,2007):W512-W521.
Funk RH, Monsees T, Ozkucur N. Electromagnetic effects—From cell biology to medicine. Prog Histochem Cytochem 43(Apr. 2009):177-264.
J.A. Brown and J.A. Tuszynski. Dipole interactions in axonal microtubules as a mechanism of signal propagation. Physical Review E 56(May 1997):5834-5840.
Steffan Wall. The history of electrokinetic phenomena. Current Opinion in Colloid & Interface Science 15(2010):119-124.
Frank EH, Grodzinsky AJ. Cartilage electromechanics—I. Electrokinetic transduction and the effects of electrolyte pH and ionic strength. J Biomech 20(Jun. 1987):615-627.
Chih-Tung Chen. An investigation of the interstitial fluid flow and electromechanical properties of ligaments and tendons. The University of Wisconsin—Madison, ProQuest, UMI Dissertations Publishing, 1996. 9634170. pp. 1-165.

Butler SL, Kohles SS, Thielke RJ, Chen C, Vanderby R Jr. Interstitial fluid flow in tendons or ligaments: a porous medium finite element simulation. Med Biol Eng Comput 35(Jun. 1997):742-746.
Allen W. Burton, Phillip C. Phan. Spinal Cord Stimulation for Pain Management. Chapter 7, pp. 7-1 to 7-16, In: Neuroengineering (Daniel J. DiLorenzo and Joseph D. Bronzino, eds). Boca Raton: CRC Press, 2008.
Steven Falowski, Amanda Celii, and Ashwini Sharan. Spinal cord stimulation: an update. Neurotherapeutics 5(Jan. 2008):86-99.
Kunnumpurath S, Srinivasagopalan R, Vadivelu N. Spinal cord stimulation: principles of past, present and future practice: a review. J Clin Monit Comput 23(May 2009):333-339.
White PF, Li S, Chiu JW. Electroanalgesia: its role in acute and chronic pain management. Anesth Analg 92(Feb. 2001):505-513.
Stanton-Hicks M, Salamon J. Stimulation of the central and peripheral nervous system for the control of pain. J Clin Neurophysiol 14(Jan. 1997):46-62.
John C. Oakley. Spinal Cord Stimulation in Axial Low Back Pain: Solving the Dilemma. Pain Medicine 7 (Supplement s1,2006):S58-S63.
Danner SM, Hofstoetter US, Ladenbauer J, Rattay F, Minassian K. Can the human lumbar posterior columns be stimulated by transcutaneous spinal cord stimulation? A modeling study. Artif Organs 35(Mar. 2011):257-262.
Shealy CN, Mortimer JT, Reswick JB. Electrical inhibition of pain by stimulation of the dorsal columns: preliminary clinical report. Anesth Analg 46(Apr. 1967):489-491.
Sanford J. Larson, Anthony Sances, Joseph F. Cusick, Glenn A. Meyer, Thomas Swiontek. A comparison between anterior and posterior spinal implant systems. Surg. Neurol. 4(1975):180-186.
Reuben Hoppenstein. Electrical stimulation of the ventral and dorsal columns of the spinal cord for relief of chronic intractable pain: preliminary report. Surg. Neurol. 4(1975):187-194.
Mark A. Harrast. Epidural steroid injections for lumbar spinal stenosis. Curr Rev Musculoskelet Med 1:(2008):32-38.
Barolat G, Massaro F, He J, Zeme S, Ketcik B. Mapping of sensory responses to epidural stimulation of the intraspinal neural structures in man. J Neurosurg 78(Feb. 1993):233-239.
Mailis_Gagnon A, Furlan AD, Sandoval JA, Taylor R. Spinal cord stimulation for chronic pain. Cochrane Database Syst Rev. 2004;(3):CD003783,pp. 1-16, updated 2009.
Eldabe S, Kumar K, Buchser E, Taylor RS. An analysis of the components of pain, function, and health-related quality of life in patients with failed back surgery syndrome treated with spinal cord stimulation or conventional medical management. Neuromodulation 13(Mar. 2010):201-209.
Frey ME, Manchikanti L, Benyamin RM, Schultz DM, Smith HS, Cohen SP. Spinal cord stimulation for patients with failed back surgery syndrome: a systematic review. Pain Physician 12(Feb. 2009):379-397.
Vallejo R, Manuel Zevallos L, Lowe J, Benyamin R. Is Spinal Cord Stimulation an Effective Treatment Option for Discogenic Pain? Pain Pract 12(Mar. 2012):194-201.
Adnan Al-Kaisy, Iris Smet, and Jean-Pierre Van Buyten. Analgesia of axial low back pain with novel spinal neuromodulation. Poster presentation #202 at the 2011 meeting of the American Academy of Pain Medicine, held in National Harbor, MD, Mar. 24-27, 2011.
Kuslich SD, Ulstrom CL, Michael CJ. The tissue origin of low back pain and sciatica: a report of pain response to tissue stimulation during operations on the lumbar spine using local anesthesia. Orthop Clin North Am 22(Feb. 1991):181-187.
Maertens de Noordhout A, Rothwell JC, Thompson PD, Day BL, Marsden CD. Percutaneous electrical stimulation of lumbosacral roots in man. J Neurol Neurosurg Psychiatry 51(Feb. 1988):174-181.
Kothbauer KF, Deletis V. Intraoperative neurophysiology of the conus medullaris and cauda equina. Childs Nery Syst 26(Feb. 2010):247-253.
Johnson BA, Schellhas KP, Pollei SR. Epidurography and therapeutic epidural injections: technical considerations and experience with 5334 cases. AJNR Am J Neuroradiol 20(Apr. 1999):697-705.
I.S. Lee, S.H. Kim, J.W. Lee, S.H. Hong, J.-Y. Choi, H.S. Kang, J.W. Song, and A.K. Kwon. Comparison of the temporary diagnostic relief of transforaminal epidural steroid injection approaches: conventional versus posterolateral technique. American Journal of Neuroradiology 28(2007): 204-208.

(56) References Cited

OTHER PUBLICATIONS

Thomas N. Pajewski, Vincent Arlet and Lawrence H. Phillips. Current approach on spinal cord monitoring: the point of view of the neurologist, the anesthesiologist and the spine surgeon Eur Spine J 16(Suppl 2,2007): 115-129.

Malhotra, Neil R and Shaffrey, Christopher I. Intraoperative electrophysiological monitoring in spine surgery. Spine 35(25,2010):2167-2179.

North RB, Kidd DH, Olin JC, Sieracki JM. Spinal cord stimulation electrode design: prospective, randomized, controlled trial comparing percutaneous and laminectomy electrodes—part I: technical outcomes. Neurosurgery 51(Feb. 2002):381-389.

Pearcy MJ, Tibrewal SB. Lumbar intervertebral disc and ligament deformations measured in vivo. Clin Orthop Relat Res (191,1984):281-286.

MacDonald JD, Fisher KJ. Technique for steering spinal cord stimulator electrode. Neurosurgery 69(1 Suppl Operative, 2011):ons83-86.

A.R. Liboff. Signal shapes in electromagnetic therapies: a primer. pp. 17-37 in: Bioelectromagnetic Medicine (Paul J. Rosch and Marko S. Markov, eds.). New York: Marcel Dekker (2004).

De Vos CC, Hilgerink MP, Buschman HP, Holsheimer J. Electrode contact configuration and energy consumption in spinal cord stimulation. Neurosurgery 65(6 Suppl,2009):210-6.

Holsheimer J. Computer modelling of spinal cord stimulation and its contribution to therapeutic efficacy. Spinal Cord 36(Aug. 1998):531-540.

Gu WY, Justiz MA, Yao H. Electrical conductivity of lumbar annulus fibrosus: effects of porosity and fixed charge density. Spine 27(21,2002):2390-2395.

Lee D, Hershey B, Bradley K, Yearwood T. Predicted effects of pulse width programming in spinal cord stimulation: a mathematical modeling study. Med Biot Eng Comput 49(Jul. 2011):765-774.

Manola L, Holsheimer J, Veltink PH, Bradley K, Peterson D. Theoretical investigation into longitudinal cathodal field steering in spinal cord stimulation. Neuromodulation (Feb. 2007):120-132.

Sekine M, Yamashita T, Takebayashi T, Sakamoto N, Minaki Y, Ishii S. Mechanosensitive afferent units in the lumbar posterior longitudinal ligament. Spine26(14,2001): 1516-1521.

Coppes MH, Marani E, Thomeer RT, Groen GJ. Innervation of "painful" lumbar discs. Spine 22(20,1997):2342-2349.

von During M, Fricke B, Dahlmann A. Topography and distribution of nerve fibers in the posterior longitudinal ligament of the rat: an immunocytochemical and electron-microscopical study. Cell Tissue Res 281(Feb. 1995):325-338.

McCarthy PW, Petts P, Hamilton A. RT97- and calcitonin gene-related peptide-like immunoreactivity in lumbar intervertebral discs and adjacent tissue from the rat. J Anat 180 (Jan. 1992):15-24.

Ahmed M, Bjurholm A, Kreicbergs A, Schultzberg M. Neuropeptide Y, tyrosine hydroxylase and vasoactive intestinal polypeptide-immunoreactive nerve fibers in the vertebral bodies, discs, dura mater, and spinal ligaments of the rat lumbar spine. Spine 18(Feb. 1993):268-273.

Kallakuri S, Cavanaugh JM, Blagoev DC. An immunohistochemical study of innervation of lumbar spinal dura and longitudinal ligaments. Spine 23(Apr. 1998):403-411.

Gronblad M, Weinstein JN, Santavirta S. Immunohistochemical observations on spinal tissue innervation. A review of hypothetical mechanisms of back pain. Acta Orthop Scand 62(Jun. 1991):614-622.

Kuner R. Central mechanisms of pathological pain. Nat Med 16(Nov. 2010):1258-1266.

Schlereth T, Birklein F. The sympathetic nervous system and pain. Neuromolecular Med 10(Mar. 2008):141-147.

Groen GJ, Beget B, Drukker J. Nerves and nerve plexuses of the human vertebral column. Am J Anat 188(Mar. 1990):282-296.

Schott GD. Visceral afferents: their contribution to 'sympathetic dependent' pain. Brain 117 ( Pt 2, 1994):397-413.

Kojima Y, Maeda T, Arai R, Shichikawa K. Nerve supply to the posterior longitudinal ligament and the intervertebral disc of the rat vertebral column as studied by acetylcholinesterase histochemistry. II. Regional differences in the distribution of the nerve fibres and their origins. J Anat 169(1990):247-255.

Nakamura S , Takahashi K, Takahashi Y, Morinaga T, Shimada Y, Moriya H. Origin of nerves supplying the posterior portion of lumbar intervertebral discs in rats. Spine (Phila Pa 1976) 21(Aug. 1996):917-924.

Suseki K, Takahashi Y, Takahashi K, Chiba T, Yamagata M, Moriya H. Sensory nerve fibres from lumbar intervertebral discs pass through rami communicantes. A possible pathway for discogenic low back pain. Bone Joint Surg Br 80(Apr. 1998):737-742.

Shinji Imai, Yrjö T Konttinen, Yoshimitsu Tokunaga, Toshihiro Maeda, Sinsuke Hukuda, Seppo Santavirta. Tyrosine hydroxylase-immunoreactive nerve fibres in rat posterior longitudinal ligament. Journal of the Autonomic Nervous System 63 (Jan.-Feb. 1997): 51-60.

Palmgren T, Gronblad M, Virri J, Seitsalo S, Ruuskanen M, Karaharju E. Immunohistochemical demonstration of sensory and autonomic nerve terminals in herniated lumbar disc tissue. Spine 21(1996):1301-1306.

Palmgren T, Grönblad M, Virri J, Kääpä E, Karaharju E. An immunohistochemical study of nerve structures in the anulus fibrosus of human normal lumbar intervertebral discs. Spine (Phila Pa 1976) 24(20,1999):2075-2079.

Macefield, V., Wallin, B.G. & Vallbo, A.B. 1994. The discharge behaviour of single vasoconstrictor motoneurones in human muscle nerves. J Physiol (Lond) 481 (1994):799-809.

Mano, Tadaaki; Iwase, Satoshi; Toma, Shinobu. Microneurography as a tool in clinical neurophysiology to investigate peripheral neural traffic in humans. Clinical Neurophysiology 117 (Nov. 2006): 2357-2384.

Åke B. Vallbo, Karl-Erik Hagbarth and B. Gunnar Wallin. Microneurography: how the technique developed and its role in the investigation of the sympathetic nervous system. J Appl Physiol 96 (2004):1262-1269.

Mark AL, Wallin BG. Microneurography: a technique for assessing central neural effects of adrenergic drugs on sympathetic outflow in humans.J Cardiovasc Pharmacol. 7 (Suppl 8, 1985):S67-S69.

Valley MA, Bourke DL, McKenzie AM, Raja SN. Quantitative testing of sympathetic function with laser Doppler flowmetry. J Clin Monit. 9 (Apr. 1993):252-256.

Jason J. McDougall, William R. Ferrell and Robert C. Bray. Spatial variation in sympathetic influences on the vasculature of the synovium and medial collateral ligament of the rabbit knee joint. Journal of Physiology 503.2 (1997):435-443.

Murray Esler. The sympathetic nervous system through the ages: from Thomas Willis to resistant hypertension Experimental Physiology 96 (Jul. 2011):611-622.

Jay P. Shah, Terry M. Phillips, Jerome V. Danoff, Lynn H. Gerber. An in vivo microanalytical technique for measuring the local biochemical milieu of human skeletal muscle. Journal of Applied Physiology 99 (May 2005):1977-1984.

Karin Pihel, Timothy J. Schroeder, R. Mark Wightman. Rapid and Selective Cyclic Voltammetric Measurements of Epinephrine and Norepinephrine as a Method to Measure Secretion from Single Bovine Adrenal Medullary Cells. Anal. Chem. 66 (24,1994):4532-4537.

Saad S. M. Hassan, G. A. Rechnitz. New liquid membrane electrode for the determination of ephedrine, epinephrine, and norepinephrine. Anal. Chem. 58 (Jun. 1986):1052-1054.

Kristen E. Secor and Timothy E. Glass. Selective Amine Recognition: Development of a Chemosensor for Dopamine and Norepinephrine. Org. Lett. 6 (21,2004):3727-3730.

Serge Cosnier, Arielle Le Pellec, Robert S. Marks, Karine Périé, Jean-Paul Lellouche. A permselective biotinylated polydicarbazole film for the fabrication of amperometric enzyme electrodes. Electrochemistry Communications 5 (Nov. 2003):973-977.

Grassi G, Esler M. How to assess sympathetic activity in humans. J Hypertens 17 (Jun. 1999):719-734.

Momin A, Cadiou H, Mason A, McNaughton PA. Role of the hyperpolarization-activated current Ih in somatosensory neurons. J Physiol. 586.24(2008):5911-5929.

(56) References Cited

OTHER PUBLICATIONS

Gold MS, Gebhart GF. Nociceptor sensitization in pain pathogenesis. Nat Med. 16 (Nov. 2010):1248-1257.

A. I. Kostyukov, S. V. Lytvynenko, N. V. Bulgakova, and A. V. Gorkovenko. Changes in the Threshold of Generation of Action Potentials by Spinal Motoneurons under Conditions of Their Natural Activation. Neurophysiology 43 (Nov. 3, 2011):211-221.

Randall K. D. B. Powers and Marc D. Binder. Experimental Evaluation of Input-Output Models of Motoneuron Discharge. Journal of Neurophysiology 75(Jan. 1, 1996): 367-379.

Ingber DE. Tensegrity: the architectural basis of cellular mechanotransduction. Annu Rev Physiol 59(1997):575-599.

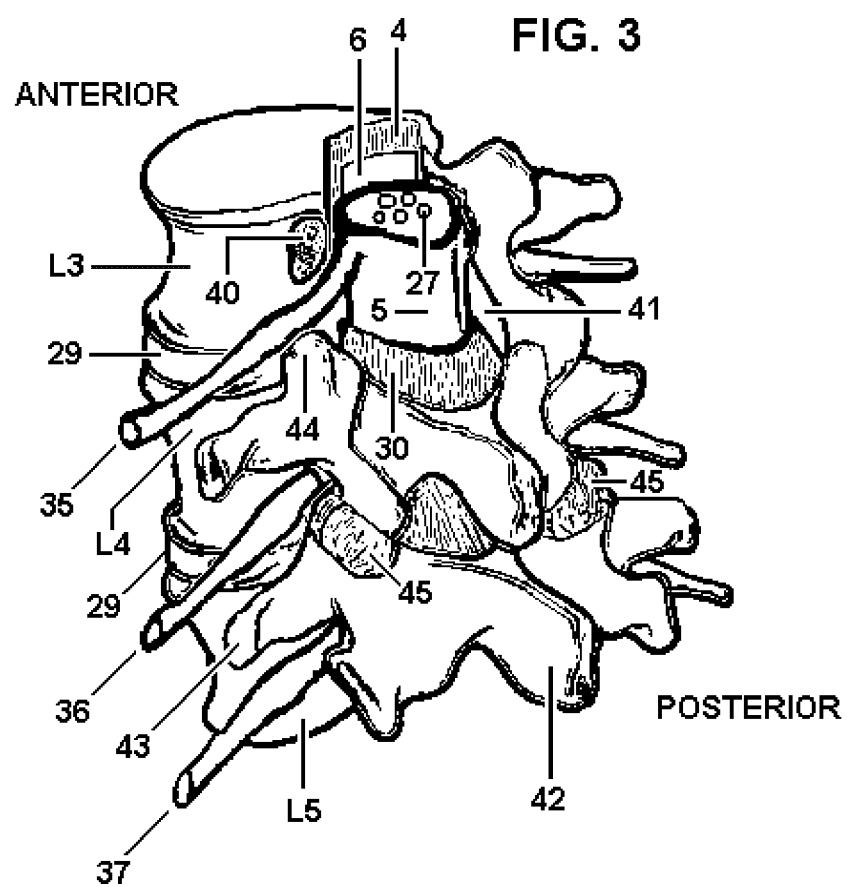

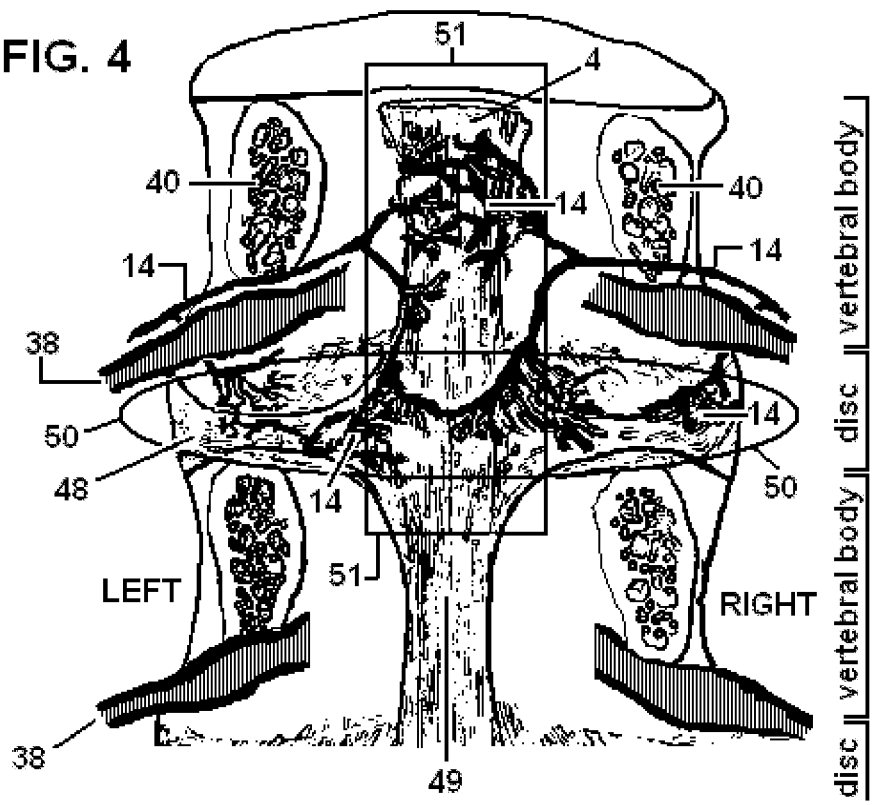

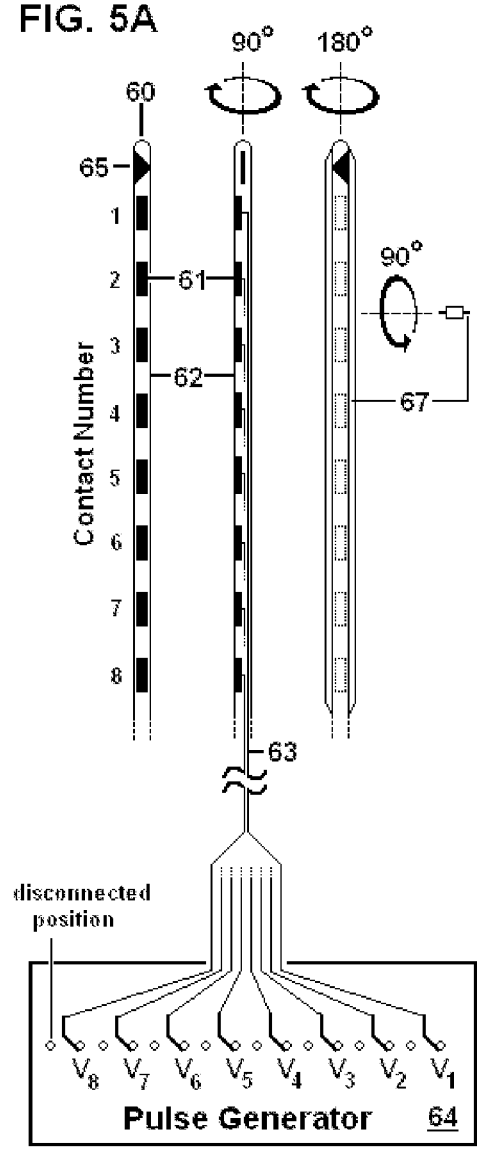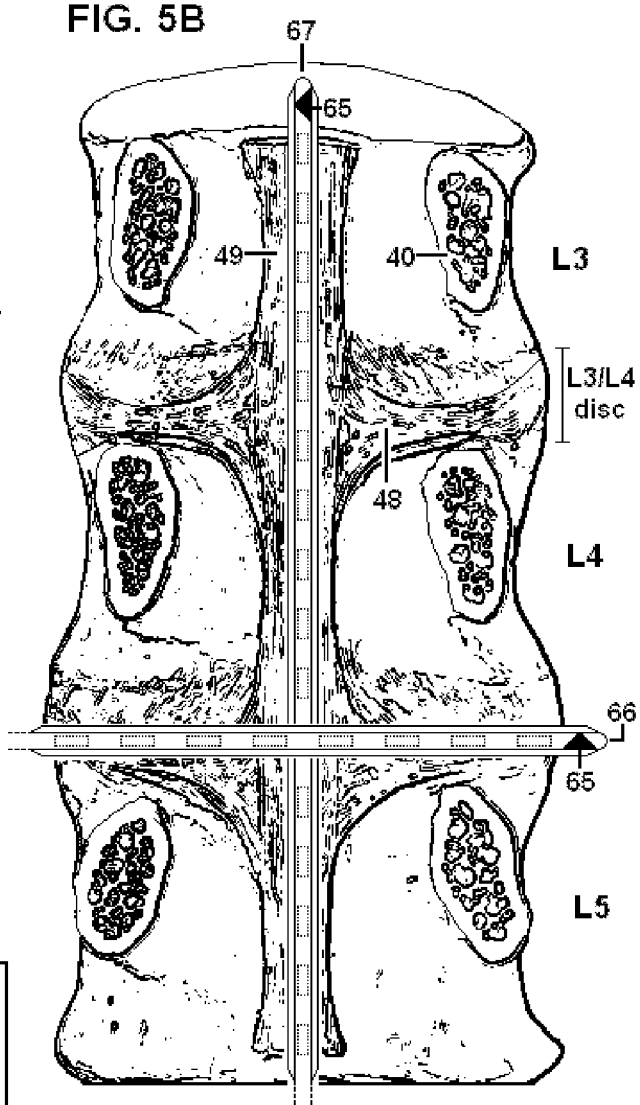

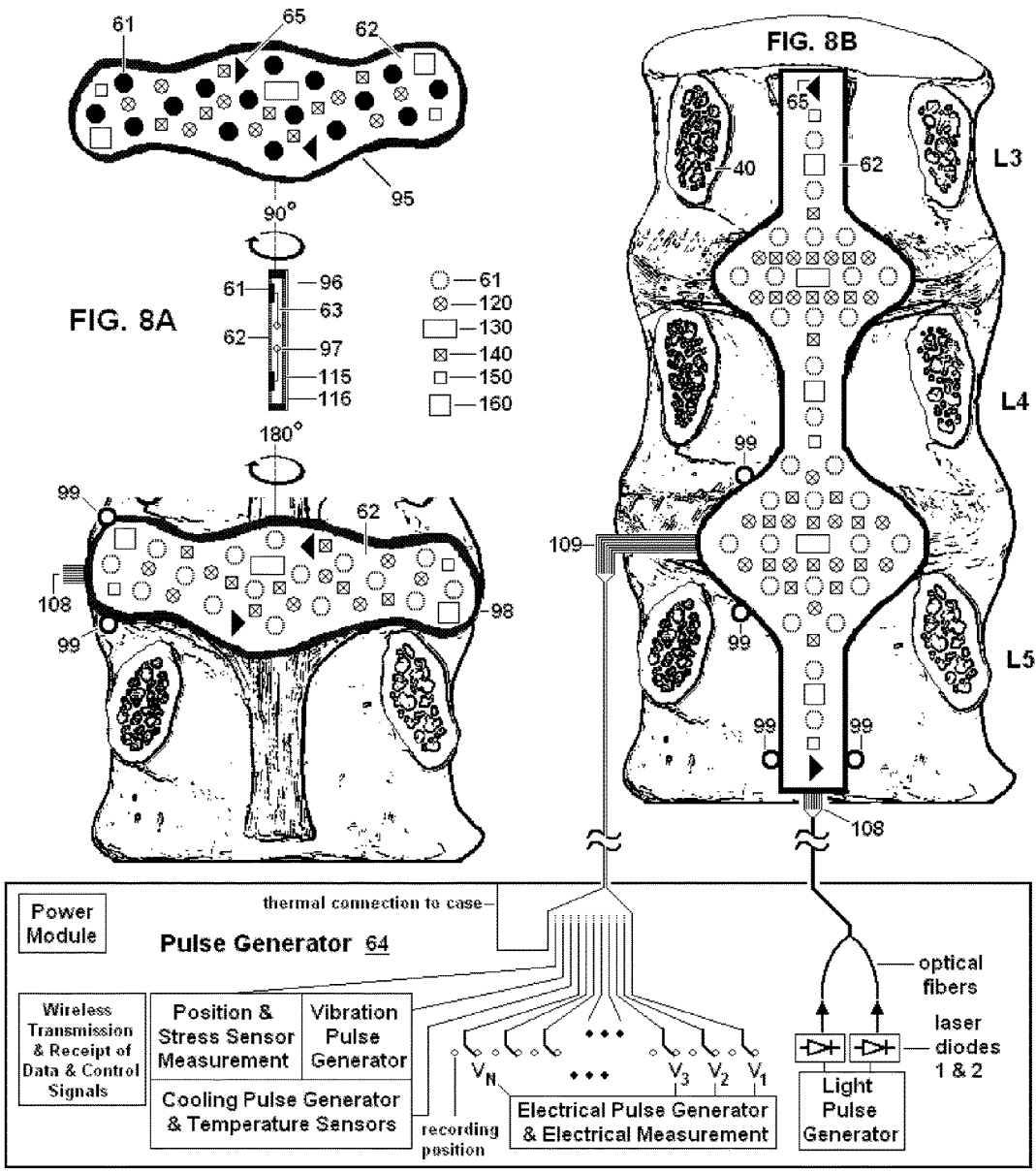

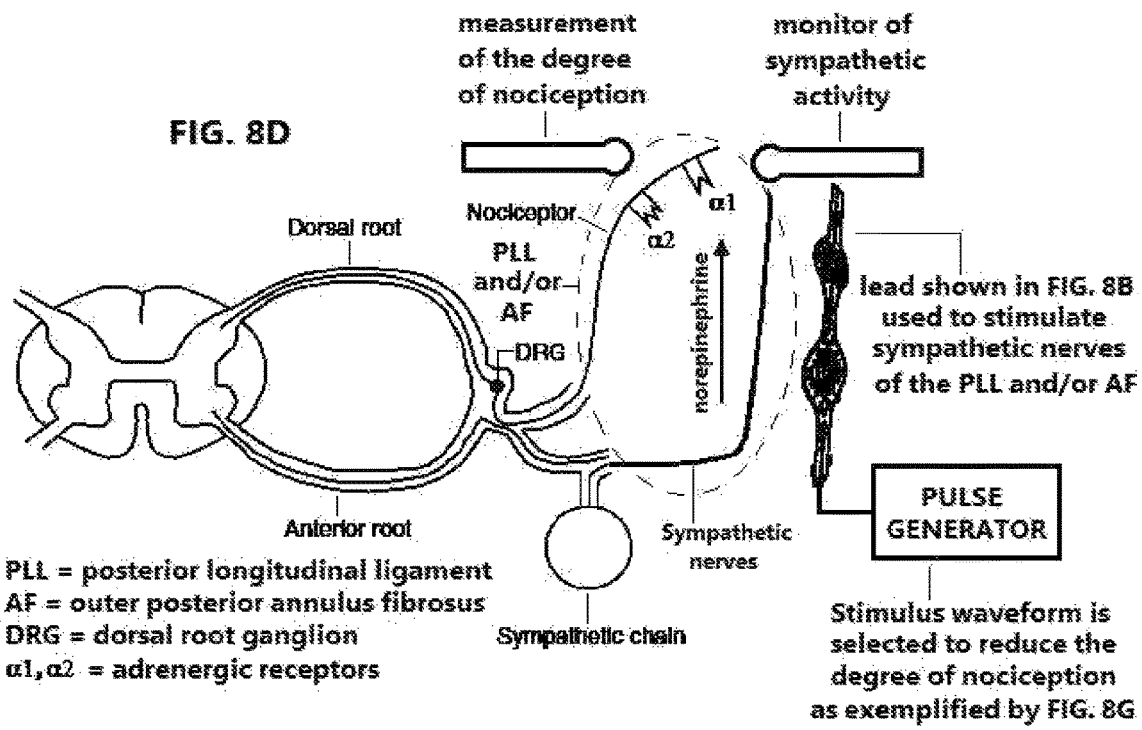
FIG. 8D
PLL = posterior longitudinal ligament
AF = outer posterior annulus fibrosus
DRG = dorsal root ganglion
α1, α2 = adrenergic receptors
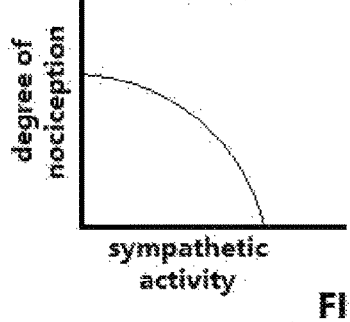
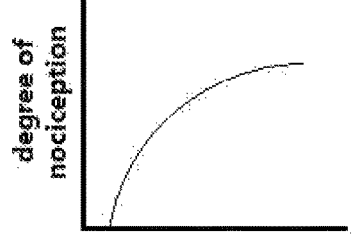
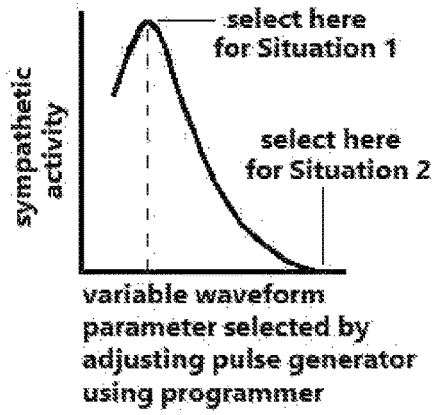

SYSTEM AND METHODS FOR DIAGNOSIS AND TREATMENT OF DISCOGENIC LOWER BACK PAIN

CROSS REFERENCE TO RELATED APPLICATIONS

This is a continuation-in-part of pending application U.S. Ser. No. 13/402,093 having publication No. US 20120215218, now U.S. Pat. No. 8,880,189, which was filed 22 Feb. 2012. This application also claims the benefit of a pending division of that application, U.S. Ser. No. 14/099,910 having publication No. US 20140135876, now U.S. Pat. No. 8,892,215, which was filed 7 Dec. 2013. Those two applications, as well as this application, claim the benefit of provisional patent application No. 61/463,800, entitled System and Method for Electrical Stimulation of the Lumbar Vertebral Column, to J. D. LIPANI, with a filing date of Feb. 23, 2011. These provisional, non-provisional, and divisional applications are herein incorporated by reference for all purposes.

BACKGROUND OF THE INVENTION

The field of the present invention relates to the delivery of energy impulses to bodily tissues for therapeutic purposes. The disclosed methods and devices may be used to diagnose and/or treat discogenic lower back pain, by selectively stimulating or evaluating the function of nerves that innervate a posterior longitudinal ligament and/or the adjacent outer posterior annulus fibrosus of a lumbar disc. In preferred embodiments of the invention, the delivered energy is in the form of electrical impulses, but the delivery of light, mechanical-vibration and thermal energy is also disclosed, as well as the removal of heat (cooling) from nerve tissue.

More specifically, the present invention is directed to methods and devices for the treatment of chronic lower back pain that may result from a degenerated or injured intervertebral disc, or paraspinal-mediated low back pain. Electrodes placed in an anterior epidural space of the patient, along with a pulse generator that is connected to the electrodes, are used to deliver electrical impulses to nociceptive and/or other nerves located within the posterior longitudinal ligament (PLL) of the lumbar spine and the superficial layer of the dorsal aspect of the annulus fibrosus that lies under the PLL. Alternatively or in addition, devices that generate time-varying light, heat, cold, or mechanical vibration are applied to such nerves, and those devices are supplied with energy by corresponding signal (pulse) generators. According to the invention, these modalities of stimulation in the lumbar region may reduce back pain in a patient reversibly, adjustably, and with almost complete coverage of the pain-generating region, for example, by interfering with or modulating afferent pain signals to the brain that originate in those nerves. Alternatively, if the reversible stimulation is unsuccessful in alleviating the back pain, stimulation parameters may be selected so as to irreversibly damage the ability of the nerves to send pain signals to the brain. Methods are also described for diagnosing the pathophysiological origin of the back pain, and those diagnostic methods may be used to select the stimulation parameters for the disclosed therapeutic methods and devices, thereby individualizing treatment of the patient.

The disclosed methods involve the implantation of stimulation devices, such as electrodes, within the anterior epidural space, adjacent to the posterior longitudinal ligament (PLL) of the lumbar spine. Such implantation is disclosed in detail below, but for purposes of providing background information, the relevant anatomy of the spine and vertebrae will first be summarized and illustrated in FIGS. 1 to 4.

Proceeding from the neck to the tailbone, there are 7 cervical (neck) vertebrae (C1-C7), 12 thoracic vertebrae (T1-T12), and 5 lumbar vertebrae (L1-L5). This is followed by the 5 sacral and coccyx (tailbone) vertebrae, which are inserted like a wedge between the two hip bones. The present invention is concerned primarily with the lumbar vertebrae L3 to L5, although it is understood that the invention may be adapted for use in other vertebrae as well, for example, the lumbar vertebrae L1 to L3, or the sacral vertebrae.

The vertebral column comprises bony vertebral bodies that are separated by cartilaginous intervertebral discs. A primary function of the vertebral column is to provide mechanical support for the body. The intervertebral discs provide a cushion between the vertebral bodies, absorbing some of the axial load and also facilitating motion within the vertebral column. Each disc contains a soft gel-like center (the nucleus pulposus), which is constrained radially by an elastic outer band, the annulus fibrosus. Each vertebral body articulates with its neighboring vertebral body above and below, which allows for some degree of flexion, extension, and rotation [HUMZAH M D, Soames R W. Human intervertebral disc: structure and function. Anat Rec 220 (4, 1988):337-356].

Ligaments connect two or more bones and help stabilize joints. The present invention is concerned particularly with the posterior longitudinal ligament (PLL), which runs axially along the interior portion of the vertebral bodies and of the annulus fibrosus of the discs that lie between the vertebral bodies. The PLL protects the discs and imparts stability during flexion of the body [David W. L Hukins and Judith R. Meakin. Relationship between structure and mechanical function of the tissues of the intervertebral joint. Amer. Zool. 40 (2000):42-52]. Furthermore, nerves that innervate the PLL may participate in reflex loops that cause back muscles to stabilize the spine. Thus, neural receptors in the posterior longitudinal ligament, simultaneously with the output of the receptors from other ligaments such as the supraspinal ligament, as well as receptors in the discs, are thought to add their neural outputs to spinal interneurons, so as to reflexively activate the multifidus and longissimus muscles of the back in order to stabilize the spine in response to loads and movements [PANJABI M M. Clinical spinal instability and low back pain. J Electromyogr Kinesiol 13 (4, 2003):371-379].

The posterior longitudinal ligament may be injured (sprained, as a stretch and/or tear) as the result of sudden violent contraction, sudden torsion, lifting a heavy object, or other acute mechanical events. Because the PLL lies adjacent to the posterior annulus fibrosus of the intervertebral disc, inflammation of the disc that results from degeneration or herniation of the disc may secondarily contribute to dysfunction of the PLL, e.g., via inflammatory mediators. The most thoroughly investigated disease of the PLL itself is its ossification, which is more common in the cervical (70%), as compared to either thoracic (15%) or lumbar (15%) regions [Joji INAMASU, Bernard H. Guiot and Donald C. Sachs. Ossification of the Posterior Longitudinal Ligament: An Update on Its Biology, Epidemiology, and Natural History. Neurosurgery 58 (6, 2006): 1027-1039]. The PLL may also fold and compress a nerve root [BEATTY R A, Sugar O, Fox T A. Protrusion of the posterior longitudinal ligament simulating herniated lumbar intervertebral disc. J Neurol Neurosurg Psychiatry 31 (1, 1968):61-66].

Each vertebra is composed of the above-mentioned vertebral body (anteriorly) and an arch (posteriorly). Processes protrude from each arch and serve as points of attachment for muscles of the back. A spinous process protrudes backwards on each arch, and transverse processes extend from the lateral edges of each arch. The parts of the arch between the spinous and transverse processes are known as laminae, and the parts of the arch between the transverse processes and the body are known as pedicles. At the point where the laminae and pedicles meet, each vertebra contains two superior articular facets and two inferior articular facets. The pedicle of each vertebra is notched at its superior and inferior edges. Together the notches from two contiguous vertebrae form an opening, the intervertebral neural foramen, through which spinal nerves pass.

A vertebral arch also contains an opening (the vertebral foramen) which forms a canal through which the spinal cord passes, protecting the spinal cord and nerve roots that exit from it. Because the spinal cord stops growing in infancy while the bones of the spine continue to grow, the spinal cord in adults ends at about the level of the vertebra L1/L2. Below that vertebral level, a bundle-like structure of nerve fibers, known as the cauda equina, occupy the vertebral foramen, which emanates from the terminus of the spinal cord (the conus medullaris). Thus, the lumbar vertebral foramen surrounds the spinal cord/conus medullaris above vertebrae L1/L2 and the cauda equina nerve roots below vertebrae L1/L2. [J. D. STEWART Cauda equina disorders. Chapter 6, pp 63-74. In: Neurologic Bladder, Bowel and Sexual Dysfunction (Clare J Fowler et al, eds) Amsterdam: Elsevier Science, 2001].

The above-mentioned structures are illustrated in FIGS. 1 to 4. Features shown in those figures that are particularly relevant to the present invention include the location of the posterior longitudinal ligament (PLL) and the annulus fibrosus of the intervertebral disc(s) that lies adjacent to the PLL. For future reference, the location of stimulation devices of the present invention, which are implanted adjacent to the PLL, is also shown in FIGS. 1-4 (item 6 in FIG. 1, item 6 in FIG. 2, item 6 in FIG. 3, and within regions 50 and/or 51 in FIG. 4).

FIG. 1 shows the spine in a cross section perpendicular to its long axis, cut through one of the lumbar discs. The interconnections between the nerves that are shown in FIG. 1 are relevant to the mechanism by which the disclosed stimulation of nerves innervating the PLL and annulus fibrosus may reduce back pain [EDGAR M A. The nerve supply of the lumbar intervertebral disc. J Bone Joint Surg Br 89 (9, 2007):1135-1139]. Structures labeled in FIG. 1 are as follows: nucleus pulposus 1; annulus fibrosus 2; anterior longitudinal ligament 3; posterior longitudinal ligament 4; thecal sac 5; devices (e.g., electrodes) of the present invention situated in the anterior epidural space 6; filum terminale 7; intrathecal nerve root of the cauda equina 8; ventral nerve root 9; dorsal nerve root 10; dorsal root ganglion 11; dorsal ramus of the spinal nerve 12; medial branch of the dorsal ramus 13; sinuvertebral nerve (meningeal branch of the spinal nerve) 14; connecting sympathetic branch from gray ramus to sinuvertebral nerve 15; neural radicals from sinuvertebral nerve to disc 16; white ramus communicans 17; gray ramus communicans 18; sympathetic neural radicals to disc surface 19; paraspinal sympathetic ganglion 20; paraspinal sympathetic chain 21; anterior branch from sympathetic ganglion to disc surface 22; branches from sympathetic ganglion to disc surface 23; and posterior epidural space 24. FIG. 1 is adapted from: J. Randy JINKINS. The anatomic and physiologic basis of local, referred, and radiating lumbosacral pain syndromes related to disease of the spine. J Neuroradiol 31 (2004): 163-180.

FIG. 2 shows a section of the spine viewed from the side (left-to-right). The section is angled slightly away from the midline of the back, so as to demonstrate many of the ligaments of the spine. Vertebral bodies are labeled T12 through S1 as shown. Structures otherwise labeled in FIG. 2 are as follows: anterior longitudinal ligament 3; posterior longitudinal ligament 4; spinal cord 26; cauda equina 27; membrane of dura mater that surrounds the spinal cord and the cauda equina (thecal sac, dural tube) containing cerebral spinal fluid 5; devices (e.g., electrodes) of the present invention situated in the anterior epidural space 6; posterior epidural space 24; anterior epidural space 25; intervertebral disc 29; ligamentum flavum 30; interspinous ligament 31; supraspinous ligament 32; sacrococcygeal ligament 33; and sacral hiatus 34.

FIG. 3 shows a posterior-to-anterior view of the lumbar spine, viewed obliquely on the left side of the patient. Vertebral bodies are labeled L3 through L5 as shown. The structures that are otherwise labeled in FIG. 3 are as follows: posterior longitudinal ligament 4; devices (e.g., electrodes) of the present invention situated in anterior epidural space 6; membrane of dura mater that surrounds the cauda equina (thecal sac, dural tube), containing cerebral spinal fluid 5; cauda equina nerve roots 27; intervertrbal disc 29; ligamentum flavum 30; L3 nerve root 35; L4 nerve root 36; L5 nerve root 37; pedicle (cut) 40; lamina (cut) 41; spinous process 42; transverse process 43; superior articular process 44; and facet joint 45.

The present invention stimulates nerves in the PLL, in the connective tissue between the PLL and annulus fibrosus and/or periosteum, and in the superficial layer of the dorsal aspect of the annulus fibrosus that lies under the PLL [BOGDUK N, Tynan W, Wilson A S. The nerve supply to the human lumbar intervertebral discs. J Anat 132 (1, 1981): 39-56; EDGAR M A. The nerve supply of the lumbar intervertebral disc. J Bone Joint Surg Br 89 (9, 2007):1135-1139; KOJIMA Y, Maeda T, Arai R, Shichikawa K. Nerve supply to the posterior longitudinal ligament and the intervertebral disc of the rat vertebral column as studied by acetylcholinesterase histochemistry. I. Distribution in the lumbar region. J Anat 169 (1990):237-246; J. H. MULLIGAN. The innervation of the ligaments attached to the bodies of the vertebrae. J Anat 91 (4, 1957): 455-465]. FIG. 4 shows a posterior-to-anterior view of the innervation of the posterior longitudinal ligament (PLL) and of the annulus fibrosus of the intervertebral disc that lies adjacent to the PLL. In this view, many of the structures shown in FIG. 3 are removed. Structures labeled in FIG. 4 are as follows: posterior longitudinal ligament 4; intervertebral fibers of the PLL 48; vertebral (longitudinal) fibers of the PLL 49; sinuvertebral nerve 14; nerve root 38; pedicle (cut) 40; horizontal region that may be stimulated by the disclosed devices 50; and vertical (longitudinal) region that may be stimulated by the disclosed devices 51.

Low back pain is extremely prevalent and is the second most common reason for patients to seek medical attention. Pain may be elicited during times of overexertion that results in sprain, strain, or spasm in one or more of the muscles or ligaments in the back. If the spine becomes overly strained or compressed, a disc may rupture or bulge outward. Prolonged stresses or degenerative changes facilitated by genetic predisposition, aging, obesity, smoking, arthritis, poor posture, or unhealthy activity-related habits may result in injury to the intervertebral disc, resulting in chronic discogenic-mediated low back pain [Devon I RUBIN. Epidemiology and risk factors for spine pain. Neurol Clin 25 (2007): 353-371; MANCHIKANTI L, Singh V, Datta S, Cohen S P, Hirsch J A; American Society of Interventional Pain Physicians. Comprehensive review of epidemiology, scope, and impact of spinal pain. Pain Physician 12 (4, 2009):E35-E70].

Acute back pain tends to come on suddenly, but also tends to improve in a short period of time with short-term conservative treatment, such as medication, exercise, physical therapy or rest [ATLAS S J, Deyo R A. Evaluating and managing acute low back pain in the primary care setting. J Gen Intern Med 16 (2, 2001):120-131]. Chronic back pain is commonly described as deep, aching, dull or burning pain in one area of the back, which may also travel down the leg(s). It tends to last a month or more or may be a persistent unrelenting problem. Sciatica is pain that begins in the hip and/or buttocks and travels down the back of the leg. There are many causes of chronic back pain, including some that are from intra-abdominal disorders that can cause pain to be referred to the back. Other examples of causes of back pain are as follows: A radiculopathy can be due to a pinched nerve resulting from a herniated disc; sciatica can be due to pinched nerves in vertebrae L4-S3; central spinal stenosis is due to narrowing of the spinal canal; foraminal stenosis is due to bone spurs that protrude into the neural foramen and put pressure on a nerve root; and low back pain can also be due to gradual loss of normal spinal structure associated with spondylosis, spinal osteoarthritis, and/or degenerative disc disease [Michael DEVEREAUX. Low back pain. Med Clin N America 93 (2009):477-501; Michelle L I N. Musculoskeletal Back Pain. Chapter 51, pp 591-603. In: Rosen's Emergency Medicine: Concepts and Clinical Practice, 7th edition (Marx J A, Hockberger R S, Walls R M, et al, eds). Philadelphia: Mosby Elsevier, 2009; LAST A R, Hulbert K. Chronic low back pain: evaluation and management. Am Fam Physician 79 (12, 2009):1067-1074; McCAMEY K, Evans P. Low back pain. Prim Care 34 (1, 2007):71-82]. CHOU et al provide a flowchart to assist in the diagnosis and subsequent treatment of low back pain [CHOU R, Qaseem A, Snow V, Casey D, Cross J T Jr, Shekelle P, Owens D K; Clinical Efficacy Assessment Subcommittee of the American College of Physicians; American College of Physicians; American Pain Society Low Back Pain Guidelines Panel. Diagnosis and treatment of low back pain: a joint clinical practice guideline from the American College of Physicians and the American Pain Society. Ann Intern Med 147 (7, 2007): 478-491].

The present invention is concerned primarily with back pain that is due to degenerative disc disease, wherein degenerative changes following loss of hydration of the nucleus pulposus lead to circumferential or radial tears within the annulus fibrosus. Annular tears within the outer annulus stimulate the ingrowth of blood vessels and accompanying nociceptors into the outer annulus, for example, from the overlying posterior longitudinal ligament. Nerve endings are recruited to the area of injury and sensitized by inflammatory cytokines and other chemofactors. Pain transmission is then sustained by chronic inflammation and exacerbated by constant axial loading [KALLEWAARD J W, Terheggen M A, Groen GJ, Sluijter M E, Derby R, Kapural L, Mekhail N, van Kleef M. (15.) Discogenic low back pain. Pain Practice 10 (6, 2010):560-579; Keith D. WILLIAMS and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007; AUDETTE J F, Emenike E, Meleger A L. Neuropathic low back pain. Curr Pain Headache Rep 9 (3, 2005):168-177; HURRI H, Karppinen J. Discogenic pain. Pain 112 (3, 2004):225-228; FREEMONT A J, Peacock T E, Goupille P, Hoyland J A, O'Brien J, Jayson M I. Nerve ingrowth into diseased intervertebral disc in chronic back pain. Lancet 350 (9072, 1997):178-181].

Although the pathophysiology of degenerative disc disease is incompletely understood, it is thought that sensitization of these nociceptors by various inflammatory repair mechanisms may lead to chronic discogenic pain [MARTIN M D, Boxell C M, Malone D G. Pathophysiology of lumbar disc degeneration: a review of the literature. Neurosurg Focus 13 (2, 2002):Article 1, pp. 1-6; PENG B, Wu W, Hou S, Li P, Zhang C, Yang Y. The pathogenesis of discogenic low back pain. J Bone Joint Surg Br 87 (1, 2005): 62-67; Y. AOKI, K. Takahashi, S. Ohtori & H. Moriya: Neuropathology Of Discogenic Low Back Pain: A Review. The Internet Journal of Spine Surgery 2 (1, 2005): 1-9; WALKER M H, Anderson D G. Molecular basis of intervertebral disc degeneration. Spine J 4 (6 Suppl, 2004):158S-166S; BOSWELL M V, et al. Interventional techniques: evidence-based practice guidelines in the management of chronic spinal pain. Pain Physician 10 (1, 2007):7-111; J. Randy JINKINS. The anatomic and physiologic basis of local, referred, and radiating lumbosacral pain syndromes related to disease of the spine. J Neuroradiol 31 (2004): 163-180; SEAMAN D R, Cleveland C 3rd. Spinal pain syndromes: nociceptive, neuropathic, and psychologic mechanisms. J Manipulative Physiol Ther 22 (7, 1999):458-472; NAKAMURA SI, Takahashi K, Takahashi Y, Yamagata M, Moriya H. The afferent pathways of discogenic low-back pain. Evaluation of L2 spinal nerve infiltration. J Bone Joint Surg Br 78 (4, 1996): 606-612; TAKEBAYASHI T, Cavanaugh J M, Kallakuri S, Chen C, Yamashita T. Sympathetic afferent units from lumbar intervertebral discs. J Bone Joint Surg Br 88 (4, 2006):554-557].

The current standard for diagnosing discogenic pain is pressure-controlled provocative discography [TOMECEK FJ, Anthony C S, Boxell C, Warren J. Discography interpretation and techniques in the lumbar spine. Neurosurg Focus 13 (2, 2002):Article 13, pp 1-8; ZHANG Y G, Guo T M, Guo X, Wu S X. Clinical diagnosis for discogenic low back pain. Int J Biol Sci 5 (7, 2009):647-658]. With this procedure, needles are inserted through the back into the disc near the suspect area, guided by fluoroscopic imaging. Fluid is then injected to pressurize the disc, and any pain responses are recorded. The fluid may comprise a radiographic contrast agent, thereby allowing disc morphology to be imaged, so that the procedure provides both anatomical and functional information about a diseased disc. Diagnostic nerve blockade may also be used to characterize the nerve source of the low back pain [MANCHIKANTI L, Singh V, Pampati V, Damron K S, Barnhill R C, Beyer C, Cash K A. Evaluation of the relative contributions of various structures in chronic low back pain. Pain Physician 4 (4, 2001):308-316]. However, interpretation of results given by provocative discography and nerve blockade can be equivocal or controversial, and those methods do not necessarily predict the success of potential disc therapies. Accordingly, it is an objective of the present invention to provide improved diagnostic procedures that may complement results provided by discography and nerve blockade, and that are also particularly well-suited for use in selecting parameters of the therapeutic nerve-stimulation procedures that are disclosed here. Thus, if a patient is a candidate for provocative discography or nerve blockade, the presently disclosed diagnostic methods may be performed in conjunction with those invasive procedures, or the disclosed methods may be performed by themselves.

Several therapies have been used to target the nociceptive nerve fibers within the affected discs in patients with discogenic back pain. Non-surgical techniques involve pain medication and physical therapy with behavioral modification [KINKADE S. Evaluation and treatment of acute low back pain. Am Fam Physician 75 (8, 2007):1181-1188; Brian S WILLIAMS and Paul J Christo. Pharmacological and interventional treatments for neuropathic pain. Chapter 12, pp 295-375. In: Mechanisms of Pain in Peripheral Neuropathy (M Dobretsov and J-M Zhang, eds). Trivandrum, India: Research Signpost, 2009; CHOU R, Huffman L H; American Pain Society; American College of Physicians. Nonpharmacologic therapies for acute and chronic low back pain: a review of the evidence for an American Pain Society/American College of Physicians clinical practice guideline. Ann Intern Med 147 (7, 2007): 492-504].

Other destructive minimally invasive and surgical techniques have been used when conservative measures fail [BOSWELL M V, et al. Interventional techniques: evidence-based practice guidelines in the management of chronic spinal pain. Pain Physician 10 (1, 2007):7-111; LAVELLE W F, Lavelle E D, Smith H S. Interventional techniques for back pain. Clin Geriatr Med 24 (2, 2008):345-68]. Minimally invasive techniques include Intradiscal electrothermal therapy (IDET), which involves the application of heat via a needle that is inserted transcutaneously into the disc [DERBY R, Eek B, Chen Y, O'neill C, Ryan D. Intradiscal Electrothermal Annuloplasty (IDET): A Novel Approach for Treating Chronic Discogenic Back Pain. Neuromodulation 3 (2, 2000):82-88]. Alternatively, radiofrequency annuloplasty is a technique used to target the affected area using a needle to deliver radiofrequency energy for destructive purposes [HELM S, Hayek S M, Benyamin R M, Manchikanti L. Systematic review of the effectiveness of thermal annular procedures in treating discogenic low back pain. Pain Physician 12 (1, 2009):207-232]. Rather than using heat to destroy nerves in the affected area, it has been proposed that they may be destroyed using ionizing radiation [U.S. Pat. No. 7,634,307, entitled Method and apparatus for treatment of discogenic pain, to SWEENEY].

Surgical techniques are also used to remove a large portion of the disc followed by a fusion procedure between the two adjoining vertebral bodies [CHOU R, Baisden J, Carragee E J, Resnick D K, Shaffer W O, Loeser J D. Surgery for low back pain: a review of the evidence for an American Pain Society Clinical Practice Guideline. Spine 34 (10, 2009):1094-1109; LAVELLE W, Carl A, Lavelle E D. Invasive and minimally invasive surgical techniques for back pain conditions. Med Clin North Am 91 (2, 2007):287-298; SCHWENDER J D, Foley K T, Holly L T, Transfeldt, E. Minimally Invasive Posterior Surgical Approaches to the Lumbar Spine. Chapter 21, pp. 333-341 In: The Spine, Fifth Edition (Harry N. Herkowitz, Richard A. Balderston, Steven R. Garfin, Frank J. Eismont, eds). Philadelphia: Saunders/Elsevier, 2006; GRIFFITH SL, Davis R J, Hutton WC. Repair of the Anulus Fibrosus of the Lumbar Disc. Chapter 12 (pp 41-48), In: Nucleus Arthroplasty Technology in Spinal Care: Volume II—Biomechanics & Development. Davis R, Cammisa F P, Girardi F P, Hutton W C, Editors. Bloomington, Minn.: Raymedica Co, 2007].

As described in the above-cited publications, all of these techniques have varying degrees of success, and pain relief is generally temporary. A problem with IDET and similar minimally invasive techniques is that destruction of nociceptors within the posterior annulus is variable and incomplete. In addition, the offending region involving the PLL is not addressed.

Several patents or patent applications disclose methods similar to radiofrequency annuloplasty, wherein an array of electrodes (a lead) is introduced into the disc (but not into the epidural space adjacent to the disc) to thermally ablate disc tissue. In U.S. Pat. No. 8,066,702, entitled Combination electrical stimulating and infusion medical device and method, to RITTMAN, III, et al., radiofrequency energy is transmitted to tissue surrounding the lead, thereby ablating the tissue. U.S. Pat. Nos. 6,772,012 and 7,270,659, entitled Methods for electrosurgical treatment of spinal tissue, to RICART et al., also describe controlled heating to ablate various tissues in or around the vertebral column using a radiofrequency voltage, including possibly a posterior longitudinal ligament. A thermal ablation method that may also be directed to the posterior longitudinal ligament, involving electrosurgically coagulating nerve tissue within the posterior of the annulus fibrosus by applying heat, is disclosed in U.S. Pat. No. 7,331,956, entitled Methods and apparatus for treating back pain, to HOVDA et al. Similarly, abandoned application U.S. Ser. No. 11/105,274, corresponding to publication No. US20050261754, entitled Methods and apparatus for treating back pain, to WOLOSZKO et al., describes denervation of an intervertebral disc or a region of the posterior longitudinal ligament by the controlled application of heat to a target tissue. All of the methods disclosed in those patents affect the offending region irreversibly, through the application of joule heating. In contrast, in the preferred embodiments of the present invention, stimulation devices, such as electrodes, are introduced to affect the offending region reversibly, not irreversibly. Alternatively, in other embodiments of the present invention, the offending region may be affected irreversibly when the reversible methods fail to reduce the patient's pain.

Lower back pain has been treated reversibly by stimulation of the spinal cord, using electrical stimulation devices that are used generically to modulate neuronal function [ten VAARWERK I A, Staal Mi. Spinal cord stimulation in chronic pain syndromes. Spinal Cord 36 (10, 1998):671-682; NORTH RB, Wetzel F T. Spinal cord stimulation for chronic pain of spinal origin: a valuable long-term solution. Spine 27 (2, 2002):2584-2591; STOJANOVIC M P, Abdi S. Spinal cord stimulation. Pain Physician 5 (2, 2002):156-166; BAROLAT G, Sharan A. Spinal Cord Stimulation for Chronic Pain Management. In Pain Management for the Neurosurgeon: Part 2, Seminars in Neurosurgery 15 (2, 2004):151-175; R. B. NORTH. Neural interface devices: spinal cord stimulation technology. Proceedings of the IEEE 96 (7, 2008): 1108-1119; Allen W. BURTON, Phillip C. Phan. Spinal Cord Stimulation for Pain Management. Chapter 7, pp. 7-1 to 7-16, In: Neuroengineering (Daniel J. DiLorenzo and Joseph D. Bronzino, eds). Boca Raton: CRC Press, 2008; Steven FALOWSKI, Amanda Celii, and Ashwini Sharan. Spinal cord stimulation: an update. Neurotherapeutics 5 (1, 2008):86-99; KUNNUMPURATH S, Srinivasagopalan R, Vadivelu N. Spinal cord stimulation: principles of past, present and future practice: a review. J Clin Monit Comput 23 (5, 2009):333-339]. Other examples of electrical stimulation are deep brain stimulation for treatment of Parkinson's disease or other movement disorders, complex regional pain syndrome (previously referred to as reflex sympathetic dystrophy), post herpetic neuralgia and others. In addition to centrally mediated nerve stimulation, peripheral nerve stimulation has also been used to successfully treat neuropathic pain syndromes such as occipital, trigeminal, and post herpetic neuralgias [WHITE P F, Li S, Chiu J W. Electroanalgesia: its role in acute and chronic pain management. Anesth Analg 92 (2, 2001):505-513; STANTON-HICKS M, Salamon J. Stimulation of the central and peripheral nervous system for the control of pain. J Clin Neurophysiol 14 (1, 1997):46-62].

Although spinal cord electrical stimulation is an established method for treating axial lower back pain, it produces improvement in back pain in only approximately 50% of patients [John C. OAKLEY. Spinal Cord Stimulation in Axial Low Back Pain: Solving the Dilemma. Pain Medicine 7 (Supplement s1, 2006):558-563]. The devices used for spinal cord stimulation comprise: (1) electrodes that are implanted in the spine, and (2) a power source that delivers electrical pulses to the electrodes. The present invention also discloses electrodes that are implanted in the spine and a power source that powers the electrical pulses that are delivered to the electrodes, but which are not a spinal cord stimulator for reasons described below.

Commercially available general-purpose electrodes and pulse generators that are used for spinal cord stimulation and peripheral nerve stimulation could in principle also be used to electrically stimulate the lumbar posterior longitudinal ligament and adjoining outer posterior annulus fibrosus of the intervertebral discs. However, as disclosed below, such general-purpose stimulators are not well-suited for the objectives of the present invention. Furthermore, devices according to the present invention are not spinal cord stimulators for treating back pain. In fact, electrodes in the present invention are placed in the canal defined by the vertebral foramen in the lumbar region and in most cases, below the spinal cord, where the cauda equina rather than the spinal cord occupies that opening. Heretofore, when the lumbar columns have been stimulated with spinal cord stimulator devices, it has been for purposes of spasticity control or the generation of muscle activity in spinal cord injury patients, not for purposes of treating back pain [DANNER S M, Hofstoetter U S, Ladenbauer J, Rattay F, Minassian K. Can the human lumbar posterior columns be stimulated by transcutaneous spinal cord stimulation? A modeling study. Artif Organs 35 (3, 2011):257-262]. In order to explain differences between the present invention and spinal cord stimulators, the development and use of spinal cord stimulators will first be summarized.

Spinal cord electrical stimulation for the treatment of pain was first performed in 1967 by SHEALY and colleagues [SHEALY C N, Mortimer J T, Reswick J B. Electrical inhibition of pain by stimulation of the dorsal columns: preliminary clinical report. Anesth Analg 46 (4, 1967):489-491]. In the decade that followed, many variations in technique were tried. Electrodes were implanted at different locations relative to the spinal cord: in endodural, subdural, subarachnoid, and epidural positions. To do so, a significant amount of spinal bone was often removed, in order to allow placement of the electrodes (a surgical laminectomy, or complete removal of vertebral lamina). In other cases, a small window of bone was drilled over the area, using less invasive techniques (laminotomy, or partial removal of vertebral lamina). Finally, minimally invasive techniques were developed to implant a catheter-like electrode lead percutaneously.

Rather than implanting the electrodes one-by-one, leads (also known as electrode arrays) were developed wherein multiple electrodes were mounted on, in, or about an insulating substrate, and the lead was then implanted. Such leads may have the shape of a plate and are said to contain paddle electrodes, plate electrodes, ribbon electrodes, surgical electrodes or laminotomy electrodes. For percutaneous implantation, the leads may also have the shape of a wire or catheter, which are said to contain percutaneous or wire electrodes.

In almost all cases, the electrodes were implanted on the posterior side of the spinal cord, i.e., the side most accessible from the back. However, in 1975 LARSON et al. and HOPPERSTEIN implanted electrodes on the anterior side of the spinal column, in an attempt to improve the low success rate of spinal cord stimulation in reducing pain [Sanford J. LARSON, Anthony Sances, Joseph F. Cusick, Glenn A. Meyer, Thomas Swiontek. A comparison between anterior and posterior spinal implant systems. Surg. Neurol. 4 (1975):180-186; Reuben HOPPENSTEIN. Electrical stimulation of the ventral and dorsal columns of the spinal cord for relief of chronic intractable pain: preliminary report. Surg. Neurol. 4 (1975):187-194]. In contrast to the present invention, though, they did not implant the anterior electrodes within the anterior epidural space, they did not attempt to implant electrodes in the lumbar spine, and they were not concerned with the treatment of back pain. Furthermore, the anteriorly-placed electrodes were configured to stimulate the spinal cord, which is different than the configuration that would stimulate only nerves in the posterior longitudinal ligament and the underlying annulus fibrosus as in the present invention.

The anterior location of the electrode in the epidural space is particularly relevant to the present invention. The epidural space is the space within the spinal canal lying outside the dura mater (dural or thecal sac), which contains lymphatics, spinal nerve roots, loose fatty tissue, small arteries, and blood vessels. The epidural space surrounds the dural sac and is bounded by the posterior longitudinal ligament anteriorly, the ligamenta flava and the periosteum of the laminae posteriorly, and the pedicles of the spinal column and the intervertebral neural foramina containing their neural elements laterally. The space communicates freely with the paravertebral space through the intervertebral neural foramina. For spinal cord stimulation, the electrodes are now invariably implanted in the posterior epidural space.

However, a percutaneous lead may be accidentally introduced into the anterior epidural space, which is considered to be an error, and the lead is withdrawn. Thus, FALOWSKI et al. write that "Frequently, the electrode curves around the dural sac and ends in the ventral epidural space. A gentle lateral curve of the electrode shortly after its entry into the epidural space should arouse the suspicion that it is directing ventrally around the dural sac. Absolute confirmation of the ventral location arises from the stimulation generating violent motor contractions or observation [by fluoroscopy] in the lateral plane which would readily disclose the anterior position of the electrode tip." [Steven FALOWSKI, Amanda Celii, and Ashwini Sharan. Spinal cord stimulation: an update. Neurotherapeutics 5 (1, 2008):86-99]. Thus, in contrast to the present invention, implantation of a spinal cord electrode in the anterior epidural space is considered to be an error, and in any event, the implantation of spinal cord stimulator electrodes is not performed in the lumbar spine (e.g., L3-L5). Furthermore, in the present invention, the electrical stimulus is directed towards the posterior longitudinal ligament in such a way that motor contractions are not induced by the stimulation. Applicant is unaware of the deliberate percutaneous implantation of a spinal cord stimulator in the anterior epidural space. As disclosed herein, such deliberate implantation in the anterior epidural space would likely involve a different anatomical route than the interlaminal approach that is taken for access to the posterior epidural space. Thus, as is known from the methods for performing epidural injections, to reach the anterior epidural space, a transforaminal anatomical approach may be taken, and for lumbar vertebrae, a sacral route may be taken as well [Mark A. HARRAST. Epidural steroid injections for lumbar spinal stenosis. Curr Rev Musculoskelet Med 1:(2008):32-38].

Spinal cord stimulation is performed for the treatment of back pain, but it involves stimulation in vertebrae other than the lumbar spine L3-L5. The vertebral location of the stimulator electrodes is selected on the basis of the location of the patient's pain. BAROLAT et al. mapped the body areas that may be targeted by stimulation of the spinal cord in different vertebrae and made the following observations concerning how best to stimulate to treat lower back pain. "It is very difficult to stimulate the low back only, without intervening chest/abdominal wall stimulation . . . (1) the peak curve for low-back stimulation coincides with the peak curve for the chest/abdominal wall . . . (2) the chest/abdominal wall region has a higher percentage of stimulation than the low back; and (3) the chest/abdominal wall area has a lower stimulation threshold than the low back. All of these factors contribute to the challenge of being able to direct stimulation selectively to the low back without interference from the body walls. In our experience, the best location was about T9-10, with the electrode placed strictly at the midline." [BAROLAT G, Massaro F, He J, Zeme S, Ketcik B. Mapping of sensory responses to epidural stimulation of the intraspinal neural structures in man. J Neurosurg 78 (2, 1993):233-239].

It is therefore not surprising that the effectiveness of spinal cord stimulation for lower back pain is equivocal. Most reviews of its effectiveness have been made in connection with the treatment of Failed Back Surgery Syndrome (FBSS), which may involve pain in locations in addition to the back (e.g., the leg). A Cochrane review of random clinical trials for the treatment of FBSS by spinal cord stimulation concluded that although one clinical trial does provide some limited evidence in favor of spinal cord stimulation, the numbers are small and as a result the study fails to achieve statistical significance [MAILIS_GAGNON A, Furlan A D, Sandoval J A, Taylor R. Spinal cord stimulation for chronic pain. Cochrane Database Syst Rev. 2004;(3):CD003783, pp. 1-16, updated 2009]. Other reviews indicate that up to 40 percent of such FBSS patients do not benefit substantially from spinal cord stimulation [ELDABE S, Kumar K, Buchser E, Taylor R S. An analysis of the components of pain, function, and health-related quality of life in patients with failed back surgery syndrome treated with spinal cord stimulation or conventional medical management. Neuromodulation 13 (3, 2010):201-209; FREY ME, Manchikanti L, Benyamin R M, Schultz D M, Smith H S, Cohen S P. Spinal cord stimulation for patients with failed back surgery syndrome: a systematic review. Pain Physician 12 (2, 2009):379-397].

Similarly, a review found that spinal cord stimulation for treatment specifically of discogenic pain might be useful, as evidenced by a reduction in opioid usage by such patients, but the review involved only a small number of patients [VALLEJO R, Manuel Zevallos L, Lowe J, Benyamin R. Is Spinal Cord Stimulation an Effective Treatment Option for Discogenic Pain? Pain Pract 12 (3, 2012):194-201]. OAKLEY reviews the problem of why approximately 50% of patients with lower back pain are not helped by spinal cord stimulation. He suggests that advances in stimulator technology may help, such as properly selecting the number and location of stimulator electrodes, using pulse generators with independent current control over each lead contact electrode, and optimizing the stimulation waveform (e.g., pulse width) [John C. OAKLEY. Spinal Cord Stimulation in Axial Low Back Pain: Solving the Dilemma. Pain Medicine 7 (Supplement s1, 2006):558-563]. In regards to stimulus waveform optimization, AL-KAISY et al. suggest that the use of high frequency pulses may help [Adnan AL-KAISY, Iris Smet, and Jean-Pierre Van Buyten. Analgesia of axial low back pain with novel spinal neuromodulation. Poster presentation #202 at the 2011 meeting of The American Academy of Pain Medicine, held in National Harbor, Md., Mar. 24-27, 2011].

The above-cited literature demonstrates that the treatment of lower back pain by invasive electrical stimulation is in need of improvement. To that end, the present invention is motivated by the fact that the innervation of the posterior longitudinal ligament and the underlying annulus fibrosus may be the predominant origin of the lower back pain. Thus, KUSLICH et al. write that " . . . we had the opportunity to perform more than 700 operations on the lumbar spine while using local anesthesia . . . . Back pain could be produced by stimulation of several lumbar tissues, but by far, the most common tissue of origin [of back pain] was the outer layer of the annulus fibrosus and posterior longitudinal ligament." [KUSLICH SD, Ulstrom C L, Michael C J. The tissue origin of low back pain and sciatica: a report of pain response to tissue stimulation during operations on the lumbar spine using local anesthesia. Orthop Clin North Am 22 (2, 1991): 181-187].

To affect the innervation of the lumbar posterior longitudinal ligament, the electrodes that stimulate them need to be placed in the lumbar spine, which is not done in spinal cord stimulation for back pain. At that lumbar location, the cauda equina is situated posterior to the posterior longitudinal ligament. Placement of an electrode between the posterior longitudinal ligament and the cauda equina would cause the cauda equina to be stimulated, if the electrode were to stimulate in all directions. Such stimulation of the cauda equina would be very undesirable because it would cause leg movements resulting from stimulation of nerve roots within the cauda equina.

In fact, there are only a few reasons for electrically stimulating the cauda equina, and they are not relevant to the treatment of discogenic back pain. Electrical stimulation of the cauda equina, through high voltage percutaneous or transcutaneous stimulation above the lumbar vertebrae, is sometimes done in order to assess conduction in the cauda equina, which is accompanied by electromyographic activity in muscles of a lower limb. However, this does not involve placement of an electrode in the epidural space [Maertens de NOORDHOUT A, Rothwell J C, Thompson P D, Day B L, Marsden C D. Percutaneous electrical stimulation of lumbosacral roots in man. J Neurol Neurosurg Psychiatry 51 (2, 1988):174-81]. Electrodes have been placed in the posterior epidural space in the vicinity of the conus medullaris and cauda equina, but this is done only for purposes of mapping or monitoring, not for the treatment of lower back pain, and not for purposes of stimulating the posterior longitudinal ligament or posterior annulus fibrosus [KOTHBAUER K F, Deletis V. Intraoperative neurophysiology of the conus medullaris and cauda equina. Childs Nerv Syst 26 (2, 2010): 247-253]. In another situation, a special electrode is used to enable restoration of at least partial control over lower-body functions that are directed by nerves emerging from the end of the spinal cord. The electrode is designed for introduction into the lower end of the dura beneath the conus of the spinal cord, to float in the intrathecal space that is loosely occupied by the sacral roots and other nerves of the cauda equina. Thus, that electrode is not implanted in the epidural space, and it is not intended to treat lower back pain or stimulate the posterior longitudinal ligament or posterior annulus fibrosus [U.S. Pat. No. 4,633,889, entitled Stimulation of cauda-equina spinal nerves, to TALALLA et al].

Therefore, if one wishes to electrically stimulate the lumbar posterior longitudinal ligament to treat back pain reversibly, but avoid stimulation of other structures adjoining the anterior epidural space, at least two problems must be addressed. One is that the electrical stimulation must be directed specifically to the posterior longitudinal ligament and its underlying structures, and this involves not only designing an asymmetric structure for the lead, but also the design of directionality of its insertion into the patient. A second problem is that electrodes, particularly percutaneous electrodes (wire, or catheter-like electrodes) have a tendency to migrate or rotate, such that even if the electrode were initially directed to stimulate the posterior longitudinal ligament, it may eventually rotate or migrate, thereby accidentally stimulating other tissues. The present invention is designed to address both of these problems. It also addresses the problem of selectively ablating the nerves if the reversible stimulation does not work.

These problems are not addressed in the patents that are related to the present invention. In U.S. Pat. No. 7,069,083, 7,831,306, and 8,086,317, all entitled System and method for electrical stimulation of the intervertebral disc, to FINCH et al., a percutaneous (wire, or catheter) lead is placed in a disc or just outside the outer confines of the disc, circumferentially along the entire perimeter of the annulus of the disc. The lead is not placed in the anterior epidural space, there is no suggestion of stimulating the posterior longitudinal ligament, the electrodes do not stimulate in a particular direction, and there is no suggestion of how rotational migration of its cylindrical lead might be retarded. In U.S. Pat. No. 7,945,331, entitled Combination electrical stimulating and infusion medical device and method, to VILIMS, it is suggested incidentally that his disclosed percutaneous (wire, or catheter) lead "is well suited for treatment of other areas along the spine to include the ventral canal along the posterior longitudinal ligament, ventral dura, and the posterior aspect of the disc." However, there is no suggestion as to how the lead would be inserted or used in those locations. In one embodiment of that invention, "the electrodes are not formed circumferentially around the distal portion, but are formed more linearly along one side of the stimulation lead." However, that patent does not suggest how such an electrode would be inserted to selectively stimulate any particular tissue, and it does not suggest how subsequent rotational migration of its cylindrical lead could be retarded. Furthermore, that patent is concerned with managing sacroiliac joint pain in a sacrum of a patient, not discogenic lumbar pain. None of the above-cited patents disclose devices that would almost completely cover a pain-generating region, such as the entire innervation of an offending lumbar posterior longitudinal ligament and adjacent posterior annulus fibrosus of the intervertebral disc(s).

In view of the foregoing, there is a need for a lumbar vertebral column electrical stimulator lead that is adapted for directional insertion into the anterior epidural space adjacent to the posterior longitudinal ligament; that will provide adjustable and reversible non-destructive modulation of nerves in the posterior longitudinal ligament and underlying annulus fibrosus to effectively reduce back pain, when connected to a pulse generator; that will cover the pain-generating region; that will stimulate only the posterior longitudinal ligament and underlying annulus fibrosus, but not nearby tissue such as the cauda equina or nerve roots; and that is not susceptible to accidental rotation or migration.

For patients in which such reversible electrical stimulation does not reduce the pain significantly, there would also be a need for alternate reversible stimulation modalities and procedures (e.g., nerve cooling) that may succeed in reducing the pain, either alone or in combination with reversible electrical stimulation, such that all such stimulation modalities could be evaluated simultaneously using the same implanted device. Whether reversible electrical stimulation or an alternate reversible stimulation modality is used, diagnostic procedures are needed in order to characterize the pathophysiology of the patient's offending nerves, so as to guide the selection of parameters that are used to perform the stimulation (waveform type, stimulation amplitude, frequency, etc.). It is also intended that as a last resort, the disclosed devices may be used to irreversibly damage the offending nerves, preferably without the use of thermal ablation that indiscriminately damages material near the offending nerves, such as collagen in the posterior longitudinal ligament.

SUMMARY OF THE INVENTION

The present invention is directed to methods and devices for the treatment of chronic lower back pain that may result from a degenerated or injured intervertebral disc. In a preferred embodiment, an array of electrodes, along with a pulse generator that is connected to the electrodes, are used to deliver electrical impulses to nociceptive and/or other nerves located within the posterior longitudinal ligament (PLL) of the lumbar spine and the superficial layer of the dorsal aspect of the annulus fibrosus that lies under the PLL. In alternate embodiments of the invention, the energy directed to nerves in the PLL may be from light, mechanical vibrations or thermal energy, or the nerves may be cooled.

According to the invention, the stimulation in this region may reduce back pain in a patient reversibly, adjustably, and with almost complete coverage of the pain-generating region, for example, by interfering with or modulating afferent pain signals to the brain that originate in those nerves. All stimulating electrodes, light sources, vibrators, heaters or coolers are unidirectional, such that the electrodes or other energy-producing devices are located on one side of the insulating material to which they are attached, e.g., a flexible, inert silicone elastomer (such as Silastic™) or similar flexible material, to prevent stimulation to the overlying thecal sac and the nerves contained therein.

Implantation of the stimulator device may involve a two-step process. A temporary array of electrodes or other energy-producing devices (a lead) may first be implanted transcutaneously and attached by wires, or by optical fibers in the case of light sources, to an external (nonimplanted) pulse generator. One or more of such leads are inserted for the trial under sterile conditions under local anesthesia, with or without conscious sedation. The temporary leads have energy-producing or energy-transmitting devices that are disposed linearly along a side of the lead. The temporary leads are straight and thin, as compared to the permanent leads that may subsequently be implanted, in order to facilitate transcutaneous implantation of the temporary leads. Although temporary leads may be placed longitudinally or horizontally, horizontal placement at one or more vertebral levels via a transforaminal approach will be most common. For implantation of the temporary leads, epidurography is used in order to see that the cauda equina and nerve roots are safely negotiated. Whether the lead is temporary or permanent, its implantation is accompanied by intra-operative electrophysiologic monitoring (somatosensory-evoked potential measurement, spontaneous or triggered electromyography, etc.) to assess the functional integrity of the cauda equina and nerve roots and to detect if that functional integrity is compromised during insertion and/or stimulation of the lead(s).

Because of the potential danger of accidentally stimulating the thecal sac and nerves contained therein, the temporary lead is specially designed to prevent accidental rotation of energy-producing or energy-transmitting devices of the lead towards the thecal sac. The sides of the lead preferably comprise fins that protrude from the main body of the lead which, when inserted into the tissue of the anterior epidural space, will prevent rotation and migration of the leads. Furthermore, although the body of the temporary lead may be shaped in a conventional catheter-like cylindrical form, a flat shape with a rounded or curved tip is preferable in order to prevent rotation and to maintain directionality of electrodes or other energy-transmitting devices of the lead toward the PLL. In order to implant such flat and/or finned leads into a suitable position, special percutaneous implantation methods and devices are used. Intraoperative electrophysiological monitoring is also used to confirm that the thecal sac is not being damaged or stimulated by a lead, either during the lead's insertion or when pulses of energy are applied to the lead.

If nerve stimulation via the temporary energy-producing devices is successful in reducing back pain, a permanent array of energy-producing devices is implanted and attached by wires to an internal (implanted) pulse generator, or in the case of the transmission of light they may be connected with optical fibers. The permanent energy-producing devices are generally disposed nonlinearly across the surface of a paddle lead (plate lead or surgical lead). The direction and route of permanent electrode insertion may be chosen based on the implanter's preference and the extent of the pain generating region. The objective is for the energy emitted or transmitted by the energy-producing devices to cross the path of nerves identified as the stimulation target. The permanent paddle leads are specially designed to contour the posterior vertebral column, such that the surface area of the contact electrodes narrows in those regions bound by two pedicles. This configuration also aids in anchoring the leads in place. Similar to temporary leads, permanent leads may be placed horizontally along the width of the posterior annulus of an intervertebral disc and overlying PLL or placed longitudinally along the PLL that spans the distance between one or more intervertebral discs. The length and width of the paddle leads will vary to accommodate the corresponding dimensions of the pain-generating region as measured on CT or MRI in individual patients.

For patients with whom reversible electrical stimulation does not reduce the pain significantly, the invention contemplates that alternate reversible stimulation modalities may succeed in reducing the pain, either alone or in combination with reversible electrical stimulation. Thus, if the implanted device delivers energy to the nerves within the posterior longitudinal ligament and underlying annulus fibrosus via mechanical vibration or light, or if the temperature of the nerves is reversibly modulated or controlled (heated or cooled) using miniature thermoelectric heat pumps that are integral to the lead device, then these alternate stimulation modalities may succeed by virtue of their effects on the nerves through mechanisms other than electrical effects.

The electrodes of the device may also be used as diagnostic aids, to monitor spontaneous activity of the nerves that lie under the electrodes and to correlate that spontaneous activity with independent measurement of spinal movement, of fluctuations in autonomic tone and of pain; to characterize the electrical conductivity of tissue containing the nerves using real-time electrical impedance tomography (EIT); and to perform a diagnostic electrical stimulation in order to evoke potentials such as a P300 event-related potential that is related to the patient's perception of pain. Furthermore, even if the alternate energy modalities are not used to treat the patient, they may also be used as diagnostic aids to characterize the pathophysiology of the offending nerves. For example, laser light emitted by the device may be used for laser Doppler flowmetry, to measure blood flow in the posterior longitudinal ligament and underlying annulus fibrosus, thereby serving as a measure of the local sympathetic tone.

The diagnostic data may then be used to guide selection of parameters for the nerve stimulation using the different energy modalities, even incorporating automatic analysis of the data into a closed-loop system that performs the stimulation autonomously. In particular, the laser Doppler flowmetry may be used to assess the extent to which stimulation of the nerves in the PLL and/or underlying annulus fibrosus, using a particular set of stimulation parameters (amplitude, frequency, pulse width, etc.) or more generally using a particular type of waveform, is either enhancing or inhibiting the activity of the sympathetic nerves, which in turn modulate the activity of nearby nociceptors. Any accompanying decrease in the measured level of pain in the patient can therefore be taken as evidence that the electrical impulses to the sympathetic nerves at least partially relieve the pain, for those stimulation parameters or waveforms. As another example, measured effects of the electrical stimulation on the patient's pain, as a function of the modulated temperature of those nerves, may be used to jointly select the electrical stimulation parameters and applied temperature.

As a last resort, the disclosed devices may be used to irreversibly damage the offending nerves, preferably without the use of thermal ablation that indiscriminately damages material near the offending nerves, such as collagen in the posterior longitudinal ligament. In particular, electrodes of the stimulator may be used to perform non-thermal irreversible electroporation, light energy may be used to damage nerves by photooxidation with or without the use of a photosensitizer, trauma induced by high-amplitude mechanical vibration may be used to deliberately damage selected nerves, and irreversible damage to the nerves may occur following their maintenance at low but non-freezing temperatures. Although thermal ablation may also be used to damage the nerves by joule heating and/or by dielectric heating of proteins, a thermal insulator covers substantially all of the cauda equina or thecal sac, thereby shielding the cauda equina, thecal sac and nerve roots from the heat that could cause damage. For other stimulation modalities, the cauda equina and other sensitive tissue is protected from iatrogenesis using shock absorbing material in the case of mechanical vibration, light shielding in the case of undesired photooxidation, and the conduction/dissipation of unwanted heat in the case of cooling with a thermoelectric heat pump.

Considered as a system, the invention comprises the following components:

1) Specially designed temporary leads (percutaneous type with linearly arranged electrodes and/or stimulation devices involving the delivery of other forms of energy) and permanent leads (paddle leads with generally nonlinearly arranged electrodes and/or other stimulation devices), with the electrodes and/or other stimulation devices situated in a flexible, inert silicone elastomer (such as Silastic™) or similar flexible insulating material, wherein pulses of energy are transmitted from the electrodes and/or other stimulation devices to adjacent tissue unidirectionally.

2) Pulse generators designed for internal (implanted) and for external use that transmit electrical pulses to the electrodes via wires and/or that transmit pulses to stimulation devices involving other forms of energy, and a programmer that controls the pulse generator. The programmer is used to adjust each electrode's electrical pulse rate, duration, amplitude and anode/cathode configuration, as well as each electrode's state of connection or disconnection to the pulse generator. The programmer may also be used to adjust pulses for other stimulation devices that are mounted in the lead. The programmer may provide control signals to the pulse generator using radiofrequency or infrared transmission, and it may also provide power inductively to the pulse generator if the pulse generator is not powered by batteries. The pulse generator may also communicate wirelessly with a separate computer that may serve as a programmer and that may also integrate data that are also received from other non-invasive devices such as scalp electrodes or electrodermal sensors. Diagnostic data from the lead may also be transmitted to the computer, e.g., via the pulse generator, particularly data from an accelerometer, a stress sensor, a thermometer, and the electrodes themselves.

3) Specially designed surgical aides for implantation of the leads, such as a trocar, obturator, stylet, lead blank, introducer cannula, anchoring tabs, and tools used for connecting the lead to the pulse generator.

However, it should be understood that application of the methods and devices is not limited to the examples that are given. The novel systems, devices and methods for diagnosing and treating conditions using the disclosed stimulation devices are more completely described in the following detailed description of the invention, with reference to the drawings provided herewith, and in claims appended hereto. Other aspects, features, advantages, etc. will become apparent to one skilled in the art when the description of the invention herein is taken in conjunction with the accompanying drawings.

Incorporation By Reference

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

BRIEF DESCRIPTION OF THE DRAWINGS

For the purposes of illustrating the various aspects of the invention, there are shown in the drawings forms that are presently preferred, it being understood, however, that the invention is not limited by or to the precise data, methodologies, arrangements and instrumentalities shown, but rather only by the claims.

FIG. 3 shows a posterior-to-anterior view of the lumbar spine, viewed obliquely on the left side of the patient.

FIG. 4 shows a posterior-to-anterior view of the innervation of the posterior longitudinal ligament (PLL) and of the annulus fibrosus of the intervertebral disc that lies adjacent to the PLL.

FIG. 5 shows a percutaneous flat lead and a pulse generator that may be used to stimulate nerves in the posterior longitudinal ligament and underlying annulus fibrosus, according to the present invention. In FIG. 5A, the lead is shown to be a percutaneous flat lead, and in FIG. 5B, a directional indicator is shown to point in the correct direction when the lead has been inserted correctly.

FIG. 8 shows exemplary paddle leads like the ones shown in FIG. 7, except that the leads are shown to also comprise devices that effect stimulation through the application of light, mechanical vibrations, and cooling. Pulse generators for those devices are also illustrated. The leads are also shown to comprise sensors for measuring the physical state of the stimulated tissue. The lead shown in FIG. 8A is intended to be placed horizontally within the anterior epidural space, and the lead shown in FIG. 8B is intended to be placed vertically (longitudinally) within the anterior epidural space. FIG. 8D illustrates use of the lead shown in FIG. 8B to stimulate sympathetic nerves and to thereby indirectly reduce nociception, which is shown to involve stimulating with the lead, measuring the degree of nociception, and measuring the activity of the sympathetic nerves. The invention contemplates measurement data exemplified by FIG. 8E, wherein there is a simultaneous increase of sympathetic activity and decrease in nociception. The invention also contemplates measurement data exemplified by FIG. 8F, wherein there is a simultaneous increase of sympathetic activity and increase in nociception. FIG. 8G illustrates how one selects the lead's stimulation parameters, depending on the extent to which the measurements resemble FIG. 8E versus FIG. 8F.

DETAILED DESCRIPTION OF THE PREFERRED EMBODIMENTS

Figure 1:
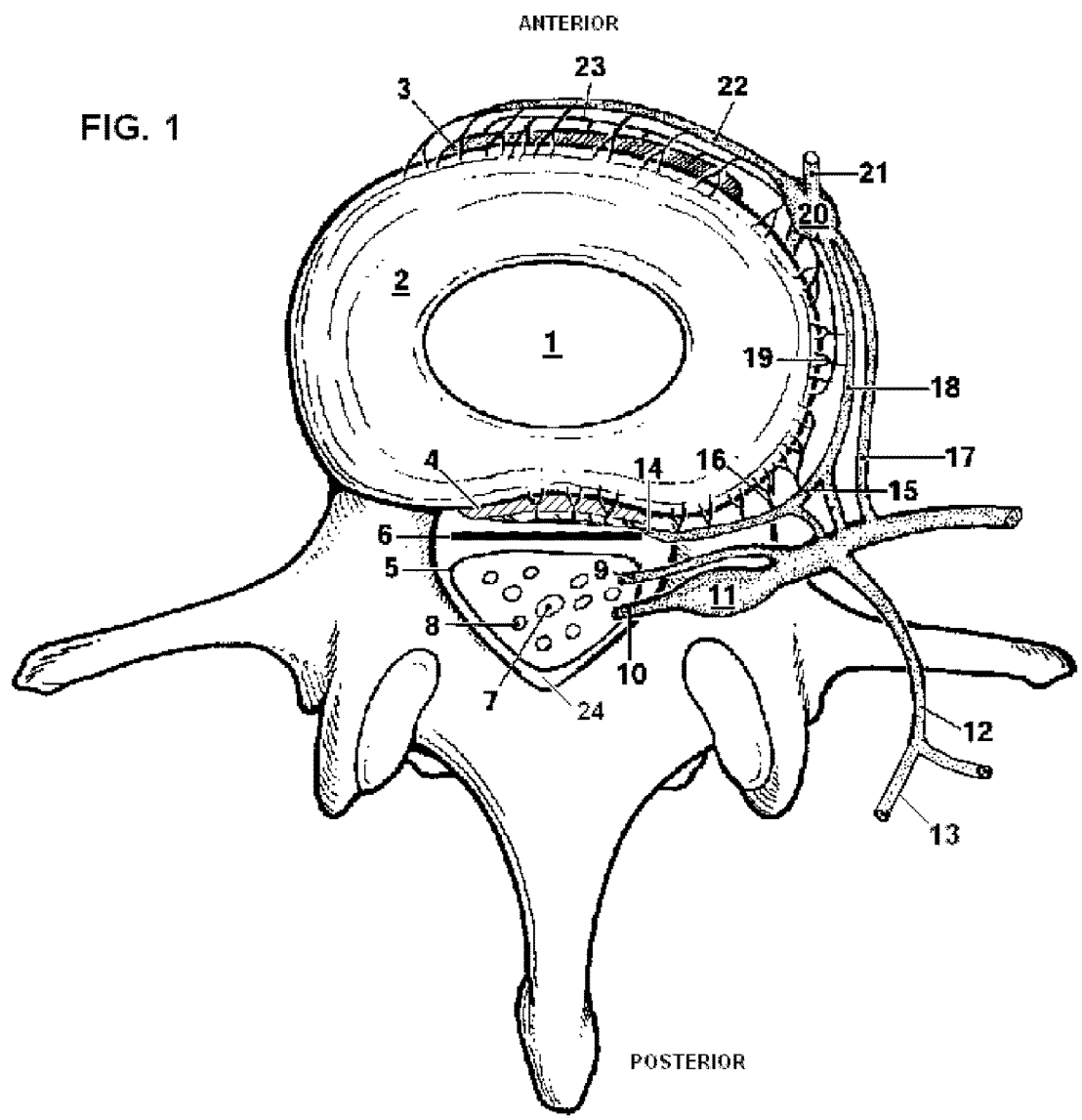
FIG. 1 shows the spine in a cross section perpendicular to its long axis, cut through one of the lumbar discs.
Figure 2:
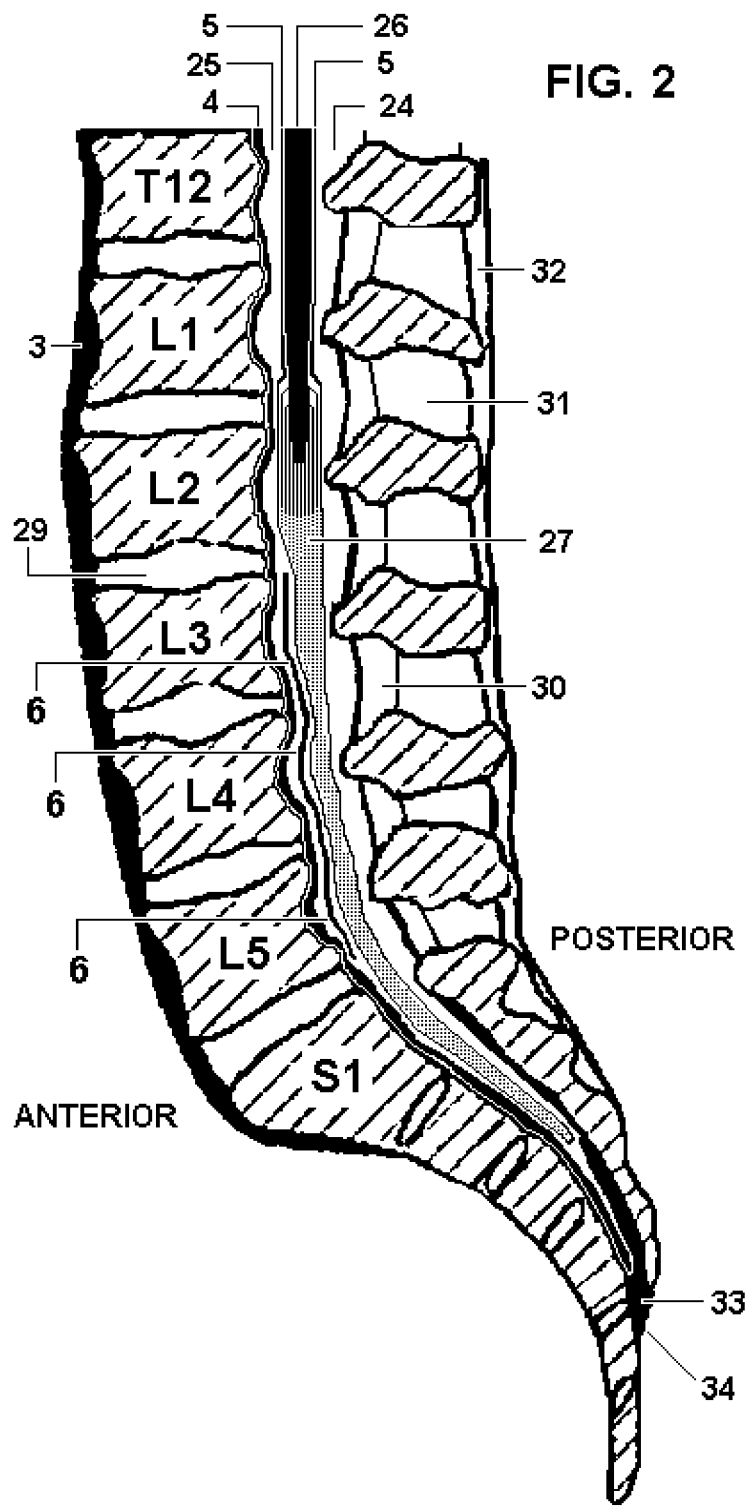
FIG. 2 shows a cross section of the lumbar spine viewed from the side (left-to-right).

FIG. 5 shows an array of electrodes and a pulse generator that may be used to stimulate nerves in the posterior longitudinal ligament and underlying annulus fibrosus, according to the present invention. An array of electrodes is also known as a lead. In FIG. 5A, the lead 60 is shown to be a percutaneous flat lead. The width of the lead may be, for example, 0.5 cm. As shown, it contains eight contact electrodes 61, which are embedded in insulating material 62. For example, the contact electrodes may be made of an alloy of platinum/iridium, and the insulation material may be made of a flexible, inert silicone elastomer (such as Silastic™), polyurethane or silicone/polyurethane. When the lead is rotated by 90 degrees and sectioned along its axis, wires 63 are seen to connect each contact to corresponding connection points in the Pulse Generator 64. The wires 63 may also be embedded in the insulating material 62. For example, the wires may be made of the conducting material 35NLT-DFT-28% Ag or MP35N-DFT-28% Ag. The pulse generator 64 may be powered by batteries, or it may be powered by a radio-frequency driven passive receiver. If the pulse generator is implanted in a patient, it may be programmed through an external transmitter.

When the lead 60 is rotated by 180 degrees to show its back side, the contact electrodes 61 are no longer visible. Instead, the locations above the contact electrodes (shown with dotted lines) are covered by insulating material. Consequently, stimulation with the lead 60 occurs preferentially on one of its sides, namely, the side with exposed contact electrodes 61.

For the invention to function properly, the exposed electrodes 61 should face the posterior longitudinal ligament. This is because it is intended to stimulate nerves in the posterior longitudinal ligament and underlying annulus fibrosus but avoid stimulating other tissue such as the thecal sac. To assist in confirmation that the lead is oriented properly when inserted into the patient, the lead contains one or more radio-opaque directional indicator 65 that may be visualized using fluoroscopy. As shown in FIG. 5B, the directional indicator 65 will point in the correct direction when the lead has been inserted correctly. The insertion of the lead may be horizontal along the intervertebral portion of the PLL 66, or it may placed vertically (longitudinally) along the vertebral portions of the PLL 67, or both. In fact, in addition to the horizontal lead at the L4/L5 disc location, another horizontal lead may be inserted at the L3/L4 disc location or other locations. The vertical lead 67 is shown in FIG. 5B to contain sixteen contact electrodes, which will connect to sixteen corresponding connection points in the pulse generator, but otherwise the longer sixteen-contact lead functions like the shorter eight-contact lead. Other items labeled in FIG. 5B are intervertebral fibers of the posterior longitudinal ligament 48, vertebral fibers of the posterior longitudinal ligament 49, and pedicles (cut) 40.

The percutaneous lead could be cylindrical or, preferably, flat. For purposes of defining flatness, consider a cross section of the lead perpendicular to the long axis of the lead. If that cross section can be represented by about four or fewer connected straight lines and at most one curved line, then the lead is flat along the surface containing the longest straight line. For example, the lead may be rectangular in cross section perpendicular to its long axis, with one side of the rectangle being potentially much longer than its adjacent sides (as in a strap). In either case, it is preferred that the lead will have attached fins 67 (which may also be called wings) that inhibit movement or rotation of the lead from its preferred orientation. For example, FIG. 5B shows such a preferred lead orientation. For present purposes, a fin is defined to be something that resembles a fin in appearance, function, or position relative to the main body of the electrical lead. The preferred embodiment of the lead having fins is most useful when used with methods that are disclosed below in connection with FIG. 6 for inserting and orienting the lead in the patient. The fins 67 are shown in FIG. 5A in the positions that they naturally attain when they are free to move. However, it is understood that the fins 67 are also sufficiently flexible that they may be temporarily bent, approximately flat against the main body of the lead, when the lead with attached fins is inserted into the slightly larger diameter lumen of a needle, cannula, or catheter. Fins have previously been attached to stimulator leads, but not as in the present invention. In U.S. Pat. No. 6,654,644, entitled Pacemaker electrode, to SANCHEZ-ZAMBRANO, a fin is given a serrated edge to facilitate its removal from cardiac tissue. In U.S. Pat. No. 7,894,913, entitled Systems and methods of neuromodulation stimulation for the restoration of sexual function, to BOGGS et al, a fin comprising non-conductive material is shown to focus (reflect) electrical stimulation energy toward a targeted tissue region and away from a non-targeted tissue region. However, in the present invention, the focusing of electrical stimulation is due to the arrangement of electrodes along one side of the lead, not to the presence of the fins. Furthermore, the fins along the side of the lead of the present invention could in principle be made of conducting material, for example, material containing heavy metals that are radio-opaque, which would facilitate imaging of the fins with fluoroscopy. The characteristics of the fins most relevant to the present invention are that the fins should be flexible enough to be temporarily bent during passage through a needle or cannula, but strong enough in the unbent state to withstand rotation when inserted into the anterior epidural space of the patient.

Anatomical considerations related to insertion of a percutaneous lead of the present invention are as follows. A venous plexus surrounded by various amounts of fat almost entirely fills the anterior epidural space. In the thoracolumbar region (T10-L2) the basivertebral vein originates from this venous plexus and extends into the vertebral bodies. As the size of the dural sac relative to the epidural space decreases at the L4-L5 level, the anterior dura falls away from the posterior longitudinal ligament, and fat fills the anterior epidural space. Therefore, the insertion of a lead into the midline of the anterior epidural space will likely encounter decreasing mechanical resistance as one proceeds from L2 to L5. Consequently, if a percutaneous lead is inserted in the vertical (longitudinal) direction, the preferred direction may be from L5 to L3, as shown in FIG. 5B. Depending on the need to change the direction of the distal end of the lead during its insertion, the lead may also be inserted through a needle or cannula having a tip that produces deflected movement of a wire or some other linear element that is inserted through the needle.

Percutaneous entry into the anterior epidural space is accomplished by a transforminal route, or possibly a caudal approach via the sacral hiatus in the case of leads inserted longitudinally. Another possible percutaneous entry route, albeit less likely, is the posteriorlateral interlaminal approach, especially at the level of L5 and S1 for longitudinal lead placement. Percutaneous entry to the anterior epidural space is performed under fluoroscopic guidance, for example in the transforaminal approach, wherein a needle is positioned within a safe zone of the intervertebral neural foramen, most commonly within a region just lateral and cephalad to the margin of the inferior pedicle, dorsal to the vertebral body and caudal to the nerve root (Kambin's triangle), taking care to avoid damage to the nerve root. Endoscopic guidance may also be used in this and subsequent implantation steps.

Figure 6A:
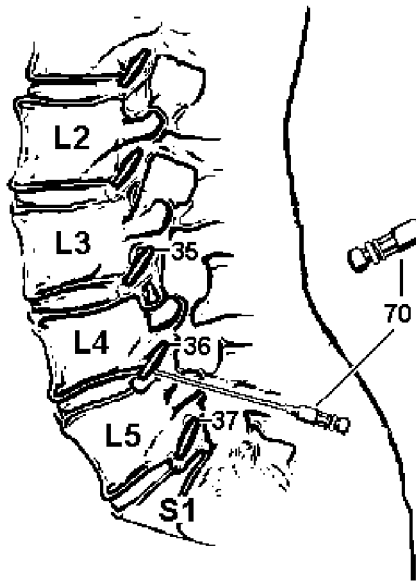
FIG. 6 shows methods and devices for inserting the percutaneous lead of FIG. 5 into the anterior epidural space of a patient. Entry into that space for the L4-L5 disc is shown in FIGS. 6A and 6B, in a side view and in a posterior view, respectively.
Figure 6B:
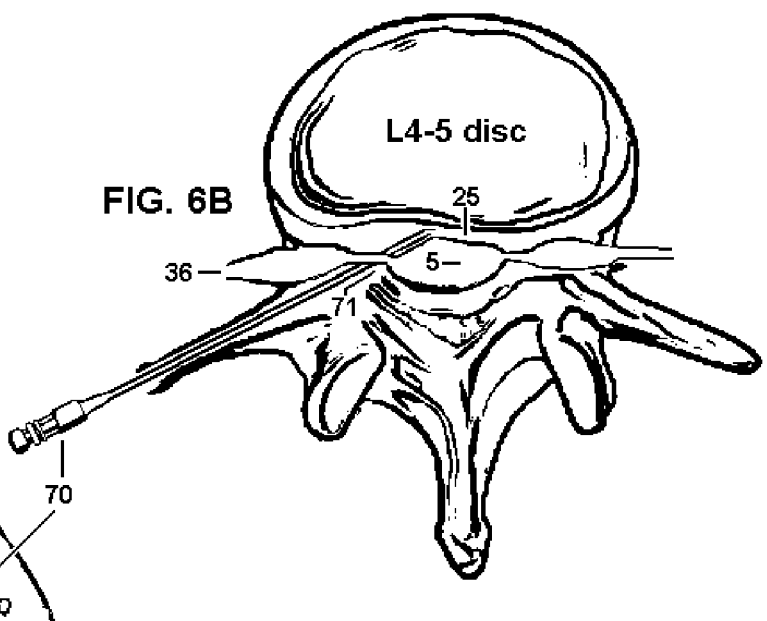

The entry is shown in FIGS. 6A and 6B. Labels in those figures correspond to: Touhy epidural needle 70, anterior epidural space 25, L3 nerve root 35, L4 nerve root 36, L5 nerve root 37, thecal sac 5, and L4-L5 left neural foramen 71. Fluoroscopic contrast agents will ordinarily be injected to traverse the epidural space and outline the dorsal root ganglion, nerve root, and thecal sac, thereby making it possible to visualize a safe insertion of the needle into the anterior epidural space [JOHNSON BA, Schellhas K P, Pollei S R. Epidurography and therapeutic epidural injections: technical considerations and experience with 5334 cases. AJNR Am J Neuroradiol 20 (4, 1999):697-705]. A posterolateral approach is an alternative to the conventional transforaminal approach, in cases where needle tip positioning in the anterior epidural space is difficult [I. S. LEE, S. H. Kim, J. W. Lee, S. H. Hong, J.-Y. Choi, H. S. Kang, J. W. Song, and A. K. Kwon. Comparison of the temporary diagnostic relief of transforaminal epidural steroid injection approaches: conventional versus posterolateral technique. American Journal of Neuroradiology 28 (2007): 204-208].

More specifically, a scalpel is used to make a small incision where the epidural needle will enter the skin. Under fluoroscopy, a Touhy (or similar) epidural needle is inserted as shown in FIG. 6. Entry into the epidural space is confirmed by the ability to blow air into it due to negative pressure within the epidural space. Fluoroscopic contrast agents may be used at this point to assess the location of the tip of the needle relative to the pertinent anatomy such as the nerve root, pedicles, and edge of the thecal sac. A guide wire is then inserted into the lumen of the needle and positioned at the border of the anterior thecal sac and underlying PLL. The needle is then withdrawn, leaving the guide wire in place. A rigid introducer cannula is placed over the guide wire and docked on bone just lateral to the anterior edge of the thecal sac where it meets the posterior spinal column. A flexible introducer cannula may also be used instead. Alternatively, an obturator may be placed in the central opening of the introducer cannula and around the guide wire during initial advancement of the introducer cannula to prevent potential blockage of its lumen by tissues. Once the obturator is removed, fluoroscopic contrast dye can again be used, administered through the cannula, to confirm proper placement of the tip of the cannula. The shape of the cannula and the shape of its lumen is designed to accommodate the shape of the lead: round to accommodate a rounded catheter-like lead and rectangular to accommodate a flat lead which is preferable. The orientation of the tip or bevel of the introducer cannula is known by corresponding markings on the handle of the cannula. Consequently, the orientation of the tip of the cannula and handle is known with respect to the orientation of the lead, once the lead is delivered through the cannula in the desired orientation (i.e., with the electrodes directed downward towards the posterior vertebral column). Once the cannula is confirmed to be in the proper position, the lead can be delivered through the cannula and advanced under fluoroscopy into the anterior epidural space and across the posterior vertebral column, again, making sure that the electrode contacts are directed towards the PLL and away from, or opposite, the thecal sac.

If problems arise in advancing the lead into the anterior epidural space, the route of the lead to its desired final position in the epidural space may be opened (tunneled). In one embodiment of the invention, a flexible lead blank used as a trocar may be passed through the cannula into the anterior epidural space to create a passageway for the placement of the lead. The lead blank is preferably made of a flexible alloy such as Type 304 stainless steel with barium sulfate to make it radio-opaque. The tip of the lead blank is rounded like the true lead to prevent puncturing of the thecal sac during the tunneling process. Once the lead blank has successfully tunneled across the posterior vertebral column in the anterior epidural space, it can be removed and the lead can then be passed into place through the introducer cannula as described above. An alternative method of delivering a temporary lead, especially one with a greater width than 0.5 cm, may include the use of multiple cannulas, each with a larger lumen size than the others, introduced in succession (i.e., one over the other), until the desired lumen size will accommodate the desired electrode lead width. The outside and lumens of such cannulas may have cross-sectional shapes that are not circular (e.g., rectangular). This alternative method may or may not involve the use of a Touhy (or similar) epidural needle and/or guide wire.

Intra-operative electrophysiologic monitoring is performed in order to assure that the lead has not been inserted in the wrong direction and is not defective [Thomas N. PAJEWSKI, Vincent Arlet and Lawrence H. Phillips. Current approach on spinal cord monitoring: the point of view of the neurologist, the anesthesiologist and the spine surgeon Eur Spine J 16 (Suppl 2, 2007): 115-129; MALHOTRA, Neil R and Shaffrey, Christopher I. Intraoperative electrophysiological monitoring in spine surgery. Spine 35 (25, 2010):2167-2179]. Preliminary electrical stimulation is then performed to test operation of the stimulator, confirming that there are no motor responses on the part of the patient at low stimulation voltages. With the lead in place, the introducer cannula is then fully removed. The lead is subsequently secured in place, e.g., by attaching to the patient's skin or possibly to an interspinous ligament. Alternatively, an anchor is used to secure the lead (e.g., U.S. Pat. No. 7,899,553, entitled Lead anchor for implantable stimulation devices, to BARKER). With the lead attached to the pulse generator, the pulse generator is now ready to be programmed to obtain a reduction in back pain, as described below.

Figure 7A:
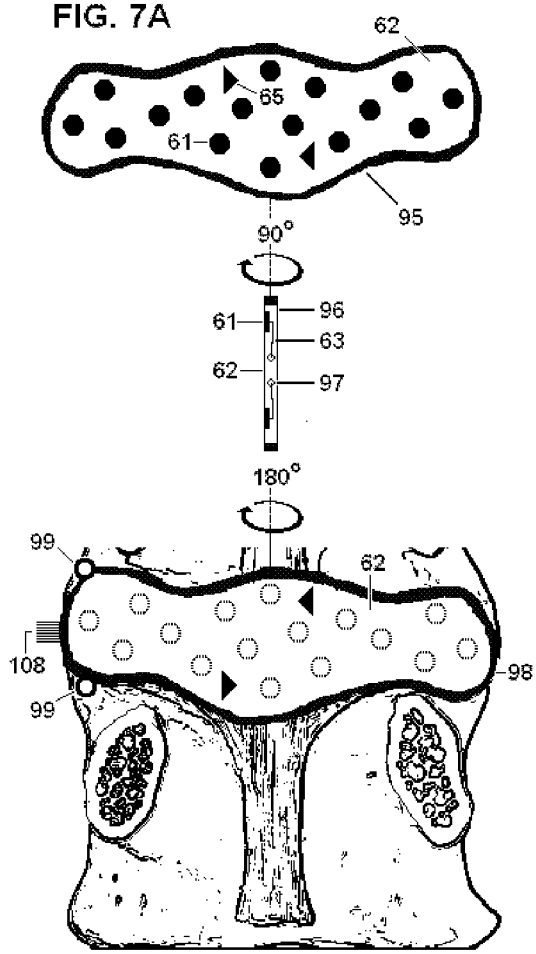
FIG. 7 shows exemplary paddle leads that may be used to stimulate nerves in the posterior longitudinal ligament and underlying annulus fibrosus, according to the present invention. The lead shown in FIG. 7A is intended to be placed horizontally within the anterior epidural space, and the lead shown in FIG. 7B is intended to be placed vertically (longitudinally) within the anterior epidural space.

If a percutaneous lead like the ones shown in FIG. 5 is successful in reducing the patient's back pain after a trial period of typically one or two weeks, replacement of that lead with one capable of simulating a larger surface area would be warranted [NORTH RB, Kidd D H, Olin J C, Sieracki J M. Spinal cord stimulation electrode design: prospective, randomized, controlled trial comparing percutaneous and laminectomy electrodes-part I: technical outcomes. Neurosurgery 51 (2, 2002):381-389]. Such a larger area can be covered by electrodes mounted in a paddle lead (also known as a plate or surgical lead). Two exemplary paddle leads are shown in FIG. 7. The lead shown in FIG. 7A is intended to be placed horizontally within the anterior epidural space, across one of the patient's discs and across nerves within intervertebral fibers of the posterior longitudinal ligament. The lead shown in FIG. 7B is intended to be placed vertically (longitudinally) to stimulate nerves in vertebral fibers of the posterior longitudinal ligament, as well as portions of two (or more) of the patient's discs and intervertebral fibers of the PLL.

Apart from the fact that electrodes in the percutaneous lead shown in FIG. 5 are arranged linearly, which is in contrast to the electrodes in the paddle leads shown in FIG. 7 that are disposed nonlinearly across the surface of the lead, the construction of the percutaneous and paddle leads are similar. In particular, all stimulating electrodes 61 of the paddle leads are unidirectional, such that the electrode contacts are located on one side of the insulating substrate of the paddle 62 that is made of a flexible, inert silicone elastomer (such as Silastic™) or similar material, to prevent stimulation to the overlying thecal sac and the nerves therein. It is advantageous to use a somewhat elastic insulating substrate, in order to accommodate changes in the geometry of the discs that accompany flexion and extension [PEARCY M J, Tibrewal S B. Lumbar intervertebral disc and ligament deformations measured in vivo. Clin Orthop Relat Res (191, 1984):281-286].

Thus, the electrode contacts in FIG. 7A are visible in the view 95. When that view is rotated by 90 degrees, as in the view labeled as 96, a cross section of that rotated view would reveal the electrodes 61, wires 63 that connect the electrode to a pulse generator (64 in FIG. 5), and channels 97 through which those wires run. When the view 95 is rotated by 180 degrees to produce the view labeled as 98, the electrodes are no longer visible. Thus, only the insulating material may be seen from that back side (underlying electrode locations are indicated with dotted lines). The view labeled as 98 also shows how the lead is placed horizontally across one of the patient's discs and across nerves in the intervertebral fibers of the posterior longitudinal ligament and annulus fibrosus, within the anterior epidural space. Radio-opaque directional indicators 65 are also shown to be located within the leads, allowing the orientation of the lead to be visualized by fluoroscopy. Such directional indicators may be redundant if the arrangement of electrodes across the lead is not symmetrical, in which case, the electrodes themselves may also serve as directional markers.

Figure 7B:
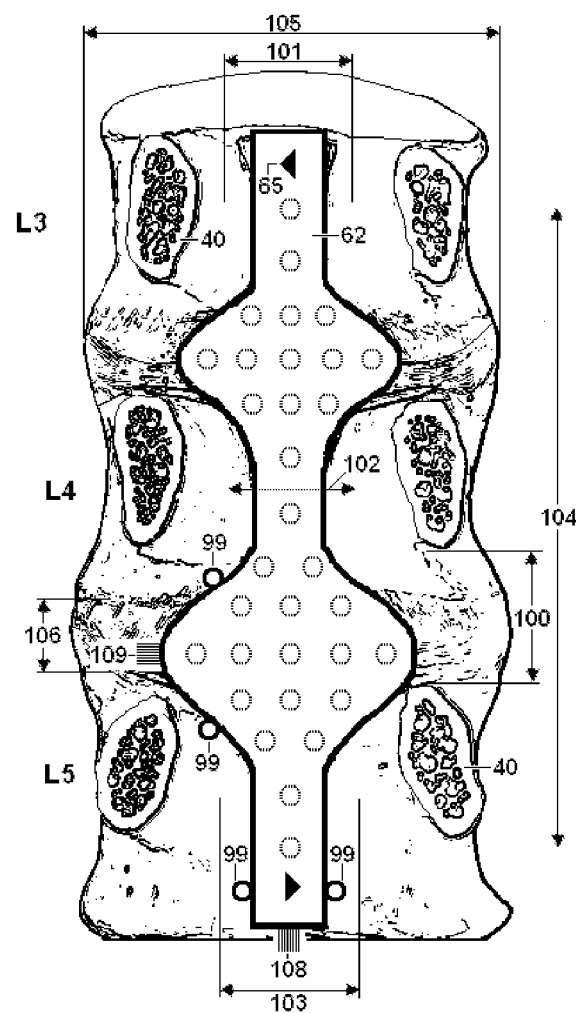

As shown in FIG. 7B, a longitudinal (or vertical or vertebral) lead will widen at the disc spaces to accommodate the posterior lateral margins of the annulus fibrosus. Such permanent paddle electrodes are specially designed to contour the posterior vertebral column so that the surface area of the contact electrodes narrows in those regions bound by two pedicles. This anatomical consideration applies to the horizontal lead shown in FIG. 7A, as well as to the longitudinal lead shown in FIG. 7B. This configuration also aids in anchoring the leads in place. The lead shown in FIG. 7B is shown to contain 32 electrode contacts because it covers a larger surface area than the lead shown in FIG. 7A (with 16 electrode contacts). The length and width of the paddle leads will vary to accommodate the corresponding dimensions of the lumbar discs as measured using CT or MRI imaging. The width of the electrode paddles will be limited to some extent by the distance between two adjacent nerve roots, as estimated from the location of pedicles 40. Thus, the paddle electrodes shown in FIG. 7 differ from presently available spinal cord paddle leads in that the leads of the present invention should be custom fit for each patient (at least within a narrow range of dimensions), otherwise the leads will not fit into the patient properly. The distance between two adjacent ipsilateral nerve roots should approximate the ipsilateral interpedicular distance 100 (1.5-2.5 cm), which is slightly less than the contralateral interpedicular distance (2.0-3.0 cm) that varies according to the particular vertebra: 2.0-2.2 cm for L3 101, 2.2-2.6 cm for L4 102, and 2.6-3.0 cm for L5 103). The space limitation created by the distance between two adjacent nerve roots may warrant two leads to be placed side by side in rare cases requiring wider coverage. The longitudinal (or vertical) lead length 104 will vary depending on the extent and number of discs to be included in the stimulated area (typically 6.0 to 8.0 cm to achieve a distance that spans from L3-L4 to L4-L5 and 8.0 to 9.0 cm if extension from L3-L4 to L5-S1 is required). For comparison, the maximum length of the horizontal lead shown in FIG. 7A will be approximately the distance measured from one side of an intervertebral disc to the other 105 (4.0-5.0 cm), and in the perpendicular direction, the width of the horizontal lead will be approximately the thickness or height of an intervertebral disc 106 (approximately 1.0 cm).

The permanent leads contain small tabs 99 that are used to anchor the lead to bone or other relatively immobile tissue such as the annulus fibrosus, e.g., wherein sutures are passed through the tabs. The electrical connection going from the lead to the pulse generator can be situated at the end of the electrode paddle 108 or on the side of the paddle 109 to accommodate the most suitable region of access for electrode placement.

Direct access to the region via a standard laminotomy or laminectomy approach may be used to insert the paddle lead. Thus, a small window of bone (laminotomy) is drilled over the area using minimally invasive techniques to allow insertion of the electrodes into the epidural space. Other times, more bone must be removed (laminectomy) to allow safe and accurate placement of the electrodes. Such an approach may be accomplished using a minimally invasive or open technique. The laminotomy may be performed, for example, by removing lamina (41 in FIG. 3) of vertebrae L4 and L5, or alternatively between L5 and S1. As an example, the initial steps of Technique 39-20 and its FIG. 39-37 in WILLIAMS and PARK describe a method for gaining access to the anterior epidural space, into which the lead is inserted [Keith D. WILLIAMS and Ashley L. Park. Lower Back Pain and Disorders of Intervertebral Discs. Chapter 39, pp. 2159-2236. In: Campbell's Operative Orthopaedics, 11th edition (S. Terry Canale and James H. Beatty, eds). Philadelphia: Mosby Elsevier, 2007]. A full laminectomy involving one or more levels may also be required in cases in which significant central canal stenosis does not allow adequate space within the anterior epidural compartment to accommodate lead placement. Once placed in the desired location, the lead is then anchored or sutured to firm and relatively immobile tissue or bone to prevent migration or displacement. Because the paddle lead has an extensive flat surface, rotation of the lead is not an issue, and placement of the lead with its electrodes facing the posterior longitudinal ligament (and its insulating back towards the thecal sac) will prevent stimulation of the thecal sac. However, if there is some non-rotational migration of the lead, a snare method may be used to reposition the lead [MACDONALD J D, Fisher K J. Technique for steering spinal cord stimulator electrode. Neurosurgery 69 (1 Suppl Operative, 2011): ons83-86]. The paddle lead may be inserted using an adaptation of the devices described above in connection with the temporary lead, or tools otherwise used for disc surgery may be used, adapted for operation in the anterior epidural space rather than the disc itself [U.S. Pat. No. 6,830,570, entitled Devices and techniques for a posterior lateral disc space approach, to FREY et al]. Once the paddle lead is secured in place, wires from the lead are attached to the pulse generator, and the pulse generator is ready to be programmed to obtain a reduction in back pain, as now described.

The stimulator leads are connected with wires to a pulse generator (implanted or external) that is similar to the ones used for spinal cord stimulation. Examples of such pulse generators are found in U.S. Pat. No. 7,979,126, entitled Orientation-independent implantable pulse generator, to PAYNE et al; U.S. Pat. No. 7,949,393, entitled Implantable pulse generator comprising fractional voltage converter, to VARRICHIO et al; and U.S. Pat. No. 7,930,030, entitled Implantable pulse generator having current steering means, to WOODS et al. Parameters of the pulses that are generated by the pulse generator are selected using a programmer. Examples of programmers are found in U.S. Pat. No. 6,622,048, entitled Implantable device programmer, to MANN et al; U.S. Pat. No. 6,249,703, entitled Handheld patient programmer for implantable human tissue stimulator, to STANTON et al; U.S. Pat. No. 7,359,751, entitled Clinician programmer for use with trial stimulator, to ERICKSON et al; and U.S. Pat. No. 7,738,963, entitled System and method for programming an implantable pulse generator, to HICKMAN et al. Power to the pulse generator is ordinarily from a fully implantable battery, or alternatively from a radiofrequency system, wherein the power is transmitted through the skin by closely applied transmitting coils [U.S. Pat. No. 3,727,616, entitled Electronic system for the stimulation of biological systems, to LENZKES]. As described by LENZKES, the pulse generator may also be programmed via radiofrequency signaling that controls the activation, intensity, distribution, and frequency of electrode stimulation.

The exemplary pulse generator 64 in FIG. 5A shows that each of the electrodes of a lead may be programmed to be either disconnected or connected to the pulse generator. If the electrode is connected, the pulse generator may in principle vary the voltage of each electrode independently, considering the external case of the pulse generator to be a point of voltage reference. In principle, many types of waveforms may be impressed by the pulse generator upon an electrode [A. R. LIBOFF. Signal shapes in electromagnetic therapies: a primer. pp. 17-37 in: Bioelectromagnetic Medicine (Paul J. Rosch and Marko S. Markov, eds.). New York: Marcel Dekker (2004)]. Unlike spinal cord stimulation, the stimulation of the present invention may be performed first with successive small subsets of the electrodes of the lead (e.g., 1 electrode, or 2 or 3 adjacent electrodes), in order to locate the underlying nerves that are causing the back pain. Such a mapping will aid in the subsequent programming of the pulse generator, and it may also be useful for identifying where to ablate nerves in the event that reversible stimulation is not successful. This is not to say that the cumulative pain experienced by the patient is necessarily the simple summation of the pain emanating from individual nerves, because the pain signals from individual nerves may interact with one another to produce greater or lesser pain signals than those from nerves individually. Therefore, the stimulation of small subsets of electrodes of the lead may be followed by simultaneous stimulation of pairs of such subsets, in order to also map the interactions between the underlying nerves.

If the pulse generator is like the ones conventionally used for spinal cord stimulation, it will provide rectangular, biphasic, charge-balanced pulses of adjustable rate and duration to each electrode. For the conventional pulse generator, all electrode contacts connected as anodes will have the same voltage, and all electrode contacts connected as cathodes will have the same voltage. Unipolar stimulation can be applied only if the case of the pulse generator is used as a distant anode. Thus, each electrode is conventionally programmed to have one of three states: disconnected, anode, or cathode [DE VOS C C, Hilgerink M P, Buschman H P, Holsheimer J. Electrode contact configuration and energy consumption in spinal cord stimulation. Neurosurgery 65 (6 Suppl, 2009):210-6]. The states V1, . . . , V8 in the pulse generator 64 in FIG. 5A (and FIG. 8B) represent those states.

As noted above, programming of the pulse generator may be aided by preliminary stimulation involving successive small subsets of the electrodes of the lead, in order to locate the underlying nerves that are causing the back pain. More generally, for a lead containing 16 or 32 electrodes, the number of possible programmed states is very large, in which case, the selection of the programmed state is preferably done with the aid of computer simulation [HOLSHEIMER J. Computer modelling of spinal cord stimulation and its contribution to therapeutic efficacy. Spinal Cord 36 (8, 1998):531-540]. For the present invention, the modeling incorporates knowledge of the electrical properties of the disc and its surrounding tissue [GU W Y, Justiz M A, Yao H. Electrical conductivity of lumbar annulus fibrosus: effects of porosity and fixed charge density. Spine 27 (21, 2002):2390-2395]. See also the disclosure below regarding Laplace's Equation and electrical impedance tomography (EIT). Pulse width is usually set to between 100 to 400 microseconds, but for such modeling, the pulse width is also a variable, which affects the area of coverage [LEE D, Hershey B, Bradley K, Yearwood T. Predicted effects of pulse width programming in spinal cord stimulation: a mathematical modeling study. Med Biol Eng Comput 49 (7, 2011):765-774]. The result of the simulation is a set of programming options, selected to preferentially stimulate nerves in a preselected target volume. After an initial electrode configuration is selected, the configuration may be reprogrammed to optimize its effectiveness, even after the lead is implanted in the patient [MANOLA L, Holsheimer J, Veltink P H, Bradley K, Peterson D. Theoretical investigation into longitudinal cathodal field steering in spinal cord stimulation. Neuromodulation (2, 2007):120-132].

The amplitude of the pulses is typically chosen to be between 0 and 10 V and is set to the smallest value that significantly reduces back pain. Generally, pain relief will be experienced between 2 and 4 V, but this depends on the electrodes that are used. The frequency of the pulse wave is between about 0.01 and 10,000 Hz, typically between 20 and 120 Hz, and is also set to the value that most significantly reduces back pain. It is understood that "Hz" refers not only to sinusoidal cycles per second but also to pulses per second in general.

The stimulation parameters must be adjusted empirically for each patient, so as to reduce the pain. Evidence for a reduction in pain may come from the testimony of the patient, from a decrease in the need for pain medication, from a physical examination that determines painless ranges of movement on the part of the patient, and from many other methods of pain measurement that are described below. Success in reducing pain may be determined within minutes or hours after the stimulation, or it may be gradual over the course of several days or weeks. Thus, there may be an acute reduction in pain, followed by a reduction of pain over the course of days or weeks that is due to adaptation of the nervous system. In preferred embodiments of the invention, the patient is allowed to turn the stimulation on or off as the need arises, and may also adjust parameters of the stimulation to optimize the therapy. The pain might be replaced with paresthesia that may be ignored by the patient. The reason that the stimulation parameters must be adjusted for each patient is related to the fact that the mechanisms responsible for the sensation of pain are complex, and they may vary from patient to patient, as now described.

The afferent nerve fibers in the lumbar posterior longitudinal ligament, the dorsal aspect of the annulus fibrosus, and the connective tissue between the posterior longitudinal ligament and annulus fibrosus are principally mechanosensitive nociceptive fibers, classified into Group III and Group IV types, with a high mechanical threshold for activation.

Most are unmyelinated, and many have free nerve endings. In some studies, it is found that a superficial layer of the nerves is associated with autonomic nerves, and a deeper layer may have a purely nociceptive function. Morbid mechanical stress associated with disc abnormality and chemical stress induced by inflammation may sensitize and stimulate these nociceptive fibers in ways that are not likely under normal conditions. Such abnormal conditions may also cause growth of the nerve fibers in the direction of disc inflammation, mediated by nerve growth factor [SEKINE M, Yamashita T, Takebayashi T, Sakamoto N, Minaki Y, Ishii S. Mechanosensitive afferent units in the lumbar posterior longitudinal ligament. Spine 26 (14, 2001): 1516-1521; PENG B, Wu W, Hou S, Li P, Zhang C, Yang Y. The pathogenesis of discogenic low back pain. J Bone Joint Surg Br 87 (1, 2005): 62-67; COPPES M H, Marani E, Thomeer R T, Groen G J. Innervation of "painful" lumbar discs. Spine 22 (20, 1997):2342-2349; Y. AOKI, K. Takahashi, S. Ohtori & H. Moriya: Neuropathology of Discogenic Low Back Pain: A Review. The Internet Journal of Spine Surgery 2 (1, 2005): 1-9].

Anatomical studies show that the posterior longitudinal ligament contains an abundance of nerve fibers that are thought to convey pain. Posterior longitudinal ligament innervation is most abundant compared to the posterior annulus of the disc and extends beyond the level of the involved disc [EDGAR MA. The nerve supply of the lumbar intervertebral disc. J Bone Joint Surg Br 89 (9, 2007):1135-1139; BOGDUK N, Tynan W, Wilson A S. The nerve supply to the human lumbar intervertebral discs. J Anat 132 (1, 1981):39-56; von DURING M, Fricke B, Dahlmann A. Topography and distribution of nerve fibers in the posterior longitudinal ligament of the rat: an immunocytochemical and electron-microscopical study. Cell Tissue Res 281 (2, 1995):325-338; McCARTHY P W, Petts P, Hamilton A. RT97- and calcitonin gene-related peptide-like immunoreactivity in lumbar intervertebral discs and adjacent tissue from the rat. J Anat 180 (1, 1992):15-24; AHMED M, Bjurholm A, Kreicbergs A, Schultzberg M. Neuropeptide Y, tyrosine hydroxylase and vasoactive intestinal polypeptide-immunoreactive nerve fibers in the vertebral bodies, discs, dura mater, and spinal ligaments of the rat lumbar spine. Spine 18 (2, 1993):268-273; KALLAKURI S, Cavanaugh J M, Blagoev D C. An immunohistochemical study of innervation of lumbar spinal dura and longitudinal ligaments. Spine 23 (4, 1998):403-411; TAKEBAYASHI T, Cavanaugh J M, Kallakuri S, Chen C, Yamashita T. Sympathetic afferent units from lumbar intervertebral discs. J Bone Joint Surg Br 88 (4, 2006):554-557; NAKAMURA S I, Takahashi K, Takahashi Y, Yamagata M, Moriya H. The afferent pathways of discogenic low-back pain. Evaluation of L2 spinal nerve infiltration. J Bone Joint Surg Br 78 (4, 1996):606-612].

The pain signals from the posterior and posterior-lateral annulus fibrosus of the intervertebral disc, as well as the overlying posterior longitudinal ligament, are relayed to the brain via a complex network of nerves. Some of these nerves are sensory branches of the sinuvertebral nerve while others are sympathetic nerves, thus creating a dual pattern of innervation. Furthermore, the network of nerves spans regions above and below the involved disc, which likely explains the common difficulty of localizing discogenic back pain to a single vertebral level. The complexity of the nerve network is such that it is difficult to identify the circuits that are involved in the production of pain, and those circuits may in any event vary from individual to individual [J. Randy JINKINS. The anatomic and physiologic basis of local, referred, and radiating lumbosacral pain syndromes related to disease of the spine. J Neuroradiol 31 (2004): 163-180]. Compounding the complexity is the likelihood that neuropeptide pools in structures such as the dorsal root ganglion may change in response to mechanical or chemical stresses [GRONBLAD M, Weinstein J N, Santavirta S. Immunohistochemical observations on spinal tissue innervation. A review of hypothetical mechanisms of back pain. Acta Orthop Scand 62 (6, 1991):614-622]. Plasticity in the components of the central and sympathetic nervous system that are involved in the sensation of pain also adds to the complexity [KUNER R. Central mechanisms of pathological pain. Nat Med 16 (11, 2010):1258-1266; SCHLERETH T, Birklein F. The sympathetic nervous system and pain. Neuromolecular Med 10 (3, 2008):141-147].

Instead of attempting to address all of those mechanisms, an initial embodiment of the invention focuses on the particular goal of reducing the patient's pain through the enhancement/activation or the blocking of signals in sympathetic nerves within the posterior longitudinal ligament and/or underlying annulus fibrosus. The term sympathetic nerve is used here in the conventional sense to mean a postganglionic efferent nerve that uses norepinephrine (noradrenaline) as the primary neurotransmitter to effect a response in the end organ (with the exception of neurons of sweat glands and chromaffin cells of the adrenal medulla). Notwithstanding the confusingly misleading common informal use of the term "sympathetic afferents", all sympathetic nerves are efferent, because afferent fibers of the autonomic nervous system, which transmit sensory information from the internal organs of the body back to the central nervous system, are not divided into parasympathetic and sympathetic fibers as the autonomic efferent fibers are. Instead, autonomic sensory information may be conducted by general visceral afferent fibers that may run alongside the efferent fibers (e.g., sympathetic fibers), travel up to the ganglion where the efferent fiber synapses (e.g., sympathetic ganglion), continue into the sympathetic trunk, and move into the mixed spinal nerve between the division of the rami and the division of the roots of the spinal nerve. But the afferent pathway then diverges from the sympathetic efferent pathway, by following the dorsal root into the dorsal root ganglion, where the cell body of the visceral afferent nerve is located. When someone uses the informal term "sympathetic afferent" they do not mean that the afferent is actually a sympathetic nerve, but they mean instead that the afferent nerve co-travels with a sympathetic efferent nerve [TAKEBAYASHI T, Cavanaugh J M, Kallakuri S, Chen C, Yamashita T. Sympathetic afferent units from lumbar intervertebral discs. J Bone Joint Surg Br 88 (4, 2006):554-557].

Confusion also arises when nerves are stained using acetylcholinesterase histochemistry, which stains both adrenergic and cholinergic fibers. Investigators who stain nerves using acetylcholinesterase histochemistry warn that " . . . acetylcholesterase activity is not an indication for a cholinergic nature of neurons. For example, noradrenergic nerve elements are also stained. Consequently, somato-efferent and pre- and postganglionic sympathetic, as well as afferent nerve fibers are made visible" [GROEN G J, Baljet B, Drukker J. Nerves and nerve plexuses of the human vertebral column. Am J Anat 188 (3, 1990):282-296]. In view of the comments in the previous paragraph, the fact that such a stained nerve may be traced to a sympathetic ganglion, or otherwise partly exhibits an anatomical course that is characteristic of actual sympathetic nerves, does not imply that the stained nerve is a sympathetic nerve. Thus, if a nerve in the posterior longitudinal ligament is thought to originate from rami communicantes at different levels of the sympathetic trunk, one may not conclude that the nerve is a sympathetic nerve. Similar confusion may arise if a sympathetic ganglion is ablated and that ablation reduces the patient's pain, because the reduction in pain could well be attributed to damage to nerves that co-travel with the sympathetic nerves, rather than to damage to the sympathetic nerves themselves [SCHOTT GD. Visceral afferents: their contribution to 'sympathetic dependent' pain. Brain 117 (Pt 2, 1994):397-413; KOJIMA Y, Maeda T, Arai R, Shichikawa K. Nerve supply to the posterior longitudinal ligament and the intervertebral disc of the rat vertebral column as studied by acetylcholinesterase histochemistry. I. Distribution in the lumbar region. J Anat 169 (1990):237-246; KOJIMA Y, Maeda T, Arai R, Shichikawa K. Nerve supply to the posterior longitudinal ligament and the intervertebral disc of the rat vertebral column as studied by acetylcholinesterase histochemistry. II. Regional differences in the distribution of the nerve fibres and their origins. J Anat 169 (1990):247-255; NAKAMURA S, Takahashi K, Takahashi Y, Moringa T, Shimada Y, Moriya H. Origin of nerves supplying the posterior portion of lumbar intervertebral discs in rats. Spine (Phila Pa. 1976) 21 (8, 1996):917-924; SUSEKI K, Takahashi Y, Takahashi K, Chiba T, Yamagata M, Moriya H. Sensory nerve fibres from lumbar intervertebral discs pass through rami communicantes. A possible pathway for discogenic low back pain. Bone Joint Surg Br 80 (4, 1998): 737-742].

Rather than use acetylcholesterase histochemistry or some other non-specific staining method, one may instead use tyrosine hydroxylase histochemistry to demonstrate catecholamines in the efferent sympathetic nerves, or use some other method that is reasonably specific for the sympathetic nerves, e.g., staining for the C-flanking peptide of neuropeptide Y [Shinji IMAI, Yrjö T Konttinen, Yoshimitsu Tokunaga, Toshihiro Maeda, Sinsuke Hukuda, Seppo Santavirta. Tyrosine hydroxylase-immunoreactive nerve fibres in rat posterior longitudinal ligament. Journal of the Autonomic Nervous System 63 (1-2, 1997): 51-60; AHMED M, Bjurholm A, Kreicbergs A, Schultzberg M. Neuropeptide Y, tyrosine hydroxylase and vasoactive intestinal polypeptide-immunoreactive nerve fibers in the vertebral bodies, discs, dura mater, and spinal ligaments of the rat lumbar spine. Spine (Phila Pa. 1976)18 (2, 1993):268-273; von DURING M, Fricke B, Dahlmann A. Topography and distribution of nerve fibers in the posterior longitudinal ligament of the rat: an immunocytochemical and electron-microscopical study. Cell Tissue Res 281 (2, 1995):325-338; KALLAKURI S, Cavanaugh J M, Blagoev D C. An immunohistochemical study of innervation of lumbar spinal dura and longitudinal ligaments. Spine 23 (4, 1998):403-411; PALMGREN T, Gronblad M, Virri J, Seitsalo S, Ruuskanen M, Karaharju E. Immunohistochemical demonstration of sensory and autonomic nerve terminals in herniated lumbar disc tissue. Spine 21 (1996):1301-1306; PALMGREN T, Grönblad M, Virri J, Kääpä E, Karaharju E. An immunohistochemical study of nerve structures in the anulus fibrosus of human normal lumbar intervertebral discs. Spine (Phila Pa. 1976) 24 (20, 1999):2075-2079].

After using tyrosine hydroxylase histochemistry to stain the posterior longitudinal ligament (PLL) and annulus fibrosus, the observed sympathetic-specific staining pattern may be interpreted in terms of the anatomy of the PLL and underlying annulus fibrosus. The PLL consists of two layers: a deep layer and a superficial layer, and two systems of innervations observed in the PLL correspond roughly to the two layers of the PLL itself. First, many nerve fibers enter the PLL through the superficial layer of the annulus fibrosus. In the deeper layer of the PLL this first nerve fiber network innervates the intervertebral portion of the PLL. Second, in the superficial layer of the PLL, the sinuvertebral nerve bifurcates into ascending and descending branches. These further give rise to transverse branches, which in the midsaggital region form a superficial network. The intervertebral portion is innervated dually by the two networks, but the vertebral portion is innervated only by the superficial network [IMAI S, Konttinen Y T, Tokunaga Y, Maeda T, Hukuda S, Santavira S. An ultrastructural study of calcitonin gene-related peptide-immunoreactive nerve fibres innervating the rat posterior longitudinal ligament: a morphologic basis for their possible efferent actions. Spine, 22 (1997): 1941-1947]. Therefore, when the objective is to preferentially stimulate sympathetic nerves within the PLL and underlying annulus fibrosus, one should preferably use a stimulation method that can do so selectively in regions in which the sympathetic nerves are densest, e.g., to just stimulate nerves in the posterior portion of the annulus fibrosus, or just nerves in the deep PLL, or just nerves in the superficial PLL. Methods for performing that preferential stimulation of sympathetic nerves are disclosed in detail below. In brief, one uses electrical impedance tomography (EIT) to measure the conductivity of the regions containing the nerves, then chooses the amplitude of voltages applied to the lead's electrodes in such a way as to maximize an electric field there, which is calculated using Laplace's equation that incorporates the EIT data.

As described in detail below, the invention also contemplates the simultaneous measurement of sympathetic tone and pain in the patient. For example, the sympathetic tone may be measured as a noninvasive electrodermal response on the patient's feet, and the pain may be measured subjectively using self-reporting or measured objectively using scalp electrodes with an EEG or P300 evoked potential. The measurements are made continuously, and it is expected that data will fluctuate spontaneously. For example, sympathetic tone may exhibit spontaneous oscillations with widely varying periodicities that reflect the regulation such variables as blood pressure and temperature, the best-known of which are Mayer waves. When the sympathetic tone and pain measurements are made, one may find either a positive or negative correlation between them. The correlation may be a cross-correlation that takes into account any time delays accompanying a change in sympathetic tone and the resulting change in the level of pain in the patient (and vice versa). According to the invention, if there is a positive correlation, one would attempt to inhibit the activity of sympathetic nerves in the posterior longitudinal ligament and underlying annulus fibrosus, and if there is a negative correlation, one attempts to increase the activity of sympathetic nerves in the posterior longitudinal ligament and underlying annulus fibrosus. Thus, in the former case, one endeavors to use electrical stimulation (or other forms of stimulation) to block activity of the sympathetic nerves, i.e., prevent the initiation or propagation of action potentials in those nerves, and in the latter case one endeavors to use electrical stimulation to increase activity of the sympathetic nerves, i.e., promote the initiation and propagation of action potentials in those nerves. Beyond the Laplace equation method mentioned above that selectively stimulates sympathetic nerves on the basis of their anatomical location, preferential electrical stimulation of sympathetic nerves within the posterior longitudinal ligament and the underlying annulus fibrosus may make use of any method known in the art, such as preferentially stimulating nerves having axon diameters that most nearly match those of the sympathetic nerves, or exploiting the absolute refractory period of sympathetic nerve axons, or the application of stimulus blocks [GRILL W and Mortimer J T. Stimulus waveforms for selective neural stimulation. IEEE Eng. Med. Biol. 14 (1995): 375-385; John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295].

According to the present invention, the varying role of the sympathetic nervous system in either suppressing or enhancing pain may be understood in part in terms of the variable content of adrenoreceptors in nonicieptors. As a proposed mechanism, in some nociceptors, subtypes of alpha-1 adrenoreceptors may predominate, and otherwise, certain subtypes of alpha-2 adrenoreceptors may predominate. Norepinephrine that is released from the sympathetic nerves would bind to those adrenoreceptors and enhance or inhibit the activity of the nociceptors, respectively. According to this proposed mechanism, in order to minimize pain, electrical stimulation of the sympathetic nerves should attempt to inhibit or enhance activity of the sympathetic nerves, thereby inhibiting or enhancing the release of norepinephrine, depending on the receptor status of the nociceptors that may be inferred from the above-mentioned simultaneous measurement of sympathetic tone and pain. The role of alpha-1 adrenoreceptors has support in this regard, but only for other types of pain [James N. CAMPBELL, Richard A. Meyer, Srinivasa N. Raja. Is nociceptor activation by alpha-1 adrenoreceptors the culprit in sympathetically maintained pain? APS Journal 1 (1, 1992):3-11; DAWSON L F, Phillips J K, Finch P M, Inglis J J, Drummond P D. Expression of α1-adrenoceptors on peripheral nociceptive neurons. Neuroscience 175 (2011):300-314; DONELLO JE, Guan Y, Tian M, Cheevers C V, Alcantara M, Cabrera S, Raja S N, Gil D W. A peripheral adrenoceptor-mediated sympathetic mechanism can transform stress-induced analgesia into hyperalgesia. Anesthesiology 114 (6, 2011):1403-1416]. Thus, this type of mechanism has been described in connection with disorders such as pancreatic cancer, reflex sympathetic dystrophy, causalgia, posttraumatic neuralgia, phantom limb pain and acute herpes zoster, but not in connection with discogenic back pain [Ralf BARON and Wilfrid Janig. Sympathetically maintained pain. Chapter 22. pp. 309-320. In: Pain—Current Understanding, Emerging Therapies, and Novel Approaches to Drug Discovery (Chas Bountra, Rajesh Munglani, and William K. Schmidt, eds.) New York: Marcel Dekker, Inc., 2003].

The proposed role for alpha-2 adrenoreceptor subtypes apparently has no support even for other types of pain, because Applicant is unaware of any situation in which the activation of the sympathetic nervous system is used as a strategy to reduce pain in a patient [Mick SERPELL. The role of the sympathetic nervous system and pain. Anesthesia & Intensive Care Medicine 9 (2, 2008):75-78]. In fact, the converse intervention of attempting to block sympathetic efferent nerves has been a common approach in reducing pain, and detractors of that approach say that the blocking may be ineffective or misinterpreted rather than counterproductive [SCHOTT G D. Visceral afferents: their contribution to 'sympathetic dependent' pain. Brain 117 (Pt 2, 1994): 397-413; VERDUGO R J, Ochoa J L 'Sympathetically maintained pain.' I. Phentolamine block questions the concept. Neurology 44 (1994):1003-1010; Mitchell B. MAX and Ian Gilron. Sympathetically maintained pain: Has the emperor no clothes? Neurology 52 (5, 1999): 905-907; Vaughan G. MACEFIELD. A role for the sympathetic nervous system in sympathetically maintained pain? Clinical Neurophysiology 121 (2010): 996-997]. Activation of the sympathetic nerves as a strategy to reduce discogenic back pain is motivated here by the observation that in patients who are not experiencing pain, that activation may prevent pain that that would otherwise occur [SCHLERETH T, Birklein F. The sympathetic nervous system and pain. Neuromolecular Med 10 (3, 2008):141-147]. A mechanism that may account for that observation is that particular subtypes of alpha-2 adrenoreceptors, such as the alpha-2C subtype, appear to be anti-nociceptive and may be present in afferent nerves [KHASAR S G, Green P G, Chou B, Levine J D. Peripheral nociceptive effects of alpha 2-adrenergic receptor agonists in the rat. Neuroscience 66 (2, 1995):427-432; K. O. ALEY and Jon D. Levine. Multiple receptors involved in peripheral alpha-2, mu, and A1 antinociception, tolerance, and withdrawal. The Journal of Neuroscience 17 (2, 1997):735-744; FAIRBANKS C A, Stone L S, Kitto K F, Nguyen H O, Posthumus I J, Wilcox G L. alpha(2C)-Adrenergic receptors mediate spinal analgesia and adrenergic-opioid synergy. J Pharmacol Exp Ther 300 (1, 2002): 282-290]. During the inflammatory sensitization of the lumbar spine that may co-occur with the development of pain, many changes take place in the composition and physiology of afferent receptors, but if the anti-nociceptive alpha-2 adrenoreceptors persist for an extended period of time during that sensitization, their binding to the norepinephrine that is released by sympathetic efferent nerves may still be available as a method for reducing pain [KOLTZENBURG M, McMahon S B. The enigmatic role of the sympathetic nervous system in chronic pain. Trends Pharmacol Sci 12 (11, 1991):399-402].

As described above, the decision as to whether to attempt to enhance or inhibit the activity of the sympathetic nerves is made according to whether there is a positive or negative correlation (or cross-correlation) between sympathetic tone and pain, in which the sympathetic tone measurement is made so as to correspond to a region that would include the lumbar spine. The present invention discloses additional methods for assessing the extent to which the regional sympathetic tone corresponds to the local sympathetic tone within the posterior longitudinal ligament and the underlying annulus fibrosus. As described in detail below, that assessment makes use of laser Doppler flowmetry to measure continuously the flow of blood in selected locations within the PLL and/or underlying annulus fibrosus. In normal individuals, norepinephrine released from sympathetic nerves onto alpha receptors in blood vessels causes vasoconstriction. Thus, an increase or decrease in sympathetic tone would normally result in a decrease or increase, respectively, in blood flow to the corresponding portion of the lumbar region. Consequently, the measurement of changes in blood flow may normally be used to infer changes in the sympathetic activity that caused the blood flow changes. However, the situation is more complex in tissue that is experiencing inflammation, such that the normal relation between local sympathetic tone and blood flow may become distorted. Therefore, to the extent that the measured local sympathetic tone corresponds to the regional sympathetic tone, the latter may be used in analyzing the relation between sympathetic tone and pain. Otherwise, the local sympathetic tone would be used.

The blood flow measurement using laser Doppler flowmetry may also be used to assess the extent to which stimulation of the nerves in the PLL and/or underlying annulus fibrosus, using a particular set of stimulation parameters (e.g., amplitude, frequency, pulse width, etc.) or waveform type more generally, is either enhancing or inhibiting the activity of the sympathetic nerves. If the assessment is done in a normal individual, the enhancement or inhibition may be inferred from whether the measured blood flow decreases or increases, respectively, following application of the electrical stimulus. Thus, during enhancement, norepinephrine released from the sympathetic nerves onto blood vessels causes vasoconstriction and a decrease of blood flow, and during inhibition, the reduced release of norepinephrine would allow the blood vessels to vasodilate beyond their basal tonic diameters, resulting in increased blood flow. In a patient experiencing inflammation, the magnitude of the blood flow changes may differ from those characteristic of a normal individual and conceivably could even show an anomalous reversal between vasoconstriction and vasodilation [KOEDA T, Sato J, Kumazawa T, Tsujii Y, Mizumura K. Effects of adrenoceptor antagonists on the cutaneous blood flow increase response to sympathetic nerve stimulation in rats with persistent inflammation. Jpn J Physiol 52 (6, 2002):521-530]. Even so, the measurement of any change in blood flow following application of the electrical stimulus would indicate that the electrical stimulation is having a measurable effect on the sympathetic nerves. Any accompanying decrease in the level of pain in the patient could therefore be taken as evidence that the electrical impulses to the sympathetic nerves at least partially relieve the pain, for those stimulation parameters, or waveform type more generally. In this embodiment of the invention, the most effective parameters for electrical stimulation may change over time by virtue of the fact that the inflammation in the patient's lumbar spine is running its course independently, such that changes in receptor composition within the nociceptors would necessitate using different optimal stimulation parameter values (or waveform types more generally) that correspond to those changes.

Electrical stimulation of sympathetic nerves has been disclosed previously, but not to postganglionic efferent nerves in the PLL for purposes of discogenic back pain treatment. For example, REZAI stimulated the lumbar sympathetic ganglia to inhibit nerves there, in order to treat conditions other than lumbar back pain [U.S. Pat. No. 8,046,075, entitled Electrical stimulation of the sympathetic nerve chain, to REZAI; U.S. Pat. No. 6,438,423, entitled Method of treating complex regional pain syndromes by electrical stimulation of the sympathetic nerve chain, to REZAI]. U.S. Pat. No. 7,239,912, entitled Electric modulation of sympathetic nervous system, to DOBAK, discloses the use of electrical stimulation to modulate activity of the sympathetic nervous system, but it is directed to the treatment of obesity and is unrelated to the treatment of pain. Pending application Ser. No. 13/458,697 published as US20120277839, entitled Selective stimulation to modulate the sympathetic nervous system, to KRAMER et al. discloses stimulating a dorsal root ganglion upstream of at least one ganglion of the sympathetic nerve chain, but it is not concerned with discogenic back pain. U.S. Pat. No. 7,890,166, entitled Regional therapies for treatment of pain, to HERUTH et al., teaches the infusion of drugs in conjunction with the implantation of electrodes in two regions of the body, along with electrical stimulation of the two regions limited to two separate low and high frequencies, in which the drug may be the alpha2-adrenergic agonist clonidine. This differs from the present invention because the disclosure here does not involve infusion of any drug, much less infusion of a drug that specifically affects sympathetic nerves, and the use of electrodes is directed here a specific single region (viz., lumbar posterior longitudinal ligament and underlying annulus fibrosus) that can involve a wide range of frequencies and waveforms that specifically modulate sympathetic nerves. U.S. Pat. No. 7,769,442, entitled Device and method for inhibiting release of pro-inflammatory mediator, to SHAFER and U.S. Pat. No. 7,418,292, entitled Device and method for attenuating an immune response, to SHAFER, both pertain to electrically stimulating a sympathetic nerve, particularly the splenic nerve, to modulate an immune response, but they do not pertain to treatment of pain, much less discogenic lumbar back pain.

The sympathetic mechanisms that are disclosed here are also in contrast to the disclosure in pending later-priority application No. U.S. Ser. No. 13/469,880, with publication No. US 20120290059, entitled System and method for electrical modulation of the posterior longitudinal ligament, to BRADLEY. That application does not disclose electrical stimulation of sympathetic nerves in connection with the treatment of discogenic pain. In fact, in the course of prosecuting that application, BRADLEY teaches against a role for sympathetic nerves in the transmission of disc pain, by citing as authority the following publication: BOGDUK N. The innervation of the lumbar spine. Spine 8 (3, 1983): 286-293. That publication states that "The topographic association between the sympathetic nervous system and the nerves supplying the intervertebral discs does not invite the conclusion that these discs are innervated by the autonomic nervous system . . . . Indeed, clinical studies have excluded a role for the sympathetic nervous system in the mediation of back pain." Others investigators also teach away from a role for the sympathetic nervous system in the mediation of pain [SCHOTT G D. Visceral afferents: their contribution to 'sympathetic dependent' pain. Brain 117 (Pt 2, 1994):397-413; VERDUGO R J, Ochoa J L 'Sympathetically maintained pain.' I. Phentolamine block questions the concept. Neurology 44 (1994):1003-1010; Mitchell B. MAX and Ian Gilron. Sympathetically maintained pain: Has the emperor no clothes? Neurology 52 (5, 1999): 905-907; Vaughan G. MACEFIELD. A role for the sympathetic nervous system in sympathetically maintained pain? Clinical Neurophysiology 121 (2010): 996-997]. From the point of view of such teaching away from the presently disclosed mechanism, it is disputable whether reversible electrical stimulation of sympathetic nerves within or near the posterior longitudinal ligament, as taught here, could in principle affect the pain being experienced by the patient.

In summary, the disclosure above is consistent with at least the following mechanisms by which reversible electrical stimulation of the nerves in the posterior longitudinal ligament and underlying annulus fibrosus may reduce discogenic back pain:

(1) The stimulation may cause the nerves in the posterior longitudinal ligament and/or posterior annulus fibrosus to increase the mechanical force threshold above which the nerves generate an action potential. Thus, if there are fewer nociceptive signals from these nerves, the sensation of pain may decrease. (2) The stimulation may cause the sympathetic nerves in the posterior longitudinal ligament and/or posterior annulus fibrosus to suppress the transmission of action potentials originating in the nociceptive nerves in the posterior longitudinal ligament and/or posterior annulus fibrosus. Under normal conditions, the sympathetic nervous system suppresses pain by this mechanism, and the electrical stimulation of the present invention may cause the sympathetic nerves to behave normally. On the other hand, under abnormal conditions, the sympathetic nervous system enhances the transmission of action potentials originating in nociceptive nerves. In that case, the electrical stimulation may cause a decreased enhancement by sympathetic nerves of the transmission of action potentials originating in nociceptive nerves in the posterior longitudinal ligament and/or posterior annulus fibrosus. (3) The stimulation may cause the nerves in the posterior longitudinal ligament and/or posterior annulus fibrosus to decrease their content of substance P and/or vasoactive-intestinal peptide and/or calcitonin-gene-related peptide. These chemicals are associated with inflammatory processes and pain, and their loss may reverse the inflammatory processes and pain.

As noted above, parameters of the pulses are generated by a pulse generator and are selected using a programmer, wherein stimulation parameters must be adjusted empirically for each patient so as to reduce the pain. Procedures are needed in order to characterize the pathophysiology of the patient's offending nerves, as a guide to the selection of parameters that are used to perform the stimulation (waveform type, stimulation amplitude, frequency, etc.). By way of example, consider FIG. 8C, which illustrates how stimulation via the stimulation-lead may cause the nerves in the posterior longitudinal ligament and/or posterior annulus fibrosus to increase the mechanical force threshold above which the nerves generate an action potential. The term "mechanical force threshold" refers to the mechanical force (measured in units of dynes or newtons or a weight) that is needed to cause a mechanico-sensitive nociceptor nerve to initiate and propagate an action potential. For such nerves in the posterior longitudinal ligament, in the absence of any therapeutic protocol, SEKINE et al. reported that force to be in the range of 47.04 +/−15.25 g (which is the same as 46130 +/−14955 dynes, or 0.4613 +/−0.1495 Newtons) [SEKINE M, Yamashita T, Takebayashi T, Sakamoto N, Minaki Y, Ishii S. Mechanosensitive afferent units in the lumbar posterior longitudinal ligament. Spine 26(14,2001): 1516-21].

Figure 8C:
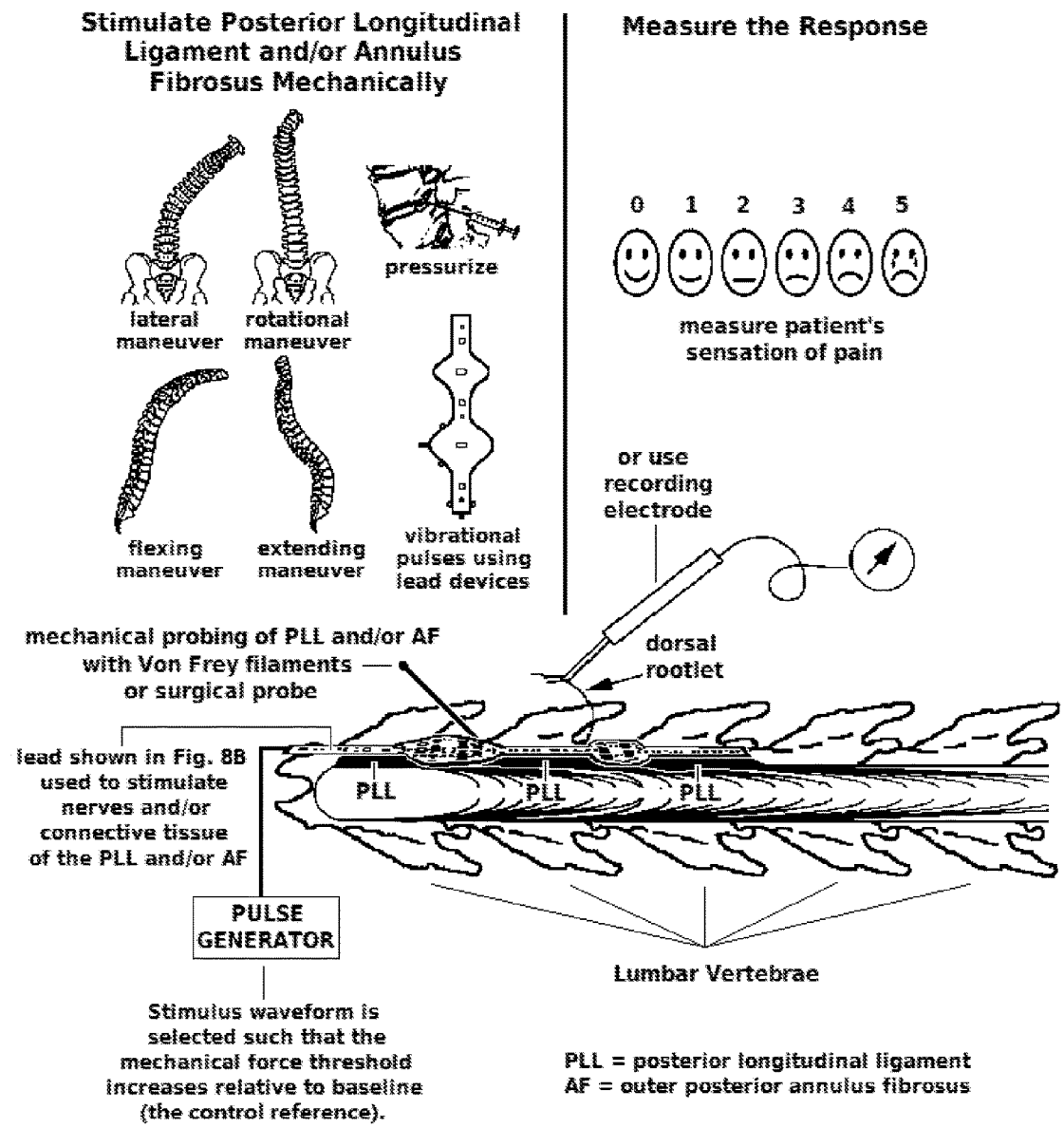
FIG. 8C illustrates use of the lead shown in FIG. 8B to increase the mechanical-force threshold of a nociceptor nerve, which is shown to involve stimulating with the lead, applying mechanical force to the nerve-containing tissue, and measuring the response to that application of mechanical stimulus.

As shown in FIG. 8C, a stimulation lead such as the one shown in FIG. 8B is placed adjacent to the posterior longitudinal ligament and/or posterior annulus fibrosus. A stimulus waveform is then selected via the programmer for the pulse generator, such that the mechanical force threshold is increased relative to the baseline threshold force that existed in the absence of the stimulus waveform.

The waveform selection is made by mechanically stimulating the posterior longitudinal ligament and/or posterior annulus fibrosus and then measuring the response to that mechanical stimulation, before and after applying test electrical impulse parameters to the electrodes of the lead (or other modalities of energy impulses). The stimulation parameters must be adjusted empirically for each patient. As described by SEKINE et al., the mechanical force threshold can be measured by increasing the mechanical force that is applied to the tissue until a significant increased response in nerve activity is observed. SEKINE's method of applying the mechanical force was to probe the tissue with a set of filaments (Von Frey filaments), each of which buckles abruptly when a precalibrated force has been applied. KUSLICH did something similar during the back surgery of more than 700 patients, but he applied the mechanical force using blunt surgical instruments [KUSLICH S D, Ulstrom C L, Michael C J. The tissue origin of low back pain and sciatica: a report of pain response to tissue stimulation during operations on the lumbar spine using local anesthesia. Orthop Clin North Am 22(2,1991):181-187]. Additional methods of applying a quantitatively variable mechanical force to the posterior longitudinal ligament are disclosed herein, including having the patient undergo measured spinal movement maneuvers of lateral movement, flexion, extension, and rotation; pressurizing the tissue through the injection of fluid (discography); and applying controlled vibrational impulses by activating mechanical devices 130 that are found on the lead shown in FIG. 8B (and optionally measuring the resulting strain and stress on the tissue using the devices 150 and 160 that are also shown in FIG. 8B). SEKINE's method of determining that the mechanical threshold had been reached was to use a recording electrode applied to a dorsal rootlet, in order to document the abrupt increase in nerve discharge, relative to the discharge of the nerves to which a sub-threshold mechanical force had been applied previously. KUSLICH's method for measuring the patient's pain-response to mechanical probing was to have the patient self-report painful sensations. Additional methods for quantifying the onset of pain are described below, for patients who are not able to self-report the pain. When the appropriate set of electrical stimulation parameters is found and applied, the original mechanical force threshold will no longer result in the previously observed pain-generating nerve activity. Instead, an increased mechanical force would be required in order to cause the onset of those mechanically-generated, pain-related action potentials.

As another example, consider FIG. 8D, which illustrates the above-mentioned mechanism No. (2), namely, one in which the electrical stimulation may either (a) cause the sympathetic nerves in the posterior longitudinal ligament and/or posterior annulus fibrosus to suppress the transmission of action potentials originating in the nociceptive nerves; or (b) decrease any enhancement by sympathetic nerves of the transmission of action potentials originating in nociceptive nerves in the posterior longitudinal ligament and/or posterior annulus fibrosus. As shown in FIG. 8D, at least two nerve types are associated with the posterior longitudinal ligament and/or posterior annulus fibrosus— nociceptor nerves and sympathetic nerves. The nociceptor nerves connect to a dorsal root ganglion (DRG), and their membrane surfaces contain adrenergic receptors (shown in FIG. 8D to be of the types alpha-1 and alpha-2). The sympathetic nerves connect with the sympathetic chain, and norepinephrine that is released from the sympathetic nerves binds to the adrenergic receptors, thereby causing activity of the nociceptors to be modulated.

As also shown FIG. 8D, a lead such as the one shown in FIG. 8B is positioned adjacent to the posterior longitudinal ligament and/or posterior annulus fibrosus and is used to stimulate sympathetic nerves in those tissues, thereby modulating the release of norepinephrine from the sympathetic nerves, and thereby indirectly modulating the activity of nociceptors via the released norepinephrine. Parameters of the pulses emanating from the lead are generated by a pulse generator and are selected using a programmer, wherein stimulation parameters must be adjusted empirically for each patient so as to reduce the pain.

As noted above, procedures are needed in order to characterize the pathophysiology of the patient's offending nerves, as a guide to the selection of parameters that are used to perform the stimulation (waveform type, stimulation amplitude, frequency, etc.). For the presently-discussed sympathetic mechanism, those procedures involve measuring the relation between the level of sympathetic activity and the degree of nociception (activity of nociceptor nerves). Methods for performing those measurements are well-known in the art. For example, the measured responses shown in FIG. 8C constitute measurement of the degree of nociception. Many methods are also known for monitoring sympathetic activity, such as sympathetic microneurography, use of a microdialysis probe for measuring norepinephrine levels, use of Doppler flowmetry to infer sympathetic activity from blood flow, and the use of chemical- and bio-sensor electrodes for measuring norepinephrine levels.

For purposes of exemplification, assume that the actual measurement data resemble either what is shown in FIG. 8E (simultaneously increasing sympathetic activity and decreasing nociception), or what is shown in FIG. 8F (simultaneously increasing sympathetic activity and increasing nociception). Mechanistically, whether the data would be measured to be like FIG. 8E or like FIG. 8F would depend on the composition of receptor types (shown as alpha-1 and alpha-2 in FIG. 8D) that are found on nociceptors and that bind to norepinephrine that is released by the sympathetic nerves. The release of norepinephrine will in turn depend on whether electrical stimulation by the lead either stimulates or inhibits the activity of the sympathetic nerves. Thus, when some parameter(s) of the electrical stimulation (e.g., stimulation frequency and/or pulse width) is/are systematically varied, there will be a corresponding change in the activity of the sympathetic nerves, which is exemplified by FIG. 8G. According to the invention, to reduce the degree of nociception, one selects the stimulation parameter(s) as indicated in FIG. 8G, depending on the extent to which the actual measurements resemble FIG. 8E versus FIG. 8F.

Because the electrical stimulation parameters are to be selected empirically based upon measurements exemplified by those shown in FIGS. 8E, 8F, and 8G, the invention does not require that the electrical stimulation protocol correspond to any known protocol. On the other hand, there is nothing inherent in the invention that would prevent the use of a known electrical stimulation protocol. Electrical stimulation protocols that either enhance the transmission of action potentials or inhibit the transmission of action potentials (decreasing naturally-occurring enhancement is a form of inhibition) are well known in the art, e.g., as described in GRILL W and Mortimer J T. Stimulus waveforms for selective neural stimulation. IEEE Eng. Med. Biol. 14 (1995): 375-385 and in John E. SWETT and Charles M. Bourassa. Electrical stimulation of peripheral nerve. In: Electrical Stimulation Research Techniques, Michael M. Patterson and Raymond P. Kesner, eds. Academic Press. (New York, 1981) pp. 243-295.

For some patients, reversible stimulation of the nerves of the posterior longitudinal ligament and underlying annulus fibrosus may be unsuccessful in significantly reducing lower back pain (electrically or by other stimulation modalities that are disclosed below). For those patients, the stimulator lead and any implanted pulse generator may be removed. However, before they are removed, a final attempt may be made to reduce the back pain, this time by stimulating the nerves in an attempt to produce irreversible damage to the nerves. It is understood that the term "irreversible" is not synonymous with "permanent," because once the nerves are destroyed, new nerve fibers may eventually grow back into the locations that had been occupied by the destroyed nerve fibers. Consequently, if the irreversible damage to the offending nerves is successful, it may be prudent to leave the stimulator in place for an extended period of time, in the event that newly ingrown nerves may themselves eventually need to be treated or irreversibly damaged by the devices of the invention.

As noted above in the background section, methods and devices have been proposed for irreversibly ablating nerves in the posterior longitudinal ligament, in the following patents or applications: U.S. Pat. No. 6,772,012 and 7,270,659, entitled Methods for electrosurgical treatment of spinal tissue, to RICART et al; U.S. Pat. No. 7,331,956, entitled Methods and apparatus for treating back pain, to HOVDA et al.; and abandoned application U.S. Ser. No. 11/105,274, corresponding to publication No. US20050261754, entitled Methods and apparatus for treating back pain, to WOLOSZKO et al. All of those methods are intended to affect the region of the posterior longitudinal ligament (among other regions) irreversibly, through the application of joule heating. The heating is due to the application of radiofrequency energy (typically 100 kHz to 2 MHz) to the offending area after applying an electrode there. Electrodes of the present invention could in principle also be used for that purpose, although it is understood that electrodes for thermal ablation are best designed specifically for that purpose [Yongmin K I M, H. Gunter Zieber, and Frank A. Yang. Uniformity of current density under stimulating electrodes. Critical Reviews in Biomedical Engineering 17 (1990, 6): 585-619]. The mechanism by which the delivered radiofrequency energy heats and ablates the tissue at temperatures generally at or above 45 C is well understood [HABASH R W, Bansal R, Krewski D, Alhafid H T. Thermal therapy, part 1: an introduction to thermal therapy. Crit Rev Biomed Eng 34 (6, 2006):459-489; DIEDERICH C J. Thermal ablation and high-temperature thermal therapy: overview of technology and clinical implementation. Int J Hyperthermia 21 (8, 2005): 745-753; HAVEMAN J, Van Der Zee J, Wondergem J, Hoogeveen J F, Hulshof M C. Effects of hyperthermia on the peripheral nervous system: a review. Int J Hyperthermia 20 (4, 2004):371-391].

However, it is possible to damage tissue by electrical stimulation mechanisms other than heating, and those are the preferred mechanisms that are used in the present invention [LEE RC, Zhang D, Hannig J. Biophysical injury mechanisms in electrical shock trauma. Annu Rev Biomed Eng 2 (2000):477-509]. In particular, nonthermal irreversible electroporation may be used to damage tissue [DAVALOS R V, Mir I L, Rubinsky B. Tissue ablation with irreversible electroporation. Ann Biomed Eng 33 (2, 2005): 223-231; RUBINSKY B. Irreversible electroporation in medicine. Technol Cancer Res Treat 6 (4, 2007):255-260]. Because nonthermal irreversible electroporation permeabilizes and damages a cell membrane without causing thermal damage, the integrity of molecules such as collagen and elastin in the target region is generally preserved.

In electroporation, a pulse of electric field is generated between two electrodes (preferably first with one polarity, then with the reverse polarity). The damage to cells by electroporation is a function of the electric field strength, the pulse duration, and the number of pulses. To damage the cells, the field should generally be greater than 680 volts per cm (typically 1000 volts per cm), the pulse duration should be 0.5-10 millisec (typically 1.0 millisec) separated by 10 sec to minimize the likelihood of Joule heating. However, muscle and nerve cells might be damaged by electric fields as small as 60 V/cm so in the present invention the electrical field is applied stepwise with increasing V/cm until the intended therapeutic effect is achieved. Damage will occur first to non-myelinated nerves, because the myelin of myelinated nerves protects those nerves [DANIELS C, Rubinsky B. Electrical field and temperature model of nonthermal irreversible electroporation in heterogeneous tissues. J Biomech Eng 131 (7, 2009): 071006, pp 1-12; DAVALOS R V, Otten D M, Mir L M, Rubinsky B. Electrical impedance tomography for imaging tissue electroporation. IEEETrans Biomed Eng 51 (5, 2004):761-767; GRANOT Y, Rubinsky B. Methods of optimization of electrical impedance tomography for imaging tissue electroporation. Physiol Meas 28 (10, 2007):1135-1147; LINDERHOLM P, Marescot L, Loke M H, Renaud P. Cell culture imaging using microimpedance tomography. IEEE Trans Biomed Eng 55 (1, 2008):138-146]. However, there is an abundance of non-myelinated nerves relative to myelinated nerves in the annulus and posterior longitudinal ligament, so the nerve damage will be significant [McCARTHY P W, Petts P, Hamilton A. RT97- and calcitonin gene-related peptide-like immunoreactivity in lumbar intervertebral discs and adjacent tissue from the rat. J Anat 180 (1, 1992):15-24]. One ablative method of the present invention is to perform irreversible electroporation with relatively low electric fields to spare the myelinated nerve fibers, then resume reversible stimulation to neuromodulate their activities as in the preferred embodiment of the present invention. If the resumed reversible stimulation is not successful in reducing the back pain, then irreversible electroporation can be repeated with a higher electric field to ablate all of the offending nerves. As with the reversible stimulation, intra-operative electrophysiologic monitoring is performed in order to assure that the ablation does not harm the thecal sac and nerves contained therein [Thomas N. PAJEWSKI, Vincent Arlet and Lawrence H. Phillips. Current approach on spinal cord monitoring: the point of view of the neurologist, the anesthesiologist and the spine surgeon Eur Spine J 16 (Suppl 2, 2007): 115-129; MALHOTRA, Neil R and Shaffrey, Christopher I. Intraoperative electrophysiological monitoring in spine surgery. Spine 35 (25, 2010):2167-2179].

The electronics of a conventional 0 to 10V pulse generator is adapted to produce such higher voltage electroporation pulses [Abbas POURZAKI and Hossein Mirzaee. New high voltage pulse generators. Recent Patents on Electrical Engineering 2 (2009):65-76]. To irreversibly electroporate (ablate) the entire surface area covered by the lead, pulses may be generated pairwise between many of the electrodes. An advantage of limiting the electroporation pulses to pairs of electrodes within the lead is that it minimizes any pain that the patient may experience from the pulses. If two electrodes of the lead in FIG. 7A are separated by 0.5 cm, then typically a 1 millisecond pulse of 500 V is applied between them. The closer that the electrodes are to one another, then the smaller the applied voltage must be in order to damage the underlying nerve. If the parameters that are used do not reduce the pain, the pulse duration is increased, the voltage is increased (up to the limit of the pulse generator, typically 1000 V), and/or the pulsation continues every 10 seconds until the pain is reduced.

If the electroporation is not successful in significantly reducing the pain, the stimulation parameters may be changed to allow joule heating and dielectric heating of proteins to be additional mechanisms of damage. Thus, in the preferred embodiment of electroporation ablation, pulses are separated by at least 10 seconds to minimize the likelihood of damage from joule heating (i.e., a stimulation frequency of less than or equal to 0.1 Hz). This constraint may then be relaxed such that pulses are delivered at higher frequencies, with or without simultaneous adjustment of the stimulation voltage. As the frequency is increased gradually from 0.1 Hz to 10 kHz, joule heating will increasingly contribute to the mechanism of ablation, provided that the amplitude's voltage is set for a long enough time to a value greater than a voltage that may be used for reversible stimulation. Above about 10 kHz, the dielectric heating of proteins will also contribute as a mechanism of ablation, wherein cellular proteins denature and become unable to function normally. This is because at those higher stimulation frequencies, the cell membrane is no longer an effective barrier to the passage of electrical current, and capacitive coupling of power across each cell membrane permits the passage of current into the cytoplasm [LEE R C, Zhang D, Hannig J. Biophysical injury mechanisms in electrical shock trauma. Annu Rev Biomed Eng 2 (2000):477-509]. Such ablation by dielectric heating of proteins may be attempted up to the highest pulse frequency that can be generated by the pulse generator, typically 20 kHz to 50 kHz. At such frequencies, one of the lead electrodes at a time may serve as an active electrode, and current is collected in a much larger return electrode (dispersive electrode) which may comprise many of the remaining electrodes connected together electrically to the case of the pulse generator, or which may be a separate dispersive electrode if the ablation is being attempted during surgery prior to removal of the paddle lead [Yongmin K I M, H. Gunter Zieber, and Frank A. Yang. Uniformity of current density under stimulating electrodes. Critical Reviews in Biomedical Engineering 17 (1990, 6): 585-619].

In order to effect a controlled thermal ablation, one or more small temperature sensor is mounted on the electrode side of the lead (e.g., thermocouple, thermistor, silicon band gap temperature sensor, resistance temperature detector or other such sensor known in the art) and connected to the pulse generator, which makes a time vs. temperature readout available to the care-giver through the programmer. A thermal dose that is effective in ablating the nerves is applied, which is a function of the measured temperature and duration of heating [HABASH R W, Bansal R, Krewski D, Alhafid H T. Thermal therapy, part 1: an introduction to thermal therapy. Crit Rev Biomed Eng 34 (6, 2006):459-489; DIEDERICH C J. Thermal ablation and high-temperature thermal therapy: overview of technology and clinical implementation. Int J Hyperthermia 21 (8, 2005): 745-753; HAVEMAN J, Van Der Zee J, Wondergem J, Hoogeveen J F, Hulshof M C. Effects of hyperthermia on the peripheral nervous system: a review. Int J Hyperthermia 20 (4, 2004): 371-391]. As with the reversible stimulation and electroporative ablation, intra-operative electrophysiologic monitoring is performed in order to assure that the thermal ablation does not harm the thecal sac and nerves contained therein. A significant difference between such thermal ablation and the methods disclosed in the above-cited patents and patent applications to RICART et al, HOVDA et al, and WOLOSZKO et al. is that in the present invention, the insulation of the lead (62 in FIG. 7) serves not only as electrical insulation, but also as thermal insulation, thus making it possible to direct accumulated applied heat to the posterior longitudinal ligament and posterior annulus fibrosus, and yet shield substantially all of the cauda equina, thecal sac and nerve roots from that heat. For extra thermal protection, an extra layer of thermal insulation (e.g., biocompatible ceramic foam) may be used to coat the side of the lead that is placed nearest the cauda equina.

In addition to the use of reversible and irreversible electrical stimulation to modulate, inhibit or damage the function of nerves in the posterior longitudinal ligament and/or in the underlying annulus fibrosus, the present invention discloses the use of additional stimulation modalities. They comprise the reversible or irreversible stimulation of the nerves using light, the reversible or irreversible stimulation of the nerves using mechanical vibration, and reversible or irreversible changes made to the functioning of the nerves through cooling. These different stimulation modalities may be applied separately or together. Furthermore, as described below, each of these modalities (electrical, light, vibration, and cold) may be applied diagnostically to evoke potentials for purposes of preliminarily evaluating the pathophysiology of the patient's back pain, which may then be used to select parameters of the reversible or irreversible stimulation by any or all of the types of applied energy.

In one aspect of the invention, ultraviolet, visible, or infrared light may be used to stimulate nerves within the posterior longitudinal ligament or underlying annulus fibrosus. The light source will generally be either a laser diode or an LED. The purpose of stimulation of the nerves with light can be to induce either reversible or irreversible effects. Generally, ultraviolet light is used to produce irreversible damage, and light with longer wavelengths (e.g., infrared) is used to produce reversible effects, although brief exposure to ultraviolet light may be reversible and extended exposure to light with longer wavelengths may produce damage. Although the primary use of the light source is stimulation of the nerves, it is understood that the light may also be used to illuminate a field of view for an ultra-miniature camera that is built into the lead to guide implantation, especially a percutaneous lead with the camera positioned near its distal tip. The wavelength of the light source may be selected with this in mind, although for some imagers their response is nearly invariant with respect to wavelength [David G. STORK and Patrick R. Gill. Lensless ultra-miniature CMOS computational imagers and sensors. pp. 186-191 In: Proceedings, Seventh International Conference on Sensor Technologies and Applications (SENSORCOMM 2013), held 25-31 Aug. 2013 in Barcelona, Spain. Red Hook, New York: Curran Associates, Inc., 2013]. Another secondary application of the laser diode is its use to measure blood flow in the tissue that is illuminated by the light, using laser Doppler flowmetry, as described later in connection with the measurement of sympathetic tone. The laser Doppler device may also be used to measure tissue vibrations that are caused by the vibrator that is described later.

The laser diode or LED may be mounted on the stimulation lead device, with attached wires connecting the device to its controller. The controller is generally housed in the same housing used to contain the control circuitry for electrical stimulation, so in what follows the term "pulse generator" is used to describe all such control circuits. Alternatively, the laser diode or LED light source may be situated within the housing of the pulse generator, with the light transmitted via optical fibers that terminate on the stimulation lead device [U.S. Pat. No. 8,701,675, entitled Laser treatment for CNS injury, to SCHENKER et al., which describes leads having a diameter of about 3 to 6 mm]. The light that emerges from either the lead-mounted light source or the optical fibers is then directed to the posterior longitudinal ligament and/or underlying annulus fibrosus, when the lead device is implanted into the anterior epidural space. The area of light coverage is determined by the number of optical elements on the lead, as well as the lenses, mirrors and diffusers used to terminate those optical elements. Generally, the lenses, mirrors and diffusers will be selected to maximize the area of tissue that is stimulated with the light. The depth of penetration of the light into the tissue depends on its wavelength, with light at some infrared wavelengths being able to penetrate a centimeter or more into the tissue.

Direct mounting of the light source into the lead device has the advantage of simplicity, such that all connections between the lead and pulse generator use electrical wires. However, the number of presently available light sources that are sufficiently small (preferably less than about 3 mm in diameter) to be mounted advantageously in a percutaneous lead is relatively limited. By way of example, the CSL701/801 series of LEDs from ROHM Semiconductor measure 2.4 mm×2.9 mm×3.1 mm, and the Model DL 7891SX 780 nm diode laser from Creative Technology has a 3.3 mm diameter [ROHM Semiconductor U.S.A., LLC 2323 Owen Street, Santa Clara, Calif. 95054; Creative Technology Lasers 180 Alderwood Road, Walnut Creek, Calif. 94598-1042]. To keep the diameter of the lead device as small as possible, unnecessary portions of the light source may be grinded, milled, sanded, and/or polished before assembly of the lead device. Somewhat larger light sources might be mounted into a paddle lead, such as the Model RLU4116E ultraviolet laser diode from Roithner LaserTechnik, which has a more standard diameter of 5.6 mm [Roithner LaserTechnik GmbH. Wiedner Hauptstrasse 76, Vienna, Austria. Nov. 29, 2012. pp. 1-4]. Even so, to keep the thickness of the paddle lead device as small as possible, unnecessary portions of the light source may be grinded, milled, sanded, and polished before assembly of the lead device.

However, there are advantages to situating the light source within the housing of the pulse generator, with the light transmitted via optical fibers that terminate on the stimulation lead device. First, that permits the use of a much wider range of available light source sizes [Laser Diode catalog. Roithner LaserTechnik GmbH. Wiedner Hauptstrasse 76, Vienna, Austria. Jun. 26, 2014. pp. 1-119]. Second, passive or active fiberoptic combiners and splitters may be used to direct light from a single light source to multiple locations on the lead device, and multiple light sources may be used to illuminate a single location on the lead device. In the latter case, the multiple light sources may have different wavelengths, and the user may decide to use any or all of those sources at a particular instant. By way of example, the fiberoptic combiner and splitter may be in the shape of a Y and have fused fiber elements, in which light applied to the base of Y appears at the two arms at the top of the Y, or two light sources applied to the two top arms of the Y cause light from both sources to combine at the base of the Y. If the Y is inverted and is attached to a non-inverted Y, such that the inverted and non-inverted Ys are attached at their bases, two light sources may be used as input to the arms of one of the Ys, and the combined output would appear in both arms of the other Y. Thus, when one or the other light source is turned on, its output would appear simultaneously at two locations of the combiner/splitter, allowing the operator to select the light source (e.g., wavelength) at more than one location on the lead. It is contemplated that such a splitting/combining design is to be used for many more than two sites on a lead and for more than two selectable light sources (i.e., using more complicated geometries than a Y).

The light source that is selected depends on the effect that one is attempting to produce. Much is known about the interaction of light with tissue, although relatively few investigations have been concerned with the effects of light specifically on nerves [Kendric C. SMITH. Laser and LED photobiology. Laser Therapy 19.2 (2010):72-78]. Many of the early applications of light therapy were intended to damage cells using ultraviolet light, including nerves. Ultraviolet light induces a decrease in membrane sodium permeability, leading to membrane injury in the nerve [Philip E. HOCKBERGER. A history of ultraviolet photobiology for humans, animals and microorganisms. Photochemistry and Photobiology, 76 (6, 2002):561-579]. As a result, free nerve endings are lost [RODRIGUEZ AL, Stefani F S, de Oliveira Praes C E, Piaceski A, Oliveira M P, Martins P, da Silva V D, Bonorino C, Bauer M E. Effects of ultraviolet radiation on human cutaneous nerve fibres. Cell Prolif 42 (4, 2009): 562-567]. Other damage may be done to nucleic acids within the nerve cell through photo-oxidation, including DNA damage. These mechanisms may involve the absorption of light by endogenous photosensitizers, followed by the chemical reactions that ultimately result in the cellular damage [WONDRAK G T, Jacobson M K, Jacobson E L. Endogenous UVA-photosensitizers: mediators of skin photodamage and novel targets for skin photoprotection. Photochem Photobiol Sci 5 (2, 2006):215-237].

If one is attempting to use ultraviolet light to damage the nerve cells in the posterior longitudinal ligament and underlying annulus fibrosus, one may enhance the effect with the use of a photosensitizer that is administered to the patient. In particular, one may use psoralen plus UV-A light (PUVA) therapy. For example, using this method 30 mg of the oral psoralen derivative methoxsalen is administered to the patient 75 minutes before ultraviolet light from the lead is administered to the patient. The ultraviolet light is then administered for typically 5-15 minutes, during which time the effect on the patient's back pain is measured. The entire procedure is performed in a darkened room having no extraneous source of ultraviolet light, so that physiological effects are limited to the immediate vicinity of the lead, with the lead itself shielding the thecal sac and nerve roots from exposure to the light. The patient remains in a light-protected environment for up to 8 hours thereafter, considering that the half-life of psoralen compounds is on the order of 2 hours.

Stimulation of the nerves in the posterior longitudinal ligament and underlying annulus fibrosus may also make use of wavelengths that are intended to produce reversible effects that reduce pain, which has been investigated in the field of low level light therapy. The wavelengths in those applications are generally in the infrared [Ying-Ying HUANG, Aaron C.-H. Chen, James D. Carroll and Michael R. Hamblin. Biphasic dose response in low level light therapy. Dose-Response 7 (2009):358-383; Michael R HAMBLIN and Tatiana N Demidova. Mechanisms of Low Level Light Therapy. Proc. of SPIE 6140 (2006): 614001, pp. 1-12; CHUNG H, Dai T, Sharma S K, Huang Y Y, Carroll J D, Hamblin M R. The nuts and bolts of low-level laser (light) therapy. Ann Biomed Eng 40 (2, 2012):516-533; HASHMI J T, Huang Y Y, Osmani B Z, Sharma S K, Naeser M A, Hamblin M R. Role of low-level laser therapy in neurorehabilitation. PM R 2 (12 Suppl 2, 2010):S292-305]. A very useful aspect of this embodiment of the invention is its ability to potentially reduce inflammation, independently of light-induced effects on the nerves that are related to their ability to initiate and propagate action potentials.

It is contemplated that stimulation of the nerves with light may also be performed in conjunction with the stimulation of those nerves electrically, with mechanical vibration, and/or with the modulation of temperature. DUKE et al. suggested that it is beneficial to combine light and electrical stimulation, but combinations of the other stimulation modalities apparently have not been heretofore disclosed [DUKE A R, Cayce J M, Malphrus J D, Konrad P, Mahadevan-Jansen A, Jansen E D. Combined optical and electrical stimulation of neural tissue in vivo. J Biomed Opt 14 (6, 2009):060501, pp. 1-3].

In another aspect of the present invention, the nerves of the posterior longitudinal ligament and/or underlying annulus fibrosus are subjected to mechanical energy in the form of vibrations. Investigations concerning the effect of mechanical vibration on back pain have given contradictory results. Low frequency vibrations that are encountered in the workplace, particularly vibrations in the range of 2 to 11 Hz near the resonant frequency of the spine, have been shown to increase the risk of disc-related back pain [Taryn E. HILL, Geoffrey T. Desmoulin, Christopher J. Hunter. Is vibration truly an injurious stimulus in the human spine? Journal of Biomechanics 42 (2009): 2631-2635]. Vibration at higher frequencies up to 200 Hz for as little as 10 minutes have been shown to have an effect on the expression of extracellular matrix genes in tissue of the spine, particularly if the vibration amplitude is sufficiently high. Nerve damage caused by vibration may result in changes in gene expression even after the vibration has stopped, in a so-called conditioning lesion that may lead to re-growth of the damaged nerve [WIDERBERG A, Bergman S, Danielsen N, Lundborg G, Dahlin L B. Nerve injury induced by vibration: prevention of the effect of a conditioning lesion by D600, a Ca2+ channel blocker. Occup Environ Med 54 (5, 1997): 312-315]. Consequently, in the present invention, if vibration is being used initially to deliberately damage the nerves causing pain, subsequent vibration may be applied to prevent the regeneration of those pain-causing nerves.

On the other hand, vibration in the range of 80-120 Hz with a displacement of up to 5 mm has also been shown to reduce self-reported neck pain, although the vibrations were directed to whole vertebrae, not to particular nerves [DESMOULIN G T, Yasin N I, Chen D W. Spinal mechanisms of pain control. Clin J Pain 23 (2007):576-585]. Mechanical vibrations have also been directed to the treatment of low back pain [LUNDEBERG T, Nordemar R, Ottoson D. Pain alleviation by vibratory stimulation. Pain 20 (1, 1984):25-44; ANONYMOUS editor. Vibration therapy for pain. Lancet. Jun. 20, 1992:1513]. However, none of those applications of vibration have been performed invasively, none used frequencies greater than 400 Hz, and none were directed specifically to nerves within the posterior longitudinal ligament or the underlying annulus fibrosus.

Sub-ultrasonic implantable vibration devices have been disclosed for treating spinal pain, but by stimulating nerves only indirectly via conduction of vibrations through bone in the spine [U.S. Pat. No. 8,657,765, entitled Analgesic implant device and system, to ASFORA]. Direct mechanical vibration of spinal soft tissue containing nerves apparently has not been disclosed heretofore. Furthermore, in the present invention, the device causing the vibration is intended to be mounted on, or integral to, the lead that is inserted into the anterior epidural space of the patient. The vibration devices disclosed by ASFORA are far too large for mounting in or on a stimulation lead, because they are shown to be implanted in a space between spinous processes of a vertebra. More suitably sized vibration devices are the ones used in smartphones [ShreHarsha RAO. High-definition haptics: Feel the difference! Texas Instruments Analog Application Journal. 3Q 2012:29-32]. However, such devices, e.g., piezo actuators, are limited in the frequency range over which they operate. Nevertheless, electric motors, solenoid vibration devices, etc., that vibrate over a larger range of frequencies and that also have suitably small sizes might be designed to fit on or in a lead.

In the present application, in a preferred embodiment, the vibration device is adapted from an acoustic speaker (receiver) that is designed for very small in-the-ear-canal hearing aids. For example, the WBFK-23990-000 hearing aid receiver that is available from Knowles Electronics (1151 Maplewood Drive, Itasca, Ill. 60143) is an undamped, tubeless magnetic balanced armature receiver that operates over a frequency range of about 10-10,000 Hz and has a size of 5 mm×2.73 mm×1.93 mm. The speaker is placed with its long axis within the body of the stimulator lead, with one end connected to two wires that supply power and signals (via the pulse generator) and with the other end at which sound vibrations appear either contiguous with the body of the lead (to vibrate the lead itself), or attached to a small 45 degree acoustic mirror to direct the sound vibrations perpendicular to the long axis of the lead into an acoustic membrane touching the tissue. The acoustic mirror may be a triangular piece of steel with a width governed by the width of the speaker, attached at its lowest edge to the speaker and with a diaphragm acoustic membrane stretched from the top of the triangle to the speaker, with the membrane made of a strong but waterproof flexible material such as boPET, beryllium or titanium. Alternatively, the diaphragm of the speaker itself may be placed in contact with the tissue that is to be vibrated, which would involve a modification of the speaker, but that would also reduce its size [Mead C. KILLION. Hearing aid transducers. Chapter 166, In: Encyclopedia of Acoustics, Malcolm J. Croker, ed. New York: John Wiley and Sons, 1997, pp. 1979-1990].

The frequency and amplitude of the vibration may be selected by varying the corresponding electrical signal that drives the speaker. Once the lead device is implanted, the frequency and amplitude of the vibrations are varied systematically, and the effect on the patient's pain is measured. Short-term vibration is expected to cause reversible effects, but long-term exposure to vibration may cause irreversible effects. For example, if the vibration amplitude is set at the equivalent of 85 dB continuously for several hours, the nerves may become irreversibly damaged. The movement of the vibrated tissue itself may be monitored using the laser Doppler flowmeter device that is described below, wherein the tissue vibration would otherwise be regarded as a movement artifact from the point of view of flowmetry.

Vibration damping material is applied to the side of the lead opposite the vibration-producing device, in order to prevent mechanical damage to the thecal sac. As noted earlier, that side of the lead may be coated with ceramic foam as a thermal insulator. Ceramic foams can be made in a way that is similar to the creation of polyurethane foams, with open cell walls forming reticulated channels through the foams, thereby acting as sound and vibration dampers, as well as thermal insulators [Jorge P. ARENAS, and Malcolm J. Crocker. Recent Trends in Porous Sound-Absorbing Materials. Sound & Vibration. July 2010: 12-17].

It some embodiments, the mechanical vibrations are applied simultaneously with electrical or other modes of stimulation [GUIEU R, Tardy-Gervet M, Roll J. Analgesic effects of vibration and transcutaneous electrical nerve stimulation applied separately and simultaneously to patients with chronic pain. Can J Neurol Sci. 18 (1991): 113-119]. In the present invention, the frequencies of mechanical vibration and electrical stimulation (or light stimulation) are preferably set to be a multiple of one another, in order to enhance one another's effect. The vibration may also be combined with variation of temperature as follows. In Reynaud's phenomenon, a hyper-activation of the sympathetic nervous system causes extreme vasoconstriction of the peripheral blood vessels that affects the fingers. It may be produced when vibration is absorbed, causing mechanical damage to blood vessels and regulatory nerve elements. When exposed to cold temperatures, the blood supply then becomes markedly reduced. This phenomenon is not known to occur in the disc, but according to the present invention, it may be induced there first by applying vibrations to nerves within the posterior longitudinal ligament and underlying annulus fibrosus, and then by reducing the local temperature there, so as to evoke over-sensitivity to cold. In patients who are successfully treated by that method, the effect will be numbness or paresthesia, without producing pain.

In another aspect of the invention, the cooling of nerves in the posterior longitudinal ligament and/or in the underlying annulus fibrosus is used to modulate or inhibit the activity of those nerves. The cooling may result in reversible or irreversible changes in the nerves, depending on the way in which the cooling is applied. The cooling may also be performed in conjunction with other stimulation modalities, including electrical, mechanical-vibration, and light stimulation, in which the cooling of even a few degrees alters the response of the cells to those other stimulation modalities.

It has long been known that the conduction of myelinated nerves is completely but reversibly blocked at 5 to 7 degrees C. At about 4 degrees C., the smaller C fibers are also blocked. After 15 minutes of cooling, it may take an hour for the nerve blocking effect to reverse [D. N. FRANZ and A. Iggo. Conduction failure in myelinated and non-myelinated axons at low temperatures. J Physiol 199 (2, 1968): 319-345; John E. SWETT and Charles M. Bourassa. Electrical stimulation of peripheral nerves. Chapter 10, pp. 244-295. In: Electrical Stimulation Research Techniques (Michael M. Patterson and Raymond P. Kesner, eds). New York: Academic Press, 1981].

Interpretation of the changes that occur following nerve cooling is complicated by circulatory changes that may also accompany cooling. Such changes may be monitored using the laser Doppler flowmeter that is described below. Furthermore, even though the electrophysiology of the nerve appears to be normal after a cooling block has reversed, the microanatomy of the nerve may have been altered [BASBAUM CB. Induced hypothermia in peripheral nerve: electron microscopic and electrophysiological observations. J Neurocytol 2 (2, 1973):171-187; JIA J, Pollock M. The pathogenesis of non-freezing cold nerve injury. Observations in the rat. Brain 120 (Pt 4, 1997):631-646; JIA J, Pollock M. Cold nerve injury is enhanced by intermittent cooling. Muscle Nerve 22 (12, 1999):1644-1652]. Nevertheless, focal cooling of the brain to a range of temperatures 5-25 C, in order to prevent epilepsy, has been performed successfully in individual animals over a period of many months without significant complications, so it is expected that the long-term application of cooling to the nerves in the posterior longitudinal ligament and/or underlying annulus fibrosus may also be undertaken successfully [ROTHMAN S M. The therapeutic potential of focal cooling for neocortical epilepsy. Neurotherapeutics (2, 2009): 251-257].

Furthermore, the reduction of temperature of a nerve by only a few degrees, which would not produce significant damage to the nerve, may also have a significant effect on the electrophysiology of the nerve [PATBERG WR, Nijmeijer A, SchutJ K, Versprille A, Zock J P, Zijlstra W G. Effects of local nerve cooling on conduction in vagal fibres shed light upon respiratory reflexes in the rabbit. Pflugers Arch 421 (2-3, 1992):280-282]. Such cooling by may be particularly useful in conjunction with nerve stimulation using one of the energy modalities disclosed here (electrical, mechanical-vibration, light) [ACKERMANN D M, Foldes E L, Bhadra N, Kilgore K L. Nerve conduction block using combined thermoelectric cooling and high frequency electrical stimulation. J Neurosci Methods. 193 (1, 2010): 72-76].

Any type of cooling device could be used in the present application, but thermoelectric (Peltier) coolers are preferred because they have no moving parts. The thermoelectric cooler has a cold side and a hot side, and two wires per thermoelectric device are used to connected to it to a power source (here, connection to the pulse generator) [BELL L E. Cooling, heating, generating power, and recovering waste heat with thermoelectric systems. Science 321 (5895, 2008): 1457-1461; CHEN, A. and P. K. Wright. Medical applications of thermoelectrics. Chapter 26, pp. 26.1-26.22 In: Thermoelectrics and Its Energy Harvesting (D. M. Rowe, ed). Boca Raton: CRC Press, 2012]. In the present application, the cold side of the thermoelectric cooler is applied to the surface of the posterior longitudinal ligament in the anterior epidural space, and heat is removed from the opposite hot side of the thermoelectric cooler. The size of the cooler must be sufficiently small to be mounted in the lead device. Examples of the thermoelectric devices that may be used with a percutaneous lead are the 2 mm×1 mm×1.1 mm model MPC-D403/4 from Micropelt GmbH. Emmy-Noether Strasse 2, 79110 Freiburg, Germany, and the 2 mm×1.9 mm×0.6 mm model HV14 thin film thermoelectric module from Laird Technologies, 3481 Rider Trail South Earth City, Mo. Somewhat larger models might be used with paddle leads. Examples are the 1.8 mm×3.4 mm×3.4 mm model OT08 thermoelectric module from Laird Technologies and the 5 mm×5 mm×1 mm device that is described by GROSS et al. [A. GROSS, G. Hwang, B. Huang, H. Yang, N. Ghafouri, H. Kim, C. Uher, M. Kaviany, K. Najafi. High-performance micro scale thermoelectric cooler: an optimized 6-stage cooler. Proceedings of Transducers 2009, Denver, Colo., USA, Jun. 21-25, 2009, pp. 2413-2416].

The heat at the hot side of the device is conducted away to a thermally conducting layer (e.g., of copper) that lies immediately adjacent to and under the outer thermal insulator on the side of the lead device nearest the thecal sac. The heat in that layer is then conducted via a flexible wire or rod, generally comprising a material that is a good conductor of heat but a poor conductor of electricity, to the case of the pulse generator where the heat will be dispersed and dissipated to surrounding tissue having a relatively large surface area. The wire or rod is thermally insulated on its surface to protect any tissue that it may touch. Under exceptional circumstances when the devices are producing an unusually large amount of heat, an ice pack may be placed on the surface of the skin over an implanted pulse generator. In any case, temperature in the vicinity of the tissue that is cooled or heated will be monitored as described previously so as to prevent unintended damage from overheating or overcooling.

As described previously in connection with thermal ablation using electrodes, the back of the lead device is coated with thermally insulating material in order to thermally protect sensitive tissue at all times. In that regard, it is noted that the thermoelectric device may itself be used as a heat generator, when mounted on the lead device with its hot side towards the posterior longitudinal ligament. For either cooling or heating, surface areas (layers) of thermally conducting material may be mounted or coated onto the side of the electrically insulating material that is applied to the posterior longitudinal ligament, and the thermoelectric device may be applied to that surface area, instead of to the tissue itself. In that case, the surface areas may be used to cool the nerve-containing tissue directly, and the thermoelectric device cools the surface areas. The thermally conducting surface area layer is preferably made of a good thermal conductor that is also a poor electrical conductor, such as diamond powder, beryllium oxide, hexagonal boron nitride or a polyborazine compound. For cooling of the tissue, the cold side of the thermoelectric device(s) is connected to the surface area, and for heating of the tissue, the hot side of the thermoelectric device(s) is connected to the surface area. If two or more thermoelectric devices are connected to the thermally conducting surface area, one or more for cooling and one or more for heating, the user has the option of either cooling or heating the tissue that lies adjacent to the surface area(s) of thermally conducting material, depending on which thermoelectric devices are activated. Because the lead device will also contain thermometers that measure the temperature of the tissue, a servo circuit may control the thermoelectric devices so as to produce a desired temperature, irrespective of the physiological mechanisms that would otherwise counteract temperature fluctuations (e.g., variable blood flow and metabolism). The thermoelectric device itself may be used as the temperature measuring device using the Seebeck effect. In that case, a voltage is measured that corresponds to the temperature difference between the side near the posterior longitudinal ligament and the opposite side of the thermoelectric device, which is thermally connected to the case of the pulse generator, acting as a body-temperature thermal reservoir. A miniature thermistor, or other thermometer device known in the art, may also be placed adjacent to the cold or hot side of the thermoelectric device for purposes of temperature measurement, or for verification of the temperature measured by use of the thermoelectric device [e.g., PSB-S7 thermistor, Shibaura Electronics USA. 39555 Orchard Hill Place, Suite 600, Novi, Mich. 48375].

It is also contemplated that modulation of the temperature of the nerves may be performed in conjunction with the stimulation of those nerves electrically, with mechanical vibration, and/or with light. ACKERMANN et al have suggested that it is beneficial to combine cooling and electrical stimulation, but the combination of cooling with the other stimulation modalities apparently has not been disclosed previously [ACKERMANN D M, Foldes E L, Bhadra N, Kilgore K L. Nerve conduction block using combined thermoelectric cooling and high frequency electrical stimulation. J Neurosci Methods 193 (1, 2010):72-76].

In order to characterize the pathophysiology of the patient's lumbar pain and use that characterization to select energy modalities and parameters of therapeutic stimulation, in one embodiment of the invention the electrodes of the implanted lead device are first used as recording or measurement electrodes, rather than as stimulation electrodes. Thus, when the implanted electrodes are in contact with the posterior longitudinal ligament and/or annulus fibrosus, voltages are measured from each implanted electrode. The voltages are referenced relative to the voltage at any suitable location. For example, the metal casing of the pulse generator may be used as the ground reference point, or any of the electrodes may be selected to be a voltage reference.

If the electrodes are constructed as closely spaced concentric rings (or squares, etc.) of conducting material around a conducting central disc, separated by a narrow bands of electrical insulation, the surface area of the electrode may be selected by electrically connecting one or more of the concentric rings to the central disc via their separate connecting wires, thereby forming a compound electrode. One may also treat an outer ring of the electrode assembly as a ground and measure electrical potentials of the inner electrode components relative to the outer electrode ring. Thus, the surface area of the electrode at any particular location on the lead device need not be predetermined, and the surface area of an electrode even need not be the same when used for electrical stimulation, rather than for recording or measurement.

The voltages measured at each of the (generally compound) electrodes at different locations on the lead device are expected to fluctuate spontaneously. Some of that fluctuation may reflect electronic noise, but much of the fluctuation may be attributed to physiological voltage fluctuations at the site underlying the electrode in the posterior longitudinal ligament and/or annulus fibrosus. The voltage fluctuations may be regarded as local field potentials, the mechanistic origins of which may be analyzed in terms of current source densities [BEDARD C, Kröger H, Destexhe A. Modeling extracellular field potentials and the frequency-filtering properties of extracellular space. Biophys J 86 (3, 2004):1829-1842].

If the measured voltages are filtered to remove frequencies lower than 500 Hz, spike trains might be visible at those higher frequencies, originating from an unknown number of spiking neurons in the immediate vicinity of the electrode. Characterization and analysis of such a spike train, if observed, may be performed by interpreting it as a point process [BROWN E N, Kass R E, Mitra P. Multiple neural spike train data analysis: state-of-the-art and future challenges. Nat Neurosci 7 (5, 2004):456-461].

When the Fourier spectrum of the measured voltages at each of the electrodes is calculated, peaks may be observed in the spectrum. Such peaks may be attributed to voltage oscillations, and the peak narrowness characterizes the regularity of the oscillation. Some of the observed neural activity fluctuations may be due to intrinsic spontaneous activity of the nerves, but other activity may be attributed to the function of the nerves in a larger neural network. Because nerves of the tissue under the electrodes may be comprised in part of sympathetic nerves of the autonomic nervous system, some peaks so measured may reflect oscillations in the activity of the sympathetic nervous system as a whole, involving arterial baro-receptors, respiration, brainstem oscillators involved in thermoregulation and peripheral blood flow, and the like. Other oscillations may be related to central pattern generators of the spinal cord involving repetitive movements, such as locomotion or sexual activity, that may persist to some extent even in the absence of such activity, somewhat analogous to the persistence of oscillations in resting state networks in the brain [Simon M DANNER, Frank Rattay, Ursula S Hofstoetter, Milan R Dimitrijevic, Karen Minassian. Locomotor rhythm and pattern generating networks of the human lumbar spinal cord: an electrophysiological and computer modeling study. BMC Neuroscience 14 (Suppl 1, 2013):P274, pp 1-2]. Other fluctuations in the voltages may be attributed to fluctuating movement of the lumbar spine and its effect on mechano-receptors, to whether the patient is awake or asleep, to whether the patient's bladder is filling, etc.

Power in the spectrum of fluctuations may be filtered into frequency bands, analogous to the frequency bands of an EEG (delta <4 Hz, theta 4-8 Hz, alpha 8-13 Hz, beta 13-21 Hz, sensorimotor 12-15 Hz, high beta 20-32 Hz, and gamma 32+ Hz), but selection of the endpoints of the bands in the present application would be based primarily on their usefulness in analyzing their contribution to the patient's pain (see below). Over a wide range of frequencies, the fluctuations are expect to have 1/f scaling with a slope that varies from patient to patient when plotted against the logarithm of frequency, and that slope may be used to characterize the electrophysiology of the nerves in the posterior longitudinal ligament and underlying annulus fibrosus [LIU X, Eschenfelder S, Blenk K H, Jänig W, Flabler H. Spontaneous activity of axotomized afferent neurons after L5 spinal nerve injury in rats. Pain 84 (2-3, 2000):309-318; SEKINE, M; Yamashita, T; Sakamoto, N; Takebayashi, T; Ishii, S. Mechanosensitive afferent units in the lumbar posterior longitudinal ligament. Poster Session. 47th Annual Meeting, Orthopaedic Research Society, Feb. 25-28, 2001, San Francisco, Calif.; SEKINE M, Yamashita T, Takebayashi T, Sakamoto N, Minaki Y, Ishii S. Mechanosensitive afferent units in the lumbar posterior longitudinal ligament. Spine (Phila Pa. 1976) 26 (14, 2001):1516-1521; MIKI K, Oda M, Kamijyo N, Kawahara K, Yoshimoto M. Lumbar sympathetic nerve activity and hindquarter blood flow during REM sleep in rats. J Physiol 557 (Pt 1, 2004):261-271].

It is understood that the voltage time-series at the several electrodes will generally not be independent of one another, so that Fourier analysis in two (or more) dimensions should be undertaken in order to characterize the covariance of the different electrodes' voltages. It is also understood that wavelet and other types of transforms of the data or other types of analysis may be performed in addition to, or instead of, the Fourier analysis [RODRIGUEZ E E, Hernández-Lemus E, Itzá-Ortiz B A, Jiménez I, Rudomín P. Multichannel detrended fluctuation analysis reveals synchronized patterns of spontaneous spinal activity in anesthetized cats. PLoS One 6 (10, 2011):e26449, pp. 1-11; D. Puthankattil SUBHA, Paul K. Joseph, Rajendra Acharya U, and Choo Min Lim. EEG signal analysis: A survey. J Med Syst 34 (2010):195-212). It is also understood that measurement of voltages with one or more electrodes may be useful for the placement of the lead device. For example, if voltages are initially measured with the lead at more than one position, one may then devise and configure the ultimate location of the stimulation energy that would optimally reduce the patient's pain. In particular, one may devise and configure the ultimate location of the stimulation so as to correspond to electrode sites that exhibit significant spontaneous voltage fluctuations originating in oscillations in the sympathetic nervous system, as confirmed, e.g., by heart rate variability analysis. The recording of local field potentials has heretofore been used as a guide to the selection of which electrodes among an array are to be used for stimulation, but only in connection with deep brain stimulation in which minute changes in electrode position may correspond to very large differences in neural function [U.S. Pat. No. 8,670,830, entitled Stimulation electrode selection, to CARLSON et al.; U.S. Pat. No. 8,078,281, Apparatus for treating neurological disorders by means of chronic adaptive brain stimulation as a function of local biopotentials, to PRIORI et al]. In contrast, the present invention is concerned with measurement of nerve activity in peripheral nerves that are related to the generation of pain, for which the very existence of local field potentials appears to be a novel disclosure.

The measurement of voltage time-series as described above characterizes the electrophysiology of nerves in the posterior longitudinal ligament and underlying annulus fibrosus only at sites directly under the electrodes. The invention contemplates an additional form of measurement using the electrodes that may also be used to characterize the electrophysiology of the tissue between the electrodes. That additional form of measurement makes use of electrical impedance tomography (EIT), which produces a map of electrical conductivity in the region bounded by the measurement electrodes. In addition to the electrodes of the lead, surface EIT electrodes may also be placed on the patient's skin anterior to the disc. Small alternating currents are applied sequentially to electrodes, and the resulting equi-potentials are recorded from the other electrodes. This process is repeated for different electrode configurations, and finally an essentially two-dimensional surface tomogram is constructed using an algorithm that solves the corresponding inverse problem [BROWN B H. Electrical impedance tomography (EIT): a review. J Med Eng Technol 27 (3, 2003):97-108; DAVALOS RV, Otten D M, Mir L M, Rubinsky B. Electrical impedance tomography for imaging tissue electroporation. IEEE Trans Biomed Eng 51 (5, 2004):761-767; LINDERHOLM P, Marescot L, Loke M H, Renaud P. Cell culture imaging using microimpedance tomography. IEEE Trans Biomed Eng 55 (1, 2008):138-146; BOYLE, A., Adler, A. Lionheart, W. R. B. Shape deformation in two-dimensional electrical impedance tomography. IEEE Transactions on Medical Imaging 31 (12, 2012): 2185-2193].

Because the relaxed lumbar spine is curved, the patient should preferably bend forward (flex) by different angles while performing the EIT, in order that the posterior longitudinal ligament and/or underlying annulus fibrosus lie within the region bounded by the device's electrodes (i.e., flex beyond lumbar lordosis into kyphosis) [CONSMULLER T, Rohlmann A, Weinland D, Druschel C, Duda G N, Taylor W R. Comparative evaluation of a novel measurement tool to assess lumbar spine posture and range of motion. Eur Spine J 21 (11, 2012):2170-2180; CONSMULLER T, Rohlmann A, Weinland D, Druschel C, Duda G N, Taylor W R. Velocity of lordosis angle during spinal flexion and extension. PLoS One 7 (11, 2012):e50135, pp. 1-7]. Variation of the lumbar flexure angle (preferably with limited hip flexure) in small steps allows for essentially two-dimensional image surfaces at each angle to be built into a three-dimensional EIT image that compensates for the angle-dependent lumbar strains and conductivity changes. Thus, use of EIT may produce a tomographic image of the tissue volume nearest the electrodes, containing the ligament and annulus. In general, the annulus should be distinguishable from the ligament in such an EIT image because the annulus is reported to have an electrical conductivity that is more than twice that reported for ligaments [JUSTIZ, A M, Cheung, H and Gu, W Y. Electrical conductivity of annulus fibrosus. Poster Session—47th Annual Meeting, Orthopaedic Research Society, Feb. 25-28, 2001, San Francisco, Calif.; GU WY, Justiz M A, Yao H. Electrical conductivity of lumbar anulus fibrosis: effects of porosity and fixed charge density. Spine 27 (21, 2002):2390-2395; Anonymous. Tendon/Ligament. Electrical Conductivity Tissue Frequency Chart. Tissue Properties Database. IT'IS Foundation. ETH Zentrum, ETZ. CH-8092 Zurich. Switzerland]. Tears within the annulus should also be distinguishable from the remainder of the annulus, because the tears contain zones of vascularized granulation material that would have a different conductivity than the remainder of the annulus [PENG B, Wu W, Hou S, Li P, Zhang C, Yang Y. The pathogenesis of discogenic low back pain. J Bone Joint Surg Br 87 (1, 2005): 62-67]. Consequently, the 3-dimensional EIT image will contain much of the information that is currently provided by discography and can either complement the discography or substitute for it. Once the lead is implanted within the anterior epidural space, such EIT imaging may be performed repeatedly, in order to track changes in the PLL and annulus fibrosus over time. Sequential EIT imaging would also be useful when electroporation is being used to damage nerves, as described above, because the EIT imaging would document accompanying changes in conductivity in tissue in the vicinity of the nerves that were being electroporated [DAVALOS RV, Otten D M, Mir L M, Rubinsky B. Electrical impedance tomography for imaging tissue electroporation. IEEETrans Biomed Eng 51 (5, 2004): 761-767; GRANOT Y, Rubinsky B. Methods of optimization of electrical impedance tomography for imaging tissue electroporation. Physiol Meas 28 (10, 2007):1135-1147; LINDERHOLM P, Marescot L, Loke M H, Renaud P. Cell culture imaging using microimpedance tomography. IEEE Trans Biomed Eng 55 (1, 2008):138-146].

The EIT is preferably performed by applying very low alternating current of different frequencies to the different electrodes, in order that the conductivity imaging be performed in real time [Yair GRANOT and Boris Rubinsky. Methods of optimization of electrical impedance tomography for imaging tissue electroporation. Physiol. Meas. 28 (2007):1135-1147]. Over short time periods (e.g., about 1 second), the conductivity tomographic images may be averaged so as to reduce noise. But over longer time periods, the images may be observed to fluctuate due, for example, to fluctuations in the fluid and electrolyte content of the imaged region. Accordingly, the same type of fluctuation analysis that was described above for the time-varying voltages at the individual electrodes may be performed for small regions throughout the imaged region. It is understood that the above-mentioned voltage time-series measured at the several electrodes will generally not be independent of the EIT data, so that Fourier analysis in two (or more) dimensions should be undertaken in order to characterize the covariance of the two types of data [JACKSON AR, Travascio F, Gu W Y. Effect of mechanical loading on electrical conductivity in human intervertebral disk. J Biomech Eng 131 (5, 2009): 054505: pp. 1-15; TRAVISCIO F, Jackson A R, Brown M D, Gu W Y. Relationship between solute transport properties and tissue morphology in human annulus fibrosus. J Orthop Res 27 (12, 2009):1625-1630].

Furthermore, because the EIT image characterizes the conductivity of the tissue, it may be used in other ways to select the parameters of nerve stimulation. In particular, the EIT data may be used to devise and configure the voltages on the electrodes in such a way as to preferentially stimulate selected parts of the posterior longitudinal ligament and/or the underlying annulus fibrosus. In order to motivate a method for preferentially stimulating a particular volume of the posterior longitudinal ligament and/or annulus fibrosus by reversible electrical stimulation, it is useful to first summarize the relevant physics of electric fields and currents that are produced by the electrodes. Ampere's law with Maxwell's correction may be written as: $\nabla \cdot J + \nabla \cdot \in (\partial E/\partial t) = 0$, where J is the electrical current density, E is the electric field, $\in$ is the permittivity, and t is time. Under the assumption that changes in the magnetic field may be ignored, E may be written as the gradient of a scalar potential $\Phi$: $E = -\nabla \Phi$. The electrical current density J is determined by the electric field and conductivity as follows, where the conductivity $\sigma$ is a function of position: $J = \sigma E = -\sigma \nabla \Phi$. If the current flows in material that is essentially unpolarizable (i.e., is presumed not to be a dielectric so that $\in = 0$) or if a time-independent (steady state) solution is desired, substitution of the expression for J into the above expression for Ampere's law gives $-\nabla \cdot (\sigma \nabla \Phi) = 0$, which is a form of Laplace's equation [Richard P. FEYNMAN, Robert B. Leighton, and Matthew Sands. The Feynman Lectures on Physics. Volume II. Addison-Wesley Publ. Co. (Reading Mass., 1964), page 15-15]. Thus, given the positions and sizes of the electrodes that are part of the lead device, given the conductivity as a function of position within the tissue that was measured using EIT, and given the voltages that are applied to the electrodes, then the three-dimensional distribution of the electrical potential and electric field within the posterior longitudinal ligament or annulus fibrosus may be estimated by solving the corresponding Laplace's equation. The more general equations may also be evaluated in order to take into account time-dependent effects, particularly the effect of pulse width on distance from the electrodes [SZLAVIK R B, de Bruin H. The effect of stimulus current pulse width on nerve fiber size recruitment patterns. Med Eng Phys 21 (6-7, 1999):507-515].

In the present invention, this model of the electric field within the posterior longitudinal ligament and annulus fibrosus is exercised by varying possible voltages supplied to the electrodes of the lead, in order to find the combination of electrode voltage amplitudes that maximize stimulation of the tissue in the region of interest (e.g., maximize the electric field amplitude) and minimize stimulation in other regions. Laplace's equation has been solved numerically in order to compare different electrode shapes and numbers for transcranial stimulation, but its use in connection with an implanted lead is apparently new. Furthermore, its use is new here because it makes use of the conductivities that had been measured by EIT [Abhishek DATTA, Maged Elwassif, Fortunato Battaglia and Marom Bikson. Transcranial current stimulation focality using disc and ring electrode configurations: FEM analysis. J. Neural Eng. 5 (2008): 163-174].

When the electrodes of the lead are being used for recording and measurement, as described above, the invention contemplates the simultaneous measurement of the patient's pain, so as to correlate the voltage fluctuations with the pain. The pain measurement may be based on self-reporting of the patient, typically in a numeric range of 0-10 with 0 as no pain, 1-3 as mild pain, 4-6 as moderate pain, and 7-10 as severe pain. Alternatively, there may be an objective measurement of pain involving psychometric evaluation of the patient, by an observer viewing such behaviors as facial grimacing, groaning, or writhing [LI D, Puntillo K, Miaskowski C. A review of objective pain measures for use with critical care adult patients unable to self-report. J Pain 9 (2008): 2-10; LABUS J S, Keefe F J, Jensen M P. Self-reports of pain intensity and direct observations of pain behavior: when are they correlated? Pain 102 (1-2, 2003): 109-124]. Physiological measurements may also be used to estimate the level of pain without the need for an observer, including the measurement of features within an EEG and measurement of one or more autonomic physiological variables (heart rate variability, electrodermal activity, as described below) [TOUSIGNANT-Laflamme Y, Rainville P, Marchand S. Establishing a link between heart rate and pain in healthy subjects: a gender effect. J Pain 6 (2005): 341-347; HAMUNEN K, Kontinen V, Hakala E, Talke P, Paloheimo M, Kalso E. Effect of pain on autonomic nervous system indices derived from photoplethysmography in healthy volunteers. Br J Anaesth 108 (5, 2012):838-844; NIR RR, Sinai A, Raz E, Sprecher E, Yarnitsky D. Pain assessment by continuous EEG: association between subjective perception of tonic pain and peak frequency of alpha oscillations during stimulation and at rest. Brain Res 1344 (2010): 77-86]. In preferred embodiments, the EEG sensors may comprise ambulatory sensors [CASSON A, Yates D, Smith S, Duncan J, Rodriguez-Villegas E. Wearable electroencephalography. What is it, why is it needed, and what does it entail? IEEE Eng Med Biol Mag. 29 (3, 2010):44-56; NIKULIN VV, Kegeles J, Curio G. Miniaturized electroencephalographic scalp electrode for optimal wearing comfort. Clin Neurophysiol 121 (7, 2010):1007-1014]. Signal processing methods, comprising not only the application of conventional linear filters to the raw EEG data, but also the nearly real-time extraction of non-linear signal features from the data, may be considered to be a part of the EEG monitoring [D. Puthankattil SUBHA, Paul K. Joseph, Rajendra Acharya U, and Choo Min Lim. EEG signal analysis: A survey. J Med Syst 34 (2010):195-212].

It is understood that for certain scalp electrode recordings, such as the recording of a P300 event-related potential, the measurement may indicate the patient's conscious recognition of a painful event, rather than subconscious neural processing of the painful stimuli [ZASLANSKY R, Sprecher E, Katz Y, Rozenberg B, Hemli J A, Yarnitsky D. Pain-evoked potentials: what do they really measure? Electroencephalogr Clin Neurophysiol 100 (5, 1996):384-391; GROSS J, Schnitzler A, Timmermann L, Ploner M. Gamma oscillations in human primary somatosensory cortex reflect pain perception. PLoS Biol 5 (5, 2007):e133:1168-1173]. However, it is also possible to assess the degree of pain even in unconscious individuals, by using fMRI to image particular regions of the patient's brain that receive signals about painful stimuli [Tor D. WAGER, Lauren Y. Atlas, Martin A. Lindquist, Mathieu Roy, Choong-Wan Woo and Ethan Kross. An fMRI-Based Neurologic Signature of Physical Pain. N Engl J Med 368 (2013):1388-1397; Dieter VAITL. Interoception. Biological Psychology 42 (1996):1-27; CRITCHLEY HD, Wiens S, Rotshtein P, Ohman A, Dolan R J. Neural systems supporting interoceptive awareness. Nat Neurosci 7 (2, 2004):189-195; CRAIG, A. D. How do you feel? Introception: the sense of the physiological condition of the body. Nat. Rev. Neurosci 3 (2002):655-666; CRAIG A D. How do you feel—now? The anterior insula and human awareness. Nat Rev Neurosci 10 (1, 2009):59-70].

Several non-invasive measurements can be used to assess sympathetic activity in a patient, and they may provide an indication of parasympathetic activity as well [MENDES, W. B. Assessing the autonomic nervous system. Chapter 7 In: E. Harmon-Jones and J. Beer (Eds.) Methods in Social Neuroscience. New York: Guilford Press, 2009, pp. 118-147]. One such method involves extracting variability of the heart rate from a measurement of the patient's electrocardiogram (ECG). The ECG sensors may be embedded in garments or placed in sports wristwatches, as currently used in programs that monitor the physiological status of soldiers [G. A. SHAW, A. M. Siegel, G. Zogbi, and T. P. Opar. Warfighter physiological and environmental monitoring: a study for the U.S. Army Research Institute in Environmental Medicine and the Soldier Systems Center. MIT Lincoln Laboratory, Lexington Mass. 1 Nov. 2004, pp. 1-141]. Those ECG sensors should be adapted to the automatic extraction and analysis of particular features of the ECG, including indices of P-wave morphology, as well as heart rate variability indices of parasympathetic and sympathetic tone. Heart rate variability is conventionally assessed by examining the Fourier spectrum of successive heart rate intervals that are extracted from an electrocardiogram (RR-intervals). However, more elaborate indices of sympathetic and parasympathetic activity may also be extracted from the variation in successive heart rate intervals. Additional noninvasive measures of sympathetic activity, such as variability of QT intervals, are preferably measured as well. A signal representing respiration may also be derived from the ECG, or respiration may be independently measured noninvasively using methods known in the art, such as using a nose thermistor, inductive plethysmography, mercury in silastic strain gauges, impedance pneumography, and noninvasive respiratory volume monitoring [U. Rajendra ACHARYA, K. Paul Joseph, N. Kannathal, Choo Min Lim and Jasjit S. Suri. Heart rate variability: a review. Medical and Biological Engineering and Computing 44 (12, 2006), 1031-1051; BOETTGER S, Puta C, Yeragani V K, Donath L, Müller H J, Gabriel H, Bär K J. Heart rate variability, QT variability, and electrodermal activity during exercise. Med Sci Sports Exerc 42 (3, 2010):443-448; Sung-Bin PARK, Yeon-Sik Noh, Sung-Jun Park, Hyoung-Ro Yoon. An improved algorithm for respiration signal extraction from electrocardiogram measured by conductive textile electrodes using instantaneous frequency estimation. Med Bio Eng Comput 46 (2008):147-158].

Electrodermal measurements, also known as galvanic skin responses, have been used traditionally in psychophysiology to indicate the patient's emotional and/or cognitive state and sympathetic tone. Ordinarily, such measurement is made on the palm, volar side of a finger, or feet of a patient, although electrodermal measurement at other sites such as the shoulder may be useful as well. In the present application the preferred site is below the lumbar spine, such as the soles of the feet [Marieke van DOOREN, J. J. G. (Gert-Jan) de Vries, Joris H. Janssen. Emotional sweating across the body: Comparing 16 different skin conductance measurement locations. Physiology & Behavior 106 (2012): 298-304]. Since 1981, a particular skin conductance method has been the international standard technique to record and analyze electrodermal activity (EDA) [Wolfram BOUCSEIN. Electrodermal activity, 2nd Ed., New York: Springer, 2012, pp. 1-618]. Both short-term electrodermal responses to stimuli and longer term spontaneous electrodermal activity levels are measured. Recently, miniature electrodermal sensors have become available for use in ambulatory monitoring [Ming-Zher P O H, Nicholas C. Swenson, and Rosalind W. Picard. A wearable sensor for unobtrusive, long-term assessment of electrodermal activity. IEEE Transactions on Biomedical Engieering 57 (5, 2010):1243-1252; Ming-Zher P O H, Tobias Loddenkemper, Nicholas C. Swenson, Shubhi Goyal, Joseph R. Madsen and Rosalind W. Picard. Continuous monitoring of electrodermal activity during epileptic seizures using a wearable sensor. 32nd Annual International Conference of the IEEE EMBS, Buenos Aires, Argentina, Aug. 31-Sep. 4, 2010, pp. 4415-4418; Ming-Zher P O H, Tobias Loddenkemper, Claus Reinsberger, Nicholas C. Swenson, Shubhi Goyal, Mangwe C. Sabtala, Joseph R. Madsen, and Rosalind W. Picard. Convulsive seizure detection using a wrist-worn electrodermal activity and accelerometry biosensor. Epilepsia 53 (5, 2012):e93-e97].

In normal individuals, norepinephrine released from sympathetic nerves onto alpha receptors in blood vessels causes vasoconstriction. Thus, an increase or decrease in sympathetic tone would normally result in a decrease or increase in blood flow to the lumbar region, respectively. Consequently, the measurement of changes in blood flow may be used to infer changes in the sympathetic activity that caused the blood flow changes, whether the changes occur spontaneously or in response to stimulation. The situation is more complex in tissue that is experiencing inflammation. Initially, the vasoconstrictive capacity of sympathetic nerve fibers is counteracted by a hyperemic response that promotes vasodilation due to the release of vasoactive mediators (histamine, bradykinin, neuropeptides, prostaglandins) that are produced by mast cells, macrophages, fibroblasts, parenchymal cells, the vessel wall, and possibly the sympathetic nerves themselves. But eventually, it is expected that the long-term steady-state response to inflammation would be a reduction in tissue blood flow, rather than that temporary hyperemia. One general explanation for this variable blood flow is that the receptor composition of the lumbar blood vessels and nerves changes throughout the inflammatory process [GRANGER D N, Senchenkova E. Inflammation and the Microcirculation. Chapter 4. pp. 15-18 in: San Rafael (CA): Morgan & Claypool Life Sciences, 2010; ESPAHBODI S, Doré C J, Humphries K N, Hughes S P. Color Doppler ultrasonography of lumbar artery blood flow in patients with low back pain. Spine (Phila Pa. 1976) 38 (4, 2013):E230-E236].

Therefore, the present invention also discloses methods to evaluate the relation or correlation between regional sympathetic tone and the local flow of blood within the lumbar region. The measurement of fluctuations in regional sympathetic tone was described above, e.g., the measurement of fluctuations in the patient's electrodermal activity on one or both feet. The measurement of local blood flow in the present invention makes additional use of the optical fibers and lasers that were described above in connection with the stimulation of the nerves with light. In addition to that usage, laser Doppler flowmetry can be performed using those same optical fibers and laser diodes, resulting in a measurement of the flow of blood in the tissue that is illuminated with the laser. The laser Doppler flowmetry may be performed with each of many single optical fibers that are directed to different areas of the posterior longitudinal ligament and/or annulus fibrosus (see FIG. 8) [U.S. Pat. No. 4,590,948, entitled Method and apparatus for measuring the blood flow in the superficial blood vessels of tissue, to NILSSON; CAI H, Pettersson H, Rohman H, Larsson S E, Oberg P A. A new single-fibre laser Doppler flowmeter based on digital signal processing. Med Eng Phys 18 (7, 1996):523-528; H. CAI, H. Rohman, S. E. Larsson, P. Å. Öberg. Laser Doppler flowmetry: characteristics of a modified single-fibre technique. Medical and Biological Engineering and Computing 34 (1, 1996):2-8; Shimpei KOHRI, Tsutomu Tajikawa, Kenkichi Ohba. Development of a miniaturized fiber-optic LDV sensor for local blood velocity measurement. Biomedical Engineering Research 2 (3, 2013):131-138]. Alternatively, miniature Doppler flowmeters may be mounted into the lead device itself, without using optical fibers [Yoshinori KIMURA, Masaki Gonna, Atsushi Onoe, Eiji Higurashi, and Renshi Sawada. Integrated laser Doppler blood flowmeter designed to enable wafer-level packaging. IEEE Transactions on Biomedical Engineering 57 (8, 2010): 2026-2033].

Thus, in preferred embodiments, measurement of the patient's pain will be by self-reporting (e.g., pushing one of several event-marker buttons to record the pain level, used in conjunction with laser Doppler measurement of blood flow and non-invasive measurement of the patient's EEG and autonomic tone (heart rate variability, electrodermal activity). For situations in which self-reporting is not practical (e.g., when the patient has dementia, when the patient is in some state of anesthesis or during veterinary procedures), the EEG and autonomic tone measurements may be supplemented with psychometric evaluation of pain and/or the evaluation of pain levels using fMRI.

The activity of nerves within the posterior longitudinal ligament and in the underlying annulus fibrosus is expected to depend in part on the mechanical stresses and strains in those anatomical locations, particularly because afferent nerve fibers in those locations are mainly mechanosensitive nociceptive fibers, classified into Group III and Group IV types, with a high mechanical threshold for activation [SEKINE M, Yamashita T, Takebayashi T, Sakamoto N, Minaki Y, Ishii S. Mechanosensitive afferent units in the lumbar posterior longitudinal ligament. Spine 26 (14, 2001): 1516-1521]. The stresses and strains at those locations in turn depend on the movements and postures in the lumbar region of the spine, which may be made provocatively and under different loads (e.g., lifting a weight) as flexions (bending forward) and extensions (bending backwards); lateral bending (left, right); and axial rotation (clockwise, counterclockwise). If the patient is ambulatory, he or she will undergo combinations of these movements throughout the day, which may be associated with activities such as sitting or standing with different postures, the lifting of objects, and physical activity in general [ADAMS M A. Biomechanics of back pain. Acupunct Med 22 (4, 2004): 178-188; ADAMS M A, Dolan P. Spine biomechanics. J Biomech 38 (10, 2005):1972-1983; Robert J. KOWALSKI, Lisa A. Ferrara, and Edward C. Benzel. Biomechanics of the Spine. Neurosurg Q 15 (1, 2005): 42-59]. Thus, the invention also contemplates long-term (e.g., 24 hour) ambulatory measurement of the spontaneous electrical fluctuations that may be measured from the electrodes, along with the simultaneous measurement of the patient's pain and the measurement of variables that may be used to predict those data (e.g., stresses and strains in the lumbar region of the spine).

Alteration in the stresses and strains in the anterior annulus fibrosus and posterior longitudinal ligament may also be made provocatively during the course of the performance of discography. In fact, discography and implantation of the devices disclosed here may be combined into a single procedure, during which time stresses and strains are measured [LEE S H, Derby R, Chen Y, Seo K S, Kim M I In vitro measurement of pressure in intervertebral discs and annulus fibrosus with and without annular tears during discography. Spine J 4 (6, 2004):614-618; SEO KS, Derby R, Date E S, Lee S H, Kim B J, Lee C H. In vitro measurement of pressure differences using manometry at various injection speeds during discography. Spine J. 7 (1, 2007):68-73].

The movements of the lumbar spine may be measured continuously by embedding preferably two or more miniature accelerometers and/or gyroscopes into the implanted lead device, e.g., at its ends. For example, the accelerometers may be the 2 mm×2 mm×0.98 mm Bosch Model BMA220 (Bosch Sensortec, 1800 W. Central Road Mount Prospect, Ill. 60056). Integration of the acceleration data provides velocity and position data, so those data characterize much of the patient's activity, and they may be used to infer deformations of the disc and ligaments [PEARCY M J, Tibrewal S B. Lumbar intervertebral disc and ligament deformations measured in vivo. Clin Orthop Relat Res (191, 1984):281-286].

The stresses within the implanted device and at the interface between the device and the posterior longitudinal ligament and/or annulus may be measured with miniature stress sensors embedded into the lead device, with the stress sensors placed in the vicinity of the one or more selected tissue locations [ADAMS M A, McNally D S, Dolan P. "Stress" distributions inside intervertebral discs. J Bone J Surg 78 (1996):965-972]. Although the stress sensor could be like the one described by GLOS et al. for measuring compression within the annulus, a preferred stress sensor is of the type described by ALFARO, not only because of its 3 mm×3 mm×0.3 mm size, but also because it can measure shear stress at the device/tissue boundary in addition to normal stresses [GLOS DL, Sauser F E, Papautsky I, Bylski-Austrow D I. Implantable MEMS compressive stress sensors: Design, fabrication and calibration with application to the disc annulus. J Biomech 43 (11, 2010):2244-2248; Fernando ALFARO, Lee Weiss, Phil Campbell, Mark Miller and Gary K Fedder. Design of a multi-axis implantable MEMS sensor for intraosseous bone stress monitoring J. Micromech. Microeng. 19 (2009):085016, pp. 1-13].

It is possible in principle to model and analyze the measured stresses and strains using finite element analysis, as a function of body movements in the vicinity of the posterior longitudinal ligament and posterior annulus fibrosus [LI H, Wang Z. Intervertebral disc biomechanical analysis using the finite element modeling based on medical images. Comput Med Imaging Graph 30 (6-7, 2006):363-370; DOLAN P, Adams M A. Recent advances in lumbar spinal mechanics and their significance for modelling. Clin Biomech (Bristol, Avon) 16 (Suppl 1, 2001):58-516]. However, this is difficult in practice because vertebral components are viscoelastic, such that stresses are functions not only of current anatomical positions, but also of velocities and histories [ADAMS M A, Dolan P. Time-dependent changes in the lumbar spine's resistance to bending. Clin Biomech 11 (4, 1996):194-200]. They may even depend on the time of day. Compounding the difficulty of modeling lumbar stresses and strains is the contribution of back muscles that contract and relax reflexively in response to shifting loads [Z. LADIN and K. M. Neff. Testing of a Biomechanical Model of the Lumbar Muscle Force Distribution Using Quasi-Static Loading Exercises. J Biomech Eng 114 (4, 1992), 442-449; PANJABI M M. Clinical spinal instability and low back pain. J Electromyogr Kinesiol 13 (4, 2003):371-379; PANJABI M M. A hypothesis of chronic back pain: ligament subfailure injuries lead to muscle control dysfunction. Eur Spine J 15 (5, 2006):668-676; ROLAND M O A critical review of the evidence for a pain-spasm-pain cycle in spinal disorders. Clin Biomech (Bristol, Avon) 1 (1986):102-109].

Therefore, when the above-mentioned accelerometer and stress-sensor measurements are being made in order to characterize the time-varying biomechanics of the lumbar spine in the vicinity of the implanted device, a more complete characterization may be made by using simultaneous back-surface electromyography (EMG) to measure activity of the nearby erector spinae muscle group (longissimusm, iliocostalis, and spinalis muscles). Such measurements would be particularly useful when performing simultaneous ambulatory monitoring of the patient's pain, nerve activity, and biomechanics [CASSISI J E, Sexton-Radek K, Castrogiovanni M, Chastain D, Robinson M E. The use of ambulatory EMG monitoring to measure compliance with lumbar strengthening exercise. Biofeedback Self Regul 18 (1, 1993):45-52; DOLAN P, Earley M, Adams M A. Bending and compressive stresses acting on the lumbar spine during lifting activities. J Biomech 27 (10, 1994):1237-1248].

The structure of lead devices containing the above-mentioned components is illustrated in the examples shown in FIG. 8. The lead shown in FIG. 8A is intended to be placed horizontally within the anterior epidural space, across one of the patient's discs and across nerves within intervertebral fibers of the posterior longitudinal ligament. The lead shown in FIG. 8B is intended to be placed vertically (longitudinally) to stimulate nerves in vertebral fibers of the posterior longitudinal ligament, as well as portions of two (or more) of the patient's discs and intervertebral fibers of the PLL. All stimulating electrodes 61 of the lead devices (and devices involving other forms of energy) are unidirectional, such that the electrode contacts are located on one side of the electrically insulating substrate of the lead device 62 that is made of a flexible material. On the side that is to face the posterior longitudinal ligament (the electrode side), the electrically insulating substrate is made with, or coated with, a thermally conducting material that is also an electrical insulator. On the opposite side that would face the thecal sac, the lead device is coated with a thermal insulator such as ceramic foam. The electrode contacts in FIG. 8A are visible in the view 95. When that view is rotated by 90 degrees, as in the view labeled as 96, a cross section of that rotated view would reveal the electrodes 61, wires 63 that connect the electrode to a pulse generator 64, and channels 97 through which those wires run. In view 96, the electrode-side of the electrical insulator substrate 62 is shown to be coated with the material that is a good thermal conductor but that is also a good electrical insulator. On the opposite side of the lead, there is a layer of material that is a good thermal conductor 115, and on the very outside surface of the lead there is a layer of material that is a good thermal insulator 116. The layer 115 is used to conduct heat that is generated within the lead to the case of the pulse generator, and the thermal insulator 116 protects the thecal sac and nerve roots from any heat produced by the lead. When the view 95 is rotated by 180 degrees to produce the view labeled as 98, the electrodes and other surface-mounted components are no longer visible. Thus, only the insulating material may be seen from that back side (underlying electrode locations are indicated with dotted lines, and the locations of other components are shown, but they would not be visible in view 98). Radio-opaque directional indicators 65 are also shown to be located within the leads. The lead device also contains small tabs 99 that are used to anchor the lead to bone or other relatively immobile tissue.

The lead devices shown in FIG. 8 contain additional components that were described above. In the figure, symbols are used to indicate the approximate location and size of the following components: electrode 61, optical fiber 120 carrying light to illuminate the tissue, vibrator 130, thermoelectric cooler 140, which is also used as a thermometer and could also be used as a heater if reversed, accelerometer 150 for monitoring position, and stress sensor 160. The connections going from the lead device to the pulse generator 64 can be situated at the end of the lead device 108 or on the side of the device 109, or both. As shown in FIG. 8B, a bundle of wires 109 connect the lead's components to corresponding circuits within the pulse generator 64. The circuits include those for electrical pulse generation for voltages $V_1, V_2, \ldots V_N$ at electrodes 1, 2, ... N, electrical measurements involving the electrodes when the electrodes are switched from pulse generation to measurement mode, vibration pulse generation, cooling pulses involving the thermoelectric devices, temperature measurement, measurement of position and velocity with the accelerometers, and measurement of mechanical stresses. As also shown in FIG. 8B, a bundle of optical fibers 108 carries light from two laser diodes (e.g., ultraviolet and infrared) to the sites on the lead device where tissue is stimulated optically. The pulses of light are produced by the light pulse generator shown in the figure. The light pulse generator may also be used in a laser Doppler flowmeter mode, ordinarily with an infrared laser, in order to measure blood flow. A wire is also shown in that figure to connect the lead device thermally via thermally conducting material 115 to the case of the pulse generator 64. The thermally conducting case then serves as a heat reservoir when in contact with surrounding tissue. The wire may comprise material that is a good thermal conductor but that is an electrical insulator, such as beryllium oxide, hexagonal boron nitride or a polyborazine compound.

The pulse generator 64 is also shown to contain a power module (e.g., battery) that is used to drive the other circuits within the pulse generator. The pulse generator also contains circuits need to transmit/receive data and control signals to/from external devices. As shown, the communication may be wireless, and the device with which the pulse generator 64 communicates may be a computer that is similarly configured for wireless communication, possibly via a handheld programmer. For example, the operation(s) to be performed are specified by the user in a program in the computer (e.g., selection of energy modalities and their corresponding pulse parameters, or receipt of measurement data from the lead device). Communication between devices preferably makes use of radio communication within unlicensed ISM frequency bands. Components of the wireless system in the pulse generator 64, computer, and hand-held programmer may comprise a system-on-chip transceiver with an integrated microcontroller; a crystal; associated balun & matching circuitry, and an antenna [Dag GRINI. RF Basics, RF for Non-RF Engineers. Texas Instruments, Post Office Box 655303, Dallas, Tex. 75265, 2006]. The computer can also communicate wirelessly with other sensors that are being used to characterize the pathophysiology of the patient, such as data from EEG, ECG, EMG, and electrodermal sensors. The computer may communicate wirelessly with a handheld device that the patient is using as an event maker, pain-level indicator, or portable controller/programmer. Thus, the health care provider or patient may select and initiate a stimulation protocol using the computer or handheld controller, or may initiate a protocol to start the wireless streaming of data measured using the lead's electrodes, accelerometers, stress sensors, thermometers, scalp electrodes, ECG electrodes, EMG electrodes, electrodermal sensors, laser Doppler flowmeters, and the like, to the computer with which the pulse generator 64 is communicating. The integration, analysis and modeling of all such data, and the use of that data for controlling stimulation protocols, are described below. The computer may be connected to other computers on the internet, where some of the selection and initiation of protocols, as well as data acquisition and analysis, may also take place.

Making the patient undergo planned or controlled movements in order to generate activity in the nerves of the posterior longitudinal ligament and underlying annulus fibrosus, as well as possibly produce pain, is a type of evoked potential maneuver. Similar maneuvers include the controlled or diagnostic vibration of nerves within the posterior longitudinal ligament and underlying annulus fibrosus, the controlled or diagnostic lighting of those nerves, and the controlled or diagnostic heating or cooling of those nerves. The immediate consequence of such a diagnostic stimulus maneuver is then measured using the lead's electrodes and other measurement devices of the system.

The invention also contemplates the planned or controlled stimulation of one or more of the lead's electrodes, in order to measure the voltages that are evoked at other electrodes of the lead and other measurement devices of the system (e.g., laser Doppler flowmeter). Any such stimulus will usually be a single pulse or a series of pulses in the form of a stimulus burst, generally of the types that may be combined during a therapeutic stimulus protocol. In the following remainder of the disclosure, it is assumed that the stimulus pulse or burst of pulses correspond to parameter values that would have only reversible effects. For example, if the pulse is electrical, then the amplitude of the pulse would be limited to values less than about 10 volts, and the time between pulses in a burst would correspond to frequencies of less than about 10 kHz. The discussion that follows describes how measurement of the effects of those pulses or bursts of pulses may be used to select reversible stimulation modalities and their corresponding parameters, for purposes of therapy.

The neuronal activity evoked by the above-mentioned maneuvers may also be measured at scalp electrodes, thereby making the planned stimulation via the lead's electrodes a type of classical evoked potential (EP) measurement protocol. For example, the investigator initiates the generation of one or more sensory stimuli via the pulse generator, such as a flash of light, a vibration, a pulse of cooling, or an electrical pulse applied to an electrode of the lead. The potentials measured on the scalp are time-locked relative to the onset of the stimulus. When a transient response EP is measured, the EP waveform ordinarily consists of a series of peaks and valleys relative to the baseline potential, which are characterized by their amplitudes (positive or negative), as well as their times of occurrence relative to the stimulus (their latencies). The potentials that are so-measured are a mixture of the neural activity of structures involved in both the unconscious and conscious processing of the sensory information, as may be inferred by performing the EP measurement when the subject is or is not anesthetized, or awake versus asleep. One may use transient response EP data acquisition equipment that is capable of averaging multiple successive evoked potentials (so as to increase the signal-to-noise of the EP data) and also automatically locate peaks or other features in the evoked potential waveform, such as a P300 peak that corresponds to a conscious evaluation on the part of the patient that the stimulus is interesting.

Peaks and troughs in the transient response EP may often be identified by comparing their properties with those found in normative databases. Artifacts that appear in the EP may also be identified and preferably eliminated. In general, somatosensory stimuli evoke early cortical components (N25, P60, N80), which are generated in the contralateral primary somatosensory cortex (S1) related to the processing of the physical stimulus attributes. About 100 ms after stimulus application, additional cortical regions are activated, such as the secondary somatosensory cortex (S2), and the posterior parietal and frontal cortices, marked by a parietal P100 and bilateral frontal N140. A stimulus that is applied near the midline of the posterior longitudinal ligament may result in an EP that appears on one or the other side of the brain, depending on whether the stimulus is applied a little to the left or to the right of the midline [KNIGHT R T, Scabini D. Anatomic bases of event-related potentials and their relationship to novelty detection in humans. J Clin Neurophysiol 15 (1, 1998):3-13; KECECI H, Degirmenci Y, Atakay S. Habituation and dishabituation of P300. Cogn Behav Neurol 19 (3, 2006):130-134; William R. GOFF. Human average evoked potentials: procedures for stimulating and recording. Chapter 3, pp. 101-156 in: Bioelectric Recording Techniques. Part B. Electroencephalography and Human Brain Potentials (Richard F. Thompson and Michale M. Patterson, eds). New York: Academic Press, 1974; David REGAN. Human Brain Electrophysiology. Evoked potentials and evoked magnetic fields in science and medicine. New York: Elsevier Science Publishing Co., 1989, pp. 1-672; Terence W. PICTON, Otavio G. Lins and Michael Scherg. The recording and analysis of event-related potentials. Chapter 1 (pp. 3-73) in Handbook of Neuropsychology, Vol. 10 (F. Boller and J. Grafman, eds). Amsterdam: Elsevier Science B.V., 1995; Monica FABIANI, Gabriele Gratton and Michael G. H. Coles. Event Related Potentials. Methods, Theory, and Applications. Chapter 3, pp. 53-84 In: John T. Cacioppo, Louis G. Tassinary and Gary G. Berntson (eds). Handbook of Psychophysiology, 2nd Ed. Cambridge: Cambridge University Press, 2000; Steven J. LUCK. An introduction to event-related potentials and their neural origins. Chapter 1 (pp. 1-50) in: Steven J. LUCK. An Introduction to the Event-Related Potential Technique. Cambridge, Mass.: MIT Press, 2005; Todd C. HANDY (ed). Event-related Potentials: A Methods Handbook. Cambridge, Mass.: MIT Press, 2005, pp. 1-380; Steven J LUCK and Emily S Kappenman, eds. Oxford handbook of event-related potential components. Oxford: Oxford University Press, 2012, pp. 1-626].

An important aspect of the invention is its ability to model, explain, or predict the occurrence of pain as a function of spontaneous (e.g., ambulatory) or deliberate stimuli that the patient experiences. Given that data concerning stimuli and physiological sensors are collected as described above, methods are known in the art that may be used to predict the data related to pain from the other data. The data may contain all of the variables described above or a subset of them, but should ordinarily include at least the measurement of pain. Modeling and analysis of the data are generally performed using the computer with which the pulse generator (64 in FIG. 8) is in communication. The modeling and analysis may be performed using any statistical or artificial intelligence or machine learning or optimization methods known in the art, including autoregressive models as well as models that make use of principal components, Kalman filters, wavelet transforms, hidden Markov models, artificial neural networks, and/or support vector machines. In the preferred embodiments of the present invention, support vector machines are used. A support vector machine (SVM) is an algorithmic approach to the problem of classification within the larger context of supervised learning [PRESS, W H, Teukolsky, S A, Vetterling, W T, Flannery, B P. Section 16.5. Support Vector Machines. In: Numerical Recipes: The Art of Scientific Computing (3rd ed.). New York: Cambridge University Press, 2007].

In the present context, a training set of data will have been acquired that includes whether or not the patient is experiencing pain greater than or equal to some specified level, as a function of time. For example, using a self-reported pain scale, the specified level may be a "7", or the equivalent level of pain may have been determined by one or more of the objective methods that were described above. It is understood that the analysis may be repeated using any other numerical level of pain as a cutoff, so that the analysis contemplates that the patient may be experiencing an arbitrary level of pain.

The classification of the patient's state at any instant is whether pain is being experienced at or above the specified level, and the data used to make the classification (prediction) consist of the remaining acquired data as a function of time. Thus, the other data generally include a time-series of measured values for each of the other variables (such as electrode voltages, position or mechanical stresses, and/or laser Doppler flowmeter data, possibly weighted such that older data within the time-series have less influence on the analysis), along with data indicating whether stimulation by any of the modalities is in progress. The pain datum may be coincident with the most recent time point of the other data, or the data may be evaluated over some fixed time interval prior to the time at which a pain datum is acquired. In the former case, the objective is to explain the level of pain based upon the coincident values of the other data, and in the latter case, the objective is to predict the occurrence of future pain from the other data. Thus, the SVM is trained to predict the presence of the specified level of pain (or greater) from the other coincident data, and/or it is trained to predict from the other data whether the level of pain will be experienced some specified number of seconds into the future. By extrapolating the values of the other data into the future, it is also possible to use those extrapolated data to predict the future value of the patient's pain, using an SVM that is trained with concurrent other data, but by training the SVM with other data that had been evaluated at times prior to acquisition of the pain data, the extrapolation step is avoided. Because the SVM analysis is repeated for all possible pain levels, the analysis collectively endeavors to predict the current or future numerical value of pain [Christopher J. C. BURGES. A tutorial on support vector machines for pattern recognition. Data Mining and Knowledge Discovery 2 (1998), 121-167; J. A. K. SUYKENS, J. Vandewalle, B. De Moor. Optimal Control by Least Squares Support Vector Machines. Neural Networks 14 (2001):23-35; SAPANKEVYCH, N. and Sankar, R. Time Series Prediction Using Support Vector Machines: A Survey. IEEE Computational Intelligence Magazine 4 (2, 2009): 24-38; Alex J. SMOLA and Bernhard Scholkopf. A tutorial on support vector regression. Journal of Statistics and Computing 14 (3, 2004):199-222].

The SVM is trained using as wide a range of data that the patient is expected to experience during activities of daily living. For example, the data will have been acquired over the course of 24 hours using ambulatory monitoring. Data will also have been acquired under a wide range of deliberate reversible stimulation provocations that might be used therapeutically. Redundancy of the data acquisition conditions will reveal the extent to which the patient's physiology exhibits adaptation or habituation to a given set of provocations, producing different levels of pain for a given set of the other data, thereby confounding the predictability of the pain.

Simplification of the SVM training is accomplished in part by avoiding the use of the raw data, but instead by using features that have been extracted from the raw data. For example, rather than train the SVM using the spontaneous voltage fluctuations measured from each of the electrodes of the lead device, one would instead use the total power in frequency bands extracted from those fluctuations, as a function of time. As another example, instead of using voltages measured from scalp electrodes, one would instead use measured amplitudes and latencies of the corresponding evoked potentials to train the SVM. Simplification of the training may also make use of methods that eliminate consideration of variables that are found to have little effect on the prediction of pain [Felipe ALONSO-Atienza, José-Luis Rojo-Álvarez, Alfredo Rosado-Muñoz, Juan J. Vinagre, Arcadi García-Alberola, Gustavo Camps-Valls. Feature selection using support vector machines and bootstrap methods for ventricular fibrillation detection. Expert Systems with Applications 39 (2012): 1956-1967]. After training the SVM to predict the occurrence of pain from the other data, success of the SVM is tested with data that were not used for the SVM training. If the success rate is not adequate because it produces too many false positives or negatives, training and testing of the SVM continues until the training is judged to be adequate.

One benefit of training and testing an SVM is that it will provide the physician with a better sense of which variables are responsible for the patient's pain and which stimulation modalities and parameter ranges would most likely effect a reduction in the patient's pain. Thus, analysis of the data concerning the patient's pain, along with the other data that may predict that pain, provides diagnostic information to the physician. With that information, the physician would reduce the time and effort needed for trial-and-error experimentation with stimulation modalities and parameter values. The physician may also use the diagnostic data that has been collected for a population of patients, in order to determine how subsets of patients having similar diagnostic data respond to different treatment modalities.

However, a greater benefit of training and testing the SVM is that it may be incorporated into an autonomous or semi-autonomous closed-loop system in which the system itself selects stimulation modalities and the corresponding stimulation parameter values (waveform type, pulse amplitude, frequency, etc.) that may vary according to the patient's currently measured state. Such closed-loop systems have been described as an advance in deep brain stimulation methodology, such that inherently better therapeutic results can be achieved [STANSLANSKI S, Afshar P, Cong P, Giftakis J, Stypulkowski P, Carlson D, Linde D, Ullestad D, Avestruz A T, Denison T. Design and validation of a fully implantable, chronic, closed-loop neuromodulation device with concurrent sensing and stimulation. IEEE Trans Neural Syst Rehabil Eng 20 (4, 2012):410-421; R. Mark RICHARDSON. Closing the Loop in Neuromodulation: Concurrent Sensing and Stimulation. Neurosurgery 71 (2, 2012): N19-N20; AFSHAR P, Khambhati A, Stanslaski S, Carlson D, Jensen R, Linde D, Dani S, Lazarewicz M, Cong P, Giftakis J, Stypulkowski P, Denison T. A translational platform for prototyping closed-loop neuromodulation systems. Front Neural Circuits 6 (2013):117, pp. 1-15]. However, such closed-loop systems have not been disclosed heretofore for the treatment of lower back pain.

Using the lead devices and physiological measurements that are disclosed herein, any known feedback or control system method may be used to close the stimulation loop [Karl Johan ASTROM & Richard M. Murray. Feedback Systems: An Introduction for Scientists and Engineers. Princeton N.J.: Princeton University Press, 2008; Torkel GLAD and Lennart Ljung. Control Theory. Multivariable and Nonlinear Methods. New York: Taylor and Francis, 2000; Zdzislaw BUBNICKI. Modern Control Theory. Berlin: Springer, 2005]. However, the trained and tested SVM may be best suited to the use of feedforward control methods, as now described [Coleman BROSILOW, Babu Joseph. Feedforward Control (Chapter 9) In: Techniques of Model-Based Control. Upper Saddle River, N.J.: Prentice Hall PTR, 2002. pp. 221-240].

For any given current values of the pain and other measured values, the system provides those other measured values to the SVM as input, which predicts the corresponding level of pain. The system also searches through its database of previously recorded data for examples in which the patient exhibited similar values of the other measured values and uses those values to predict the pain that had been previously measured. To the extent that the SVM successfully predicts the level of current or previously recorded values of pain, the SVM is determined to be useful under the patient's current state.

Then, for all such similar examples, the system searches for stimulation modalities and parameters that had been applied under similar measured circumstances, to find the ones that led to the greatest reduction of pain, in the moments after their application. Initially, the stimulation modalities and parameters will correspond to the deliberate provocations of single pulses and bursts of pulses with different stimulation modalities, which had been made in connection with the measurement of evoked potentials. The SVM is presented with those data as input, this time with the variable(s) representing various stimulation modalities set to values indicating the presence of their application, as well as having a range of possible stimulation parameters. The SVM then predicts the level of pain under those stimulation parameters. To the extent that the SVM can successfully predict the level of previously recorded values of pain following stimulation, it is determined that the modality and parameter settings that the SVM predicts to bring about the greatest reduction in pain are therapeutically appropriate, whether or not those modality and particular parameter settings had been applied previously. Those stimulation modalities and parameter settings can then be applied to the patient using the pulse generator. When the measured values of the variables subsequently change beyond a de minimis amount, the process can be repeated and new stimulation modalities and/or parameter settings are automatically applied to the patient using the pulse generator. Therefore, one aspect of the closed-loop embodiment of the present invention is that the stimulation modalities and their corresponding stimulation parameters are generally not set by the physician even temporarily, and in that sense, the present invention differs fundamentally from neurostimulation treatment for back pain as it is currently practiced.

If no application of stimulation modalities had been performed when the pain and other measured variables were similar to the patient's current values of those variables, the system may then randomly apply single pulses and bursts of pulses using the different stimulation modalities. The patient's measured response to those random applications will then be added to the database of recordings for future reference. Once the database of responses is sufficiently comprehensive, the SVM may be retrained and tested using the updated database of measurements, and the system is ready for therapeutic application under a wider range of conditions. In order that the system be able to promptly select a stimulation modality and set of stimulation parameters, the responses to different stimulations under different measured states of the patient may have been preprocessed and indexed offline by the computer housing the database of measurements. Otherwise, if the search for stimulation modalities and parameters to find the ones that may lead to the greatest reduction of pain will take a significant amount of computer processing time, the SVM should be trained to predict into the future the pain that the patient will experience, in which the future time is approximately equal to the computer's processing time.

The SVM is regularly retrained and tested using data that accumulates long after the lead device has been implanted into the patient. Therefore, one expects that the ability of the SVM to predict the most effective stimulation modality and stimulation parameter values will improve continuously, and the application of those stimulation modalities and parameters will eventually lead to a significant reduction of the patient's pain. However, if the pain persists even after extended use of the closed-loop system, the physician has the option of applying irreversible stimulation using any of the modalities that were described above. Selection among the irreversible modalities may be based upon a determination that one of the reversible modalities had the greatest effect in reducing the patient's pain, however incomplete that reduction was.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for treating a patient having a spine comprising an epidural space and a posterior longitudinal ligament, wherein the patient has a diseased vertebral disc, wherein the method includes:
   implanting a neurostimulation lead within an anterior portion of the epidural space adjacent to the posterior longitudinal ligament, wherein the neurostimulation lead has a plurality of electrodes that are adjacent to the diseased vertebral disc, wherein the neurostimulation lead is a paddle lead and the plurality of electrodes are disposed on the same side of the paddle lead, wherein the paddle lead is implanted such that the electrodes face the posterior longitudinal ligament;
   and wherein said treating is performed by a person who may select among treatment neurostimulations comprising: (1) direct inhibition of initiation and/or propagation of an action potential in one or more afferent nociceptor nerves wherein said afferent nerves are caused to increase their mechanical force threshold above which said afferent nerves initiate and/or propagate an action potential; (2) promotion of initiation and/or propagation of an action potential in one or more sympathetic nerves in said posterior longitudinal ligament, whereby initiation and/or propagation of an action potential in one or more afferent nociceptor nerves is caused to be secondarily inhibited; and (3) inhibition of initiation and/or propagation of an action potential in one or more sympathetic nerves in said posterior longitudinal ligament, whereby said inhibited sympathetic nerve is hindered from secondarily promoting initiation and/or propagation of an action potential in one or more afferent nociceptive nerves.

2. A method for treating a patient having a spine comprising an epidural space and a posterior longitudinal ligament, wherein the patient has a diseased vertebral disc, wherein the method includes:
   implanting a neurostimulation lead within an anterior portion of the epidural space adjacent to the posterior longitudinal ligament, wherein the neurostimulation lead has a plurality of electrodes that are adjacent to the diseased vertebral disc; wherein the neurostimulation lead may be a percutaneous or paddle lead and the plurality of electrodes are disposed on the same side of the lead, wherein the lead is implanted such that the electrodes face the posterior longitudinal ligament;
   and wherein said treating is performed by a person who may select among treatment neurostimulations comprising: direct inhibition of initiation and/or propagation of an action potential in one or more afferent nociceptor nerves, wherein said afferent nerves are caused to increase their mechanical force threshold above which said afferent nerves initiate and/or propagate an action potential.

* * * * *